United States Patent
Kim et al.

(10) Patent No.: US 9,278,927 B2
(45) Date of Patent: Mar. 8, 2016

(54) HETEROCYCLIC COMPOUND AND ORGANIC LIGHT-EMITTING DEVICE INCLUDING THE SAME

(75) Inventors: Young-Kook Kim, Yongin (KR); Seok-Hwan Hwang, Yongin (KR); Hye-Jin Jung, Yongin (KR); Jin-O Lim, Yongin (KR); Sang-Hyun Han, Yongin (KR); Se-Jin Cho, Yongin (KR); Jong-Hyuk Lee, Yongin (KR)

(73) Assignee: Samsung Display Co., Ltd., Samsung-ro, Giheung-Gu, Yongin-si, Gyeonggi-Do (KR)

( * ) Notice: Subject to any disclaimer, the term of this patent is extended or adjusted under 35 U.S.C. 154(b) by 1123 days.

(21) Appl. No.: 13/304,459

(22) Filed: Nov. 25, 2011

(65) Prior Publication Data

US 2013/0032787 A1 Feb. 7, 2013

(30) Foreign Application Priority Data

Aug. 3, 2011 (KR) .................. 10-2011-0077370

(51) Int. Cl.
*H01L 51/54* (2006.01)
*C07D 401/12* (2006.01)
(Continued)

(52) U.S. Cl.
CPC ............ *C07D 209/94* (2013.01); *C07D 401/04* (2013.01); *C07D 401/06* (2013.01);
(Continued)

(58) Field of Classification Search
None
See application file for complete search history.

(56) References Cited

U.S. PATENT DOCUMENTS 5,635,308 A 6/1997 Inoue et al.
5,645,948 A 7/1997 Shi et al.
(Continued)

FOREIGN PATENT DOCUMENTS

JP 06228556 8/1994
JP 08012600 1/1996
(Continued)

OTHER PUBLICATIONS

Sakamoto et al., Synthesis, Characterization, and Electron-Transport Property of Perfluorinated Phenylene Dendrimers, J. Am. Chem. Soc. (2000) 122, pp. 1832-1833.
(Continued)

*Primary Examiner* — J. L. Yang
(74) *Attorney, Agent, or Firm* — Robert E. Bushnell, Esq.

(57) ABSTRACT

A heterocyclic compound represented by Formula 1 or Formula 2 below, and an organic light-emitting device including the heterocyclic compound. The organic light-emitting device may include an organic layer containing the heterocyclic compound, and thus may have a low driving voltage, a high-emission efficiency, and long lifespan characteristics.

Formula 1

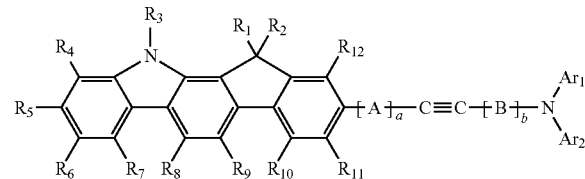

Formula 2

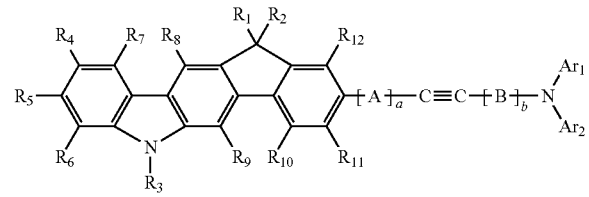

wherein $R_1$ to $R_{12}$, $Ar_1$, $Ar_2$, A, B, a, and b are defined as in the specification.

19 Claims, 1 Drawing Sheet

(51) Int. Cl.

| | | |
|---|---|---|
| *C07D 403/10* | (2006.01) | |
| *C07D 209/94* | (2006.01) | |
| *C07D 401/04* | (2006.01) | |
| *C07D 401/06* | (2006.01) | |
| *C07D 403/04* | (2006.01) | |
| *C07D 403/06* | (2006.01) | |
| *C07D 409/06* | (2006.01) | |
| *C07D 413/06* | (2006.01) | |
| *C07D 471/04* | (2006.01) | |
| *C07D 487/04* | (2006.01) | |
| *C07D 405/04* | (2006.01) | |
| *C07D 405/06* | (2006.01) | |
| *C07D 409/04* | (2006.01) | |
| *C07D 413/04* | (2006.01) | |
| *C07F 9/6568* | (2006.01) | |

(52) U.S. Cl.
CPC ............ *C07D403/04* (2013.01); *C07D 403/06* (2013.01); *C07D 405/04* (2013.01); *C07D 405/06* (2013.01); *C07D 409/04* (2013.01); *C07D 409/06* (2013.01); *C07D 413/04* (2013.01); *C07D 413/06* (2013.01); *C07D 471/04* (2013.01); *C07D 487/04* (2013.01); *C07F 9/65683* (2013.01)

(56) References Cited

U.S. PATENT DOCUMENTS

| | | | |
|---|---|---|---|
| 5,972,247 | A | 10/1999 | Shi et al. |
| 6,465,115 | B2 | 10/2002 | Shi et al. |
| 7,846,559 | B2 | 12/2010 | Hwang et al. |
| 7,875,368 | B2 | 1/2011 | Ohrui et al. |
| 2001/0023029 | A1 | 9/2001 | Shi et al. |
| 2008/0220285 | A1 | 9/2008 | Vestweber et al. |
| 2009/0233937 | A1 | 9/2009 | Ishikawa et al. |
| 2010/0019657 | A1 | 1/2010 | Eum et al. |
| 2011/0037027 | A1 | 2/2011 | Stoessel et al. |
| 2011/0049488 | A1 | 3/2011 | Kim et al. |
| 2011/0204295 | A1 | 8/2011 | Kuwabara et al. |

FOREIGN PATENT DOCUMENTS

| | | |
|---|---|---|
| JP | 2000003782 | 1/2000 |
| JP | 2010195708 | 9/2010 |
| KR | 1020080015865 | 2/2008 |
| KR | 1020090073925 | 7/2009 |
| KR | 1020100003624 | 1/2010 |
| KR | 1020100108903 | 10/2010 |
| KR | 1020100130197 | 12/2010 |
| TW | 201004904 A1 | 2/2010 |
| WO | 2011006568 | 1/2011 |

OTHER PUBLICATIONS

Adachi et al., Confinement of charge carriers and molecular excitons within 5nm thick emitter layer in organic electroluminescent devices with a double heterostructure, Appl. Phys. Lett. (1990) 57, 531, pp. 531-533.

Tang et al., Organic electroluminescent diodes, Appl. Phys. Lett. (1987) 51, 913, pp. 913-915.

Chemistry Letters 2001: Diphenylamino-Substituted 2,5-Diarysiloles for Single-Layer Organic Electroluminescent Device by Shigehiro Yamaguchi et al. (Received Nov. 10, 2000).

Taiwanese Office Action issued on 4 Nov. 2015 by Taiwan Patent Office in connection with Taiwanese Patent Application No. 101116241, which also claims Korean Patent Application No. 10-2011-0077370 as its priority document.

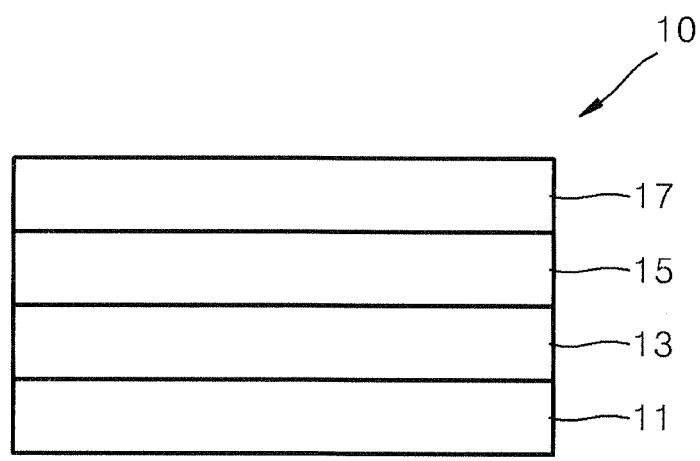

HETEROCYCLIC COMPOUND AND ORGANIC LIGHT-EMITTING DEVICE INCLUDING THE SAME

CLAIM OF PRIORITY

This application makes reference to, incorporates the same herein, and claims all benefits accruing under 35 U.S.C. §119 from an application for HETEROCYCLIC COMPOUND AND ORGANIC LIGHT-EMITTING DEVICE INCLUDING THE SAME earlier filed in the Korean Intellectual Property Office on 3 Aug. 2011 and there duly assigned Serial No. 10-2011-0077370.

BACKGROUND OF THE INVENTION

1. Field of the Invention

The present invention relates to a heterocyclic compound represented by Formula 1 or Formula 2 and an organic light-emitting device including the heterocyclic compound.

2. Description of the Related Art

Organic light-emitting devices (OLEDs), which are self-emitting devices, have advantages such as wide viewing angles, excellent contrast, quick response, high brightness, excellent driving voltage characteristics, and the ability to provide multicolored images.

A typical OLED has a structure including a substrate, an anode, a hole transport layer (HTL), an emission layer (EML), an electron transport layer (ETL), and a cathode which are sequentially stacked on the substrate. In this regard, the HTL, the EML, and the ETL are organic thin films formed of organic compounds.

An operating principle of an OLED having the above-described structure is as follows. When a voltage is applied between the anode and the cathode, holes injected from the anode move to the EML via the HTL, and electrons injected from the cathode move to the EML via the ETL. The holes and electrons recombine in the EML to generate excitons. When the excitons drop from an excited state to a ground state, light is emitted.

SUMMARY OF THE INVENTION

The present invention provides a novel heterocyclic compound for an organic light-emitting device with a low voltage, a high luminance, a high efficiency, and a long lifespan.

The present invention provides an organic light-emitting device including the heterocyclic compound.

According to an aspect of the present invention, there is provided a heterocyclic is compound represented by Formula 1 or Formula 2 below:

Formula 1

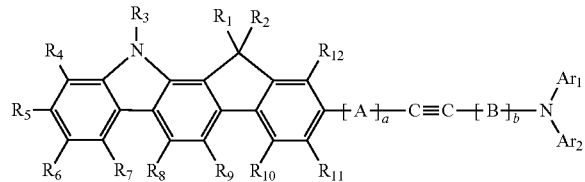

Formula 2

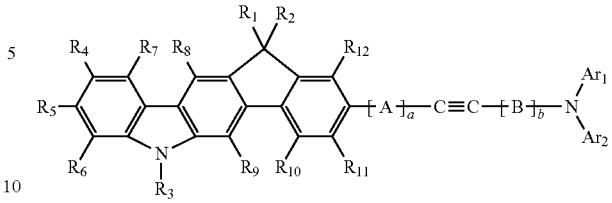

wherein, in Formulae 1 and 2, $Ar_1$ and $Ar_2$ are each independently a substituted or unsubstituted $C_5$-$C_{30}$ aryl group or a substituted or unsubstituted $C_3$-$C_{30}$ heteroaryl group; A and B are a divalent linker, and each independently one of —Si($R_{13}$)($R_{14}$)—, —C=C($R_{15}$)($R_{16}$))—, —O—, —S—, —C(=O)—, —P(=O)($R_{17}$)—, —S(=O)—, —(O=)S(=O)—, a substituted or unsubstituted $C_5$-$C_{30}$ arylene group, or a substituted or unsubstituted $C_3$-$C_{30}$ heteroarylene group; $R_1$ to $R_{17}$ are each independently a hydrogen atom, a deuterium atom, a halogen atom, a hydroxyl group, a cyano group, a nitro group, a carboxyl group, a substituted or unsubstituted $C_1$-$C_{30}$ alkyl group, a substituted or unsubstituted $C_2$-$C_{30}$ alkenyl group, a substituted or unsubstituted alkynyl group, a substituted or unsubstituted $C_1$-$C_{30}$ alkoxy group, a substituted or unsubstituted $C_3$-$C_{30}$ cycloalkyl group, a substituted or unsubstituted $C_3$-$C_{30}$ cycloalkenyl group, a substituted or unsubstituted $C_3$-$C_{30}$ aryl group, a substituted or unsubstituted $C_2$-$C_{30}$ heteroaryl group, a substituted or unsubstituted $C_5$-$C_{30}$ aryloxy group, a substituted or unsubstituted $C_3$-$C_{30}$ arylthio group, or an amino group substituted with a substituted or unsubstituted $C_5$-$C_{30}$ aryl group; and a is an integer from 0 to 3, and b is an integer from 0 to 3, wherein if a is 2 or greater, the two or more A are identical to or different from each other, and if b is 2 or greater, the two or more B are identical to or different from each other.

According to another aspect of the present invention, there is provided an organic light-emitting device including: a first electrode; a second electrode disposed opposite to the first electrode; and an organic layer disposed between the first electrode and the second electrode, the organic layer including at least one layer and the heterocyclic compounds of Formula 1 or Formula 2 described above.

BRIEF DESCRIPTION OF THE DRAWING

A more complete appreciation of the present invention, and many of the attendant advantages thereof, will be readily apparent as the present invention becomes better understood by reference to the following detailed description when considered in conjunction with the accompanying drawing, in which like reference symbols indicate the same or similar to components, wherein:

FIG. 1 schematically illustrates a structure of an organic light-emitting device according to an embodiment of the present invention.

DETAILED DESCRIPTION OF THE INVENTION

The present invention will now be described more fully with reference to the accompanying drawing, in which exemplary embodiments of the present invention are shown.

According to an aspect of the present invention, there is provided a heterocyclic compound represented by Formula 1 or 2 below:

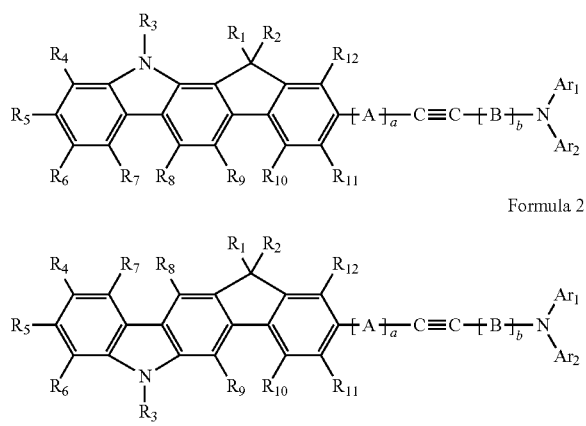

Formula 1

Formula 2 wherein, in Formulae 1 and 2, $Ar_1$ and $Ar_2$ are each independently a substituted or unsubstituted $C_5$-$C_{30}$ aryl group or a substituted or unsubstituted $C_3$-$C_{30}$ heteroaryl group; A and B are a divalent linker, and each independently one of —Si$(R_{13})(R_{14})$—, —C(=C($R_{15}$)($R_{16}$))—, —O—, —S—, —C(=O)—, —P(=O)($R_{17}$)—, —S(=O)—, —(O=)S(=O)—, a substituted or unsubstituted $C_5$-$C_{30}$ arylene group, or a substituted or unsubstituted $C_3$-$C_{30}$ heteroarylene group; and $R_1$ to $R_{17}$ are each independently a hydrogen atom, a deuterium atom, a halogen atom, a hydroxyl group, a cyano group, a nitro group, a carboxyl group, a substituted or unsubstituted $C_1$-$C_{30}$ alkyl to group, a substituted or unsubstituted $C_2$-$C_{30}$ alkenyl group, a substituted or unsubstituted $C_7$-$C_{30}$ alkynyl group, a substituted or unsubstituted $C_1$-$C_{30}$ alkoxy group, a substituted or unsubstituted $C_3$-$C_{30}$ cycloalkyl group, a substituted or unsubstituted $C_3$-$C_{30}$ cycloalkenyl group, a substituted or unsubstituted $C_3$-$C_{30}$ aryl group, a substituted or unsubstituted $C_2$-$C_{30}$ heteroaryl group, a substituted or unsubstituted $C_5$-$C_{30}$ aryloxy group, a substituted or unsubstituted $C_5$-$C_{30}$ arylthio group, or an amino group substituted with a substituted or unsubstituted $C_5$-$C_{50}$ aryl group. Optionally, $R_1$ and $R_2$ may be linked together to form a substituted or unsubstituted aryl group. a is an integer from 0 to 3. If a is 2 or greater, two or more A may be the same as or different from each other. b is an integer from 0 to 3. If b is 2 or greater, two or more B may be the same as or different from each other.

In some embodiments, $R_1$ to $R_{17}$ are each independently a hydrogen atom, a deuterium atom, a halogen atom, a hydroxyl group, a cyano group, a nitro group, a carboxyl group, a substituted or unsubstituted methyl group, a substituted or unsubstituted ethyl group, a substituted or unsubstituted propyl group, a substituted or unsubstituted butyl group, a to substituted or unsubstituted pentyl group, a substituted or unsubstituted phenyl group, a substituted or unsubstituted biphenyl group, a substituted or unsubstituted terphenyl group, a substituted or unsubstituted naphthyl group, a substituted or unsubstituted phenoxy group; a substituted or unsubstituted fluorenyl group, a substituted or unsubstituted spirofluorenyl group, a substituted or unsubstituted carbozolyl group, a substituted or unsubstituted phenanthrenyl group, a substituted or unsubstituted pyranyl group, a substituted or unsubstituted pyridinyl group, a substituted or unsubstituted pyrimidinyl group, a substituted or unsubstituted diazinyl group, a substituted or unsubstituted triazinyl group, a substituted or unsubstituted quinolinyl group, a substituted or unsubstituted benzoimidazolyl group, a substituted or unsubstituted benzoxazolyl group, a substituted or unsubstituted pentalenyl group, a substituted or unsubstituted indenyl group, a substituted or unsubstituted azulenyl group, a substituted or unsubstituted heptalenyl group, a substituted or unsubstituted indacenyl group, a substituted or unsubstituted acenaphthyl group, a substituted or unsubstituted phenalenyl group, a substituted or unsubstituted phenanthridinyl group, a substituted or unsubstituted anthryl group, a substituted or unsubstituted fluoranthenyl group, a substituted or unsubstituted triphenylenyl group, a substituted or unsubstituted pyrenyl group, a substituted or unsubstituted chrysenyl group, a substituted or unsubstituted naphthacenyl group, a substituted or unsubstituted picenyl group, a substituted or unsubstituted perylenyl group, a substituted or unsubstituted pentaphenyl group, a substituted or unsubstituted hexacenyl group, a substituted or unsubstituted pyrrolyl group, a substituted or unsubstituted imidazolinyl group, a substituted or unsubstituted pyrazolyl group, a substituted or unsubstituted imidazopyridinyl group, a substituted or unsubstituted pyrazinyl to group, a substituted or unsubstituted imidazopyrimidinyl group, a substituted or unsubstituted pyridazinyl group, a substituted or unsubstituted indolyl group, a substituted or unsubstituted indolizinyl group, a substituted or unsubstituted isoindolizinyl group, a substituted or unsubstituted pyridoindolizinyl group, a substituted or unsubstituted indazolyl group, a substituted or unsubstituted carbazolyl group, a substituted or unsubstituted purinyl group, a substituted or unsubstituted benzoquinolinyl group, a substituted or unsubstituted phthalazinyl group, a substituted or unsubstituted naphthyridinyl group, a substituted or unsubstituted quinoxalinyl group, a substituted or unsubstituted quinazolinyl group, a substituted or unsubstituted cinnolinyl group, a substituted or unsubstituted phenazinyl group, a substituted or unsubstituted furanyl group, a substituted or unsubstituted benzofuranyl group, a substituted or unsubstituted dibenzofuranyl group, a substituted or unsubstituted thiophenyl group, a substituted or unsubstituted benzothiophenyl group, a substituted or unsubstituted dibenzothiophenyl group, a substituted or unsubstituted thiazolyl group, a substituted or unsubstituted isothiazolyl group, a substituted or unsubstituted benzothiazolyl group, a substituted or unsubstituted oxazolyl group, a substituted or unsubstituted isoxazolyl group, a substituted or unsubstituted oxadiazolyl group, a substituted or unsubstituted triazolyl group, or a substituted or unsubstituted tetrazolyl group. Optionally, $R_1$ and $R_2$ may be linked together to form a substituted or unsubstituted fluorenyl group.

In some embodiments, $R_1$ to $R_{17}$ may be each independently one of a hydrogen atom, a deuterium atom, a halogen atom, a substituted or unsubstituted methyl group, a substituted or unsubstituted propyl group, a substituted or unsubstituted butyl group, and groups represented by Formulae 2A to 2P below, but are not limited thereto:

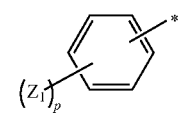

Formula 2A

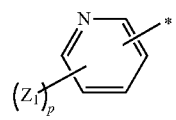

Formula 2B

-continued

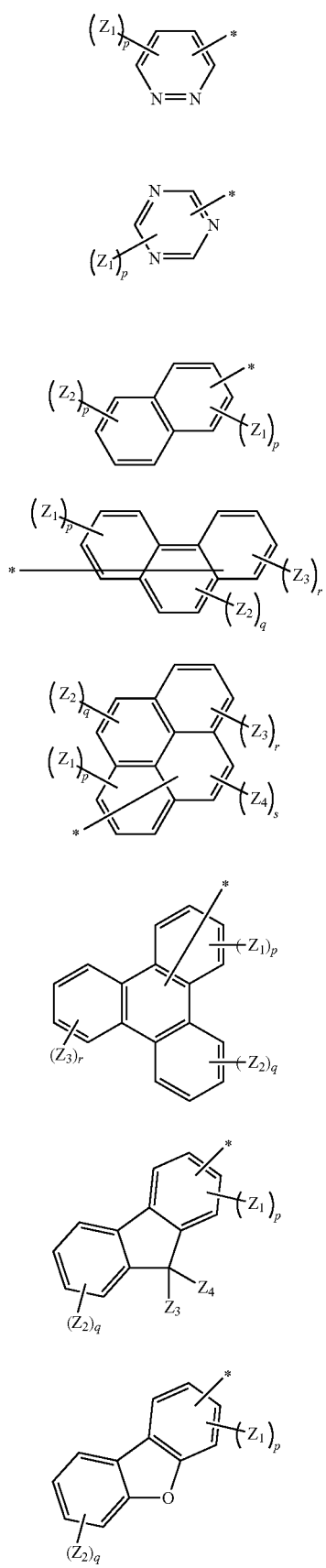

Formula 2C

Formula 2D

Formula 2E

Formula 2F

Formula 2G

Formula 2H

Formula 2I

Formula 2J

-continued

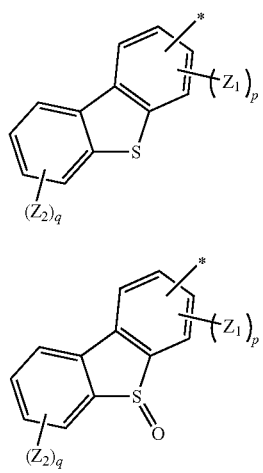

Formula 2K

Formula 2L

Formula 2M

Formula 2N

Formula 2O

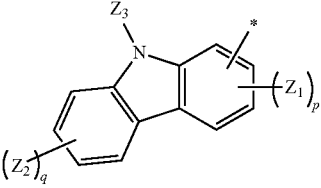

Formula 2P

In Formulae 2A to 2P, $Z_1$, $Z_2$, $Z_3$, and $Z_4$ are each independently one of a hydrogen atom, a deuterium atom, a halogen atom, a hydroxyl group, a cyano group, a substituted or unsubstituted methyl group, a substituted or unsubstituted ethyl group, a substituted or unsubstituted propyl group, a substituted or unsubstituted butyl group, a substituted or unsubstituted methoxy group, a substituted or unsubstituted ethoxy group, a substituted or unsubstituted ethenyl group, a substituted or unsubstituted phenyl group, a substituted or unsubstituted naphthyl group, a substituted or unsubstituted anthryl group, a substituted or unsubstituted pyridinyl group, a substituted or unsubstituted quinolinyl group, a group represented by —N($Q_1$)($Q_2$), and a group represented by —Si($Q_2$)($Q_4$)($Q_5$), wherein $Q_1$ to $Q_5$ are each independently one of a hydrogen atom, a deuterium atom, a halogen atom, a hydroxyl group, a cyano group, a nitro group, a carboxyl group, a substituted or unsubstituted $C_1$-$C_{30}$ alkyl group, a substituted or unsubstituted $C_2$-$C_{30}$ alkenyl group, a substituted or unsubstituted $C_2$-$C_{30}$ alkynyl group, a substituted or unsubstituted $C_1$-$C_{30}$ alkoxy group, a substituted or unsubstituted $C_3$-$C_{30}$ cycloalkyl group, a substituted or unsubstituted $C_3$-$C_{30}$ cycloalkenyl group, a substituted or unsubstituted $C_5$-$C_{30}$ aryl group, a substituted or unsubstituted $C_3$-$C_{30}$ heteroaryl group, a substituted or unsubstituted $C_5$-$C_{30}$ aryloxy group, and a substituted or unsubstituted $C_5$-$C_{30}$ arylthio group.

In Formulae 2A to 2P, a plurality of each of $Z_1$, $Z_2$, $Z_3$, and $Z_4$ are the same as or different from each other; p, q, r and s are an integer from 1 to 5; and * indicates a binding site.

In some embodiments, $R_1$ to $R_{17}$ may be each independently one of a hydrogen atom, a deuterium atom, a halogen atom, a substituted or unsubstituted methyl group, a substituted or unsubstituted propyl group, a substituted or unsubstituted tert-butyl group, and groups represented by Formulae 3A to 3U below, but are not limited thereto. Optionally, $R_1$ and $R_2$ may be linked together to form a fluorenyl group.

Formula 3A
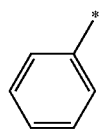

Formula 3B
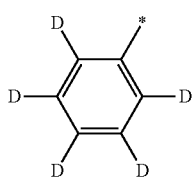

Formula 3C
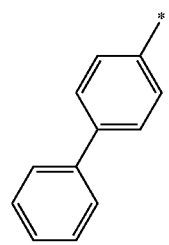

Formula 3D
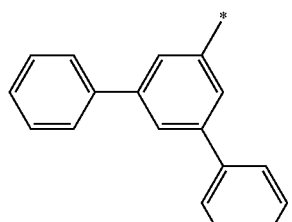

Formula 3E
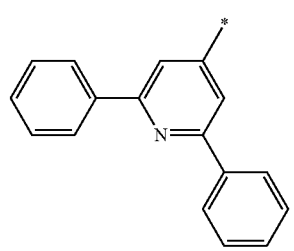

Formula 3F
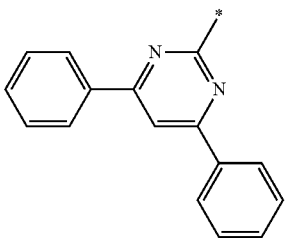

Formula 3G
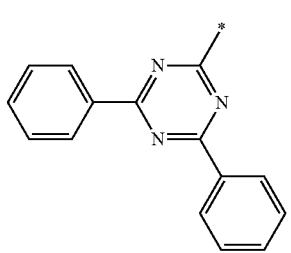

Formula 3H
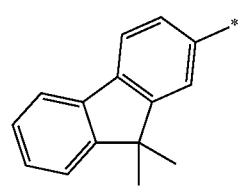

Formula 3I
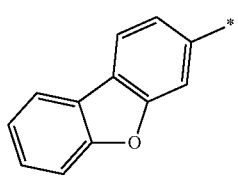

Formula 3J
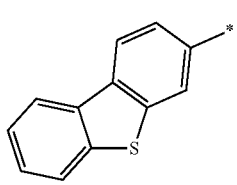

Formula 3K
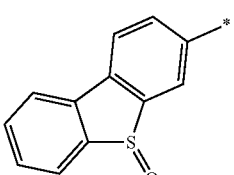

Formula 3L
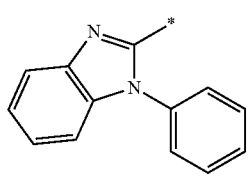

Formula 3M
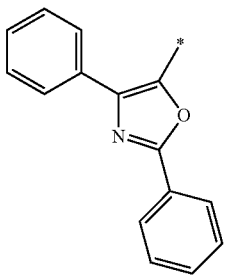

Formula 3N
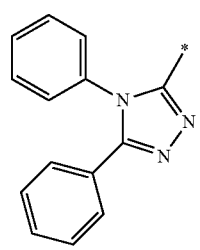

Formula 3O
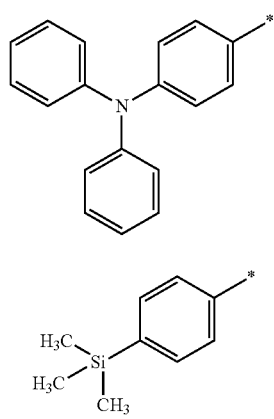

Formula 3P

Formula 3Q
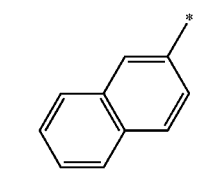

Formula 3R
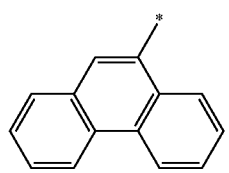

Formula 3S
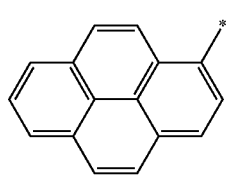

Formula 3T
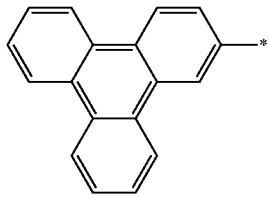

Formula 3U
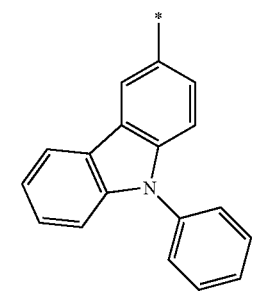

In Formulae 3A to 3U, * indicates a binding site; and D is a deuterium atom.

In some embodiments, $Ar_1$ and $Ar_2$ may be each independently one of a substituted or unsubstituted phenyl group, a substituted or unsubstituted naphthyl group, a substituted or unsubstituted phenanthrenyl group, a substituted or unsubstituted pyrenyl group, a substituted or unsubstituted anthryl group, a substituted or unsubstituted fluorenyl group, a substituted or unsubstituted spirofluorenyl group, a substituted or unsubstituted carbazolyl group, a substituted or unsubstituted pyridinyl group, a substituted or unsubstituted quinolinyl group, a substituted or unsubstituted pyrimidinyl group, a substituted or unsubstituted triazinyl group, a substituted or unsubstituted chrysenyl group, a substituted or unsubstituted perylenyl group, and a substituted or unsubstituted oxadiazolyl group.

For example, $Ar_1$ and $Ar_2$ may be each independently one of the groups represented by Formulae 4A to 4G below, but are not limited thereto:

Formula 4A
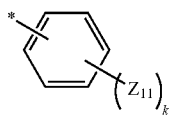

Formula 4B
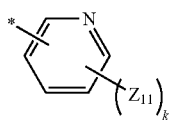

Formula 4C
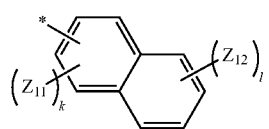

Formula 4D
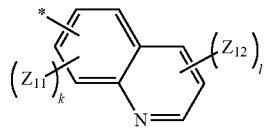

-continued

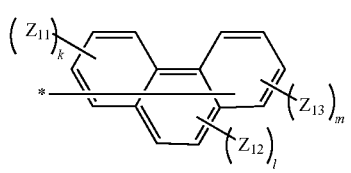

Formula 4E

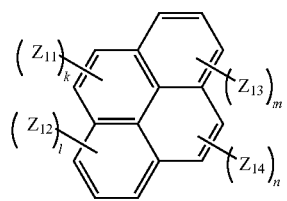

Formula 4F

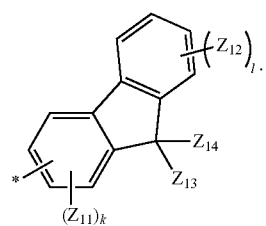

Formula 4G

In Formulae 4A to 4G, $Z_{11}$, $Z_{12}$, $Z_{13}$, and $Z_{14}$ may be each independently one of a hydrogen atom, a deuterium atom, a halogen atom, a hydroxyl group, a cyano group, a substituted or unsubstituted methyl group, a substituted or unsubstituted ethyl group, a substituted or unsubstituted propyl group, a substituted or unsubstituted butyl group, a substituted or unsubstituted methoxy group, a substituted or unsubstituted ethoxy group, a substituted or unsubstituted phenyl group, a substituted or unsubstituted naphthyl group, a substituted or unsubstituted anthryl group, a substituted or unsubstituted pyridinyl group, and a substituted or unsubstituted quinolinyl group, In Formulae 4A to 4G, a plurality of each of $Z_{11}$, $Z_{12}$, $Z_{13}$, and $Z_{14}$ may be the same as or different from each other; k and l may be an integer from 1 to 5; m may be an integer from 1 to 4; n may be an integer from 1 to 2, and * indicates a binding site.

For example, $Ar_1$ and $Ar_2$ may be each independently one of the groups represented by Formulae 5A to 5O below, but are not limited thereto:

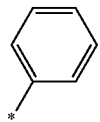

Formula 5A

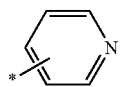

Formula 5B

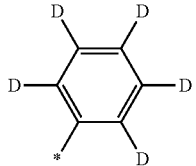

Formula 5C

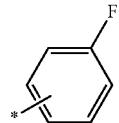

Formula 5D

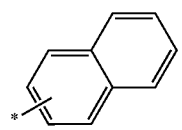

Formula 5E

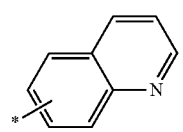

Formula 5F

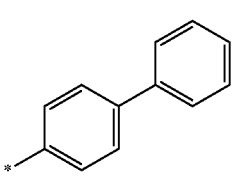

Formula 5G

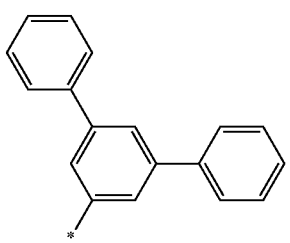

Formula 5H

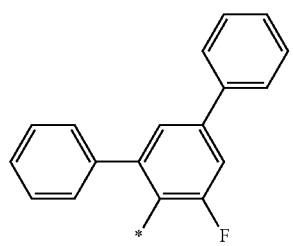

Formula 5I

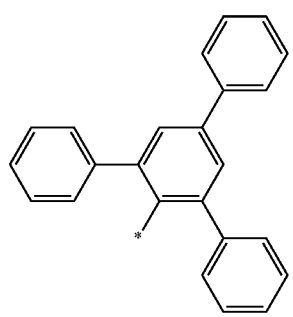

Formula 5J

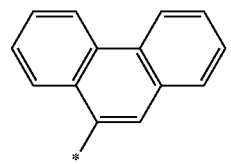

Formula 5K

Formula 5L
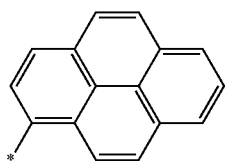

Formula 5M
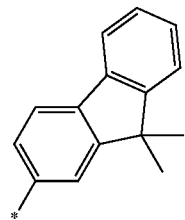

Formula 5N
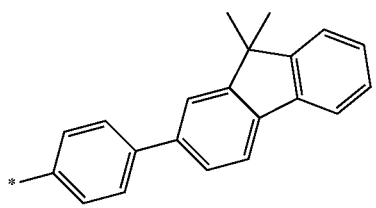

Formula 5O
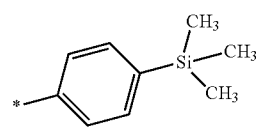

In Formulae 5A to 5O, * indicates a binding site; and D is a deuterium atom.

In some embodiments, A and B may be each independently one of —O—, —S—, —C(=O)—, —S(=O)—, —(O)S(=O)—, and groups represented by Formulae 6A to 6Z below, but are not limited thereto:

Formula 6A
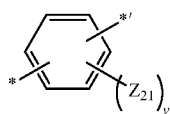

Formula 6B
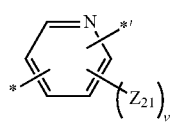

Formula 6C
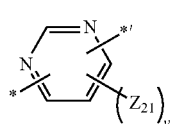

Formula 6D
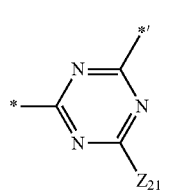

Formula 6E
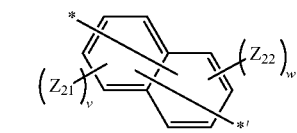

Formula 6F
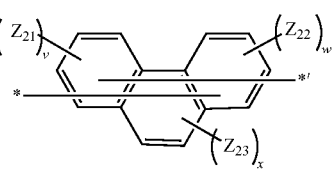

Formula 6G
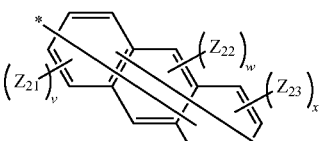

Formula 6H
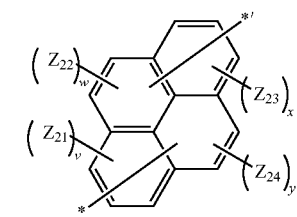

Formula 6I
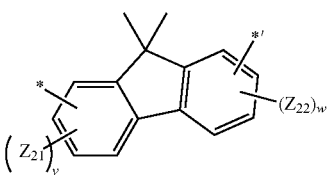

Formula 6J
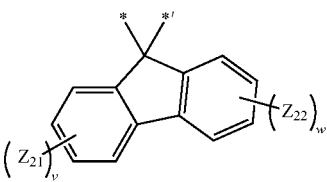

Formula 6K
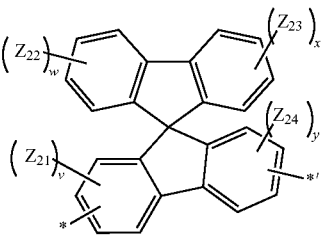

Formula 6L
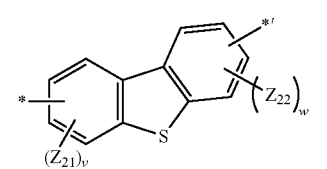

-continued

Formula 6M
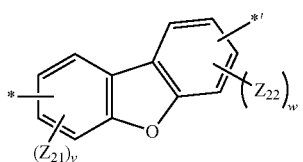

Formula 6N
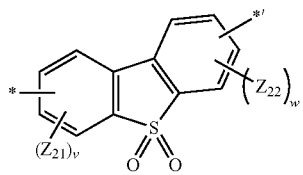

Formula 6O
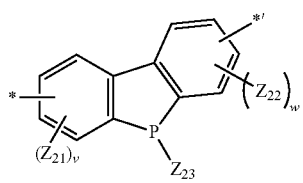

Formula 6P
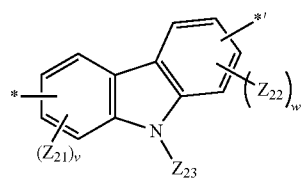

Formula 6Q
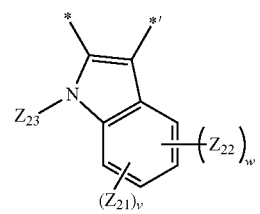

Formula 6R
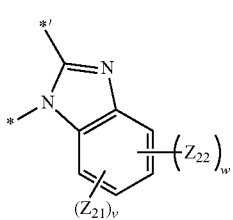

Formula 6S
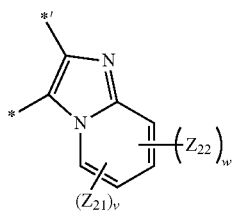

Formula 6T
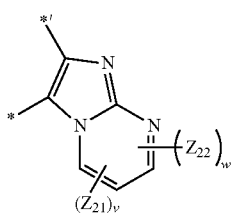

-continued

Formula 6U
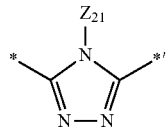

Formula 6V
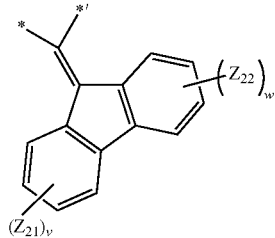

Formula 6W
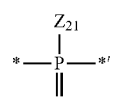

Formula 6X
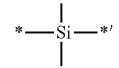

Formula 6Y
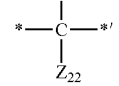

Formula 6Z
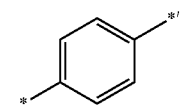

In Formulae 6A to 6Z, $Z_{21}$, $Z_{22}$, $Z_{23}$, and $Z_{24}$ may be each independently one of a hydrogen atom, a deuterium atom, a halogen atom, a hydroxyl group, a cyano group, a substituted or unsubstituted methyl group, a substituted or unsubstituted ethyl group, a substituted or unsubstituted propyl group, a substituted or unsubstituted butyl group, a substituted or unsubstituted methoxy group, a substituted or unsubstituted ethoxy group, a substituted or unsubstituted phenyl group, a substituted or unsubstituted silyl group, a substituted or unsubstituted fluorenyl group, a substituted or unsubstituted naphthyl group, and a substituted or unsubstituted pyridinyl group.

In Formulae 6A and 6Z, a plurality of each of $Z_{21}$, $Z_{22}$, $Z_{23}$, and $Z_{24}$ may be the same as or different from each other; v and w may be an integer from 1 to 4; x and y may be an integer from 1 to 3; and * and *' indicate a binding site.

For example, A and B may be each independently one of —O—, —S—, —C(=O)—, —S(=O)—, —(O=)S(=O)—, and groups represented by Formulae 7A to 7AE below:

Formula 7A

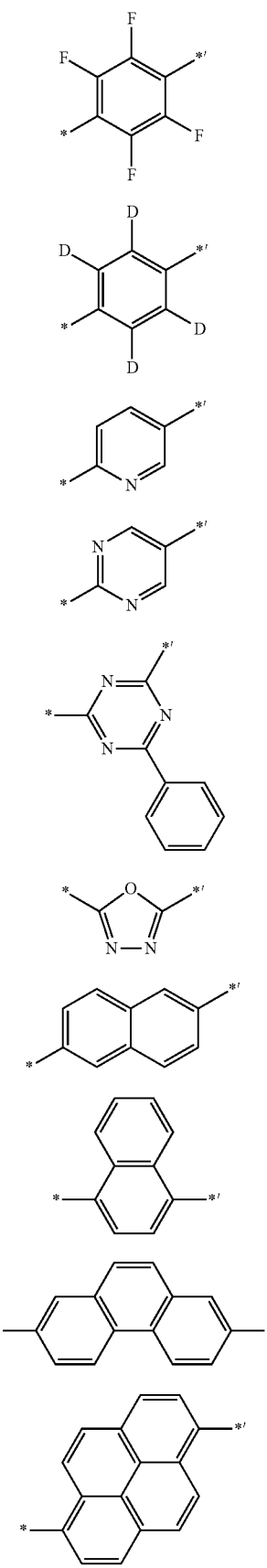
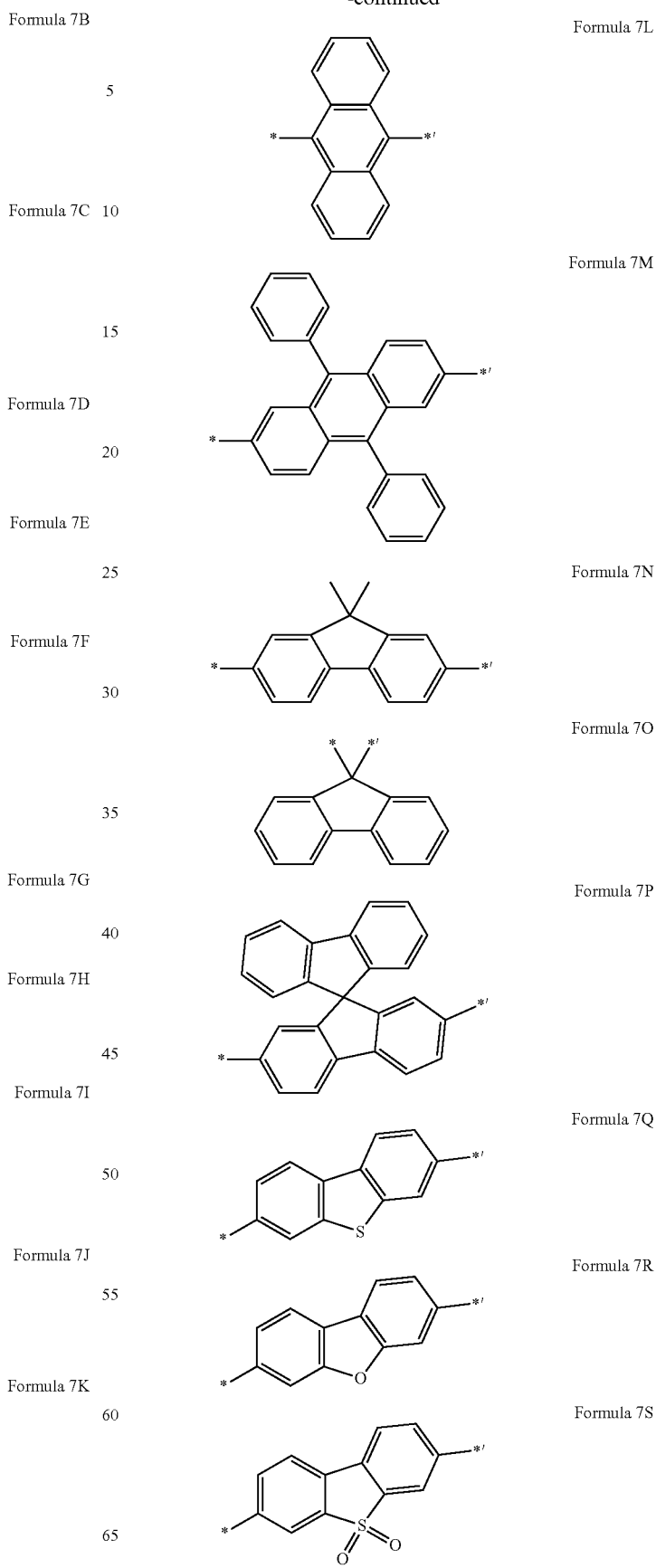

-continued
Formula 7T
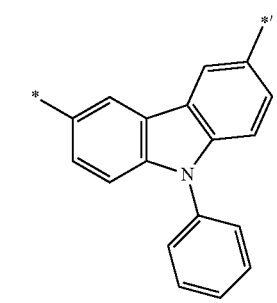
Formula 7U
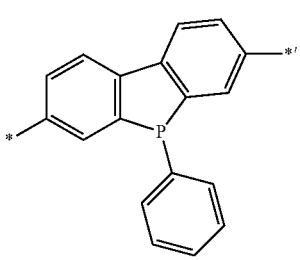
Formula 7V
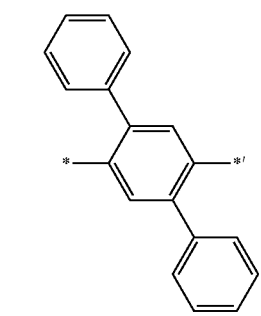
Formula 7W
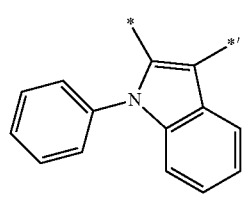
Formula 7X
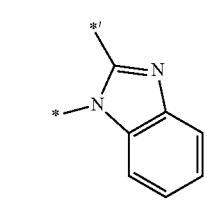
Formula 7Y
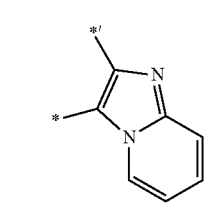
Formula 7Z
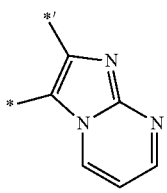
Formula 7AA
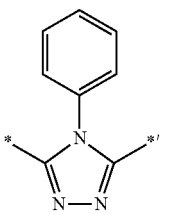
Formula 7AB
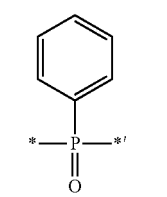
Formula 7AC
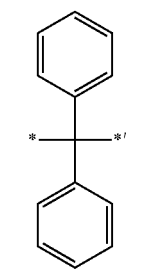
Formula 7AD
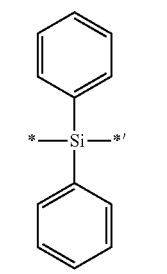
Formula 7AE
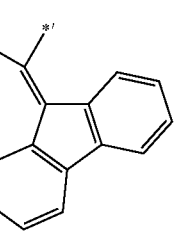
In Formulae 7A to 7AE, * and *' indicate a binding site; and D is a deuterium atom.
The heterocyclic compound represented by Formula 1 or Formula 2 may be one of the Compounds represented by Formulae 1 to 92 below, but is not limited thereto:

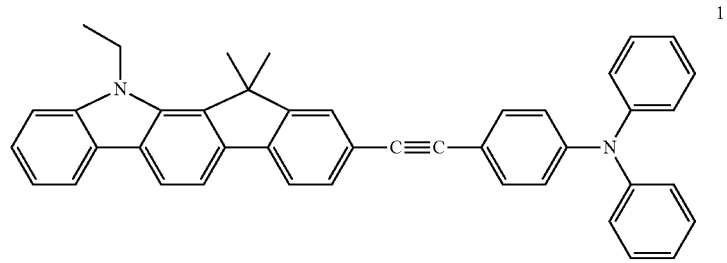
1
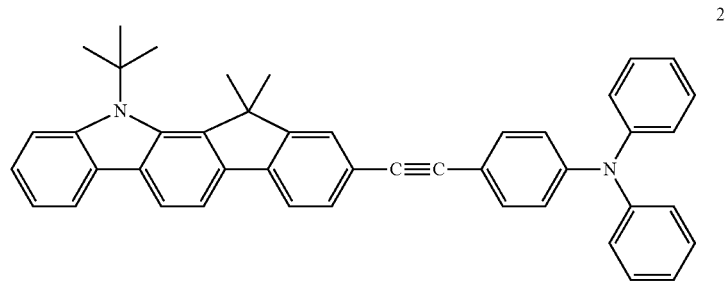
2
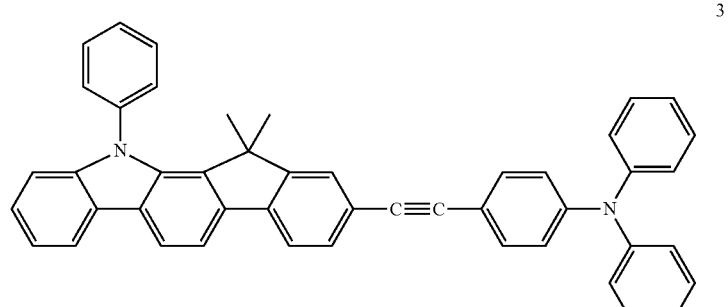
3
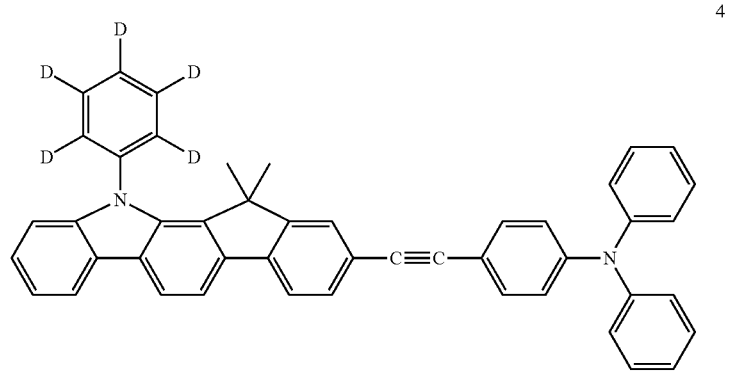
4
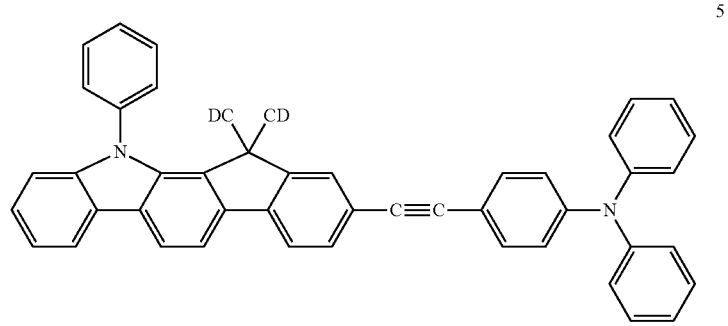
5

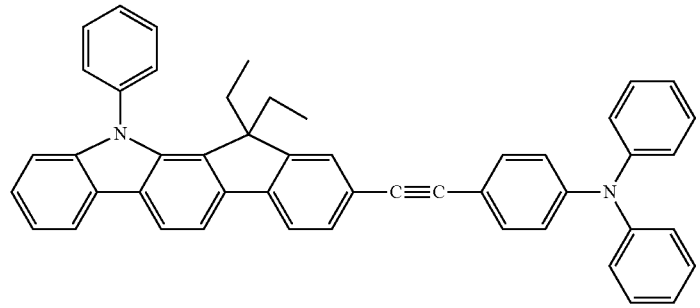

-continued
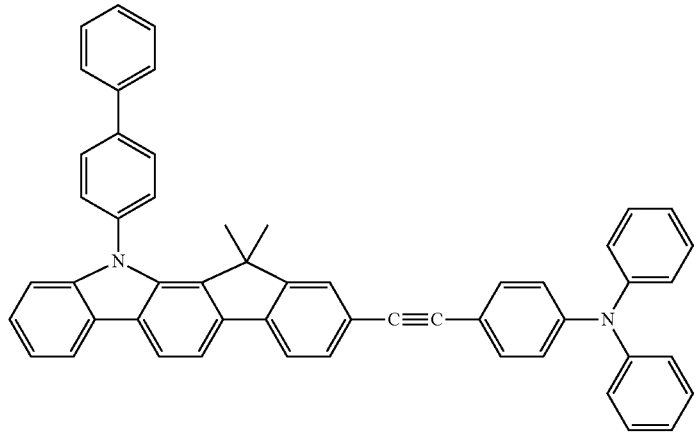
10
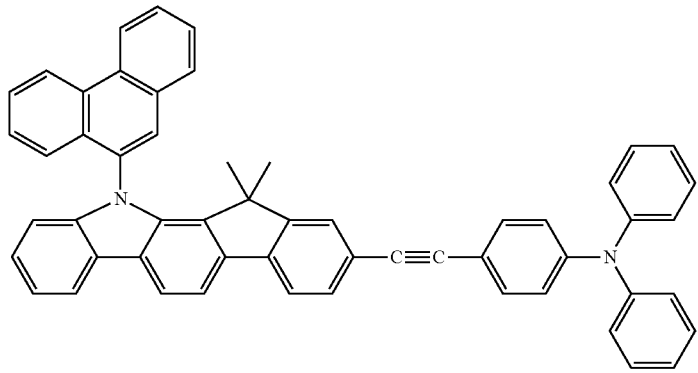
11
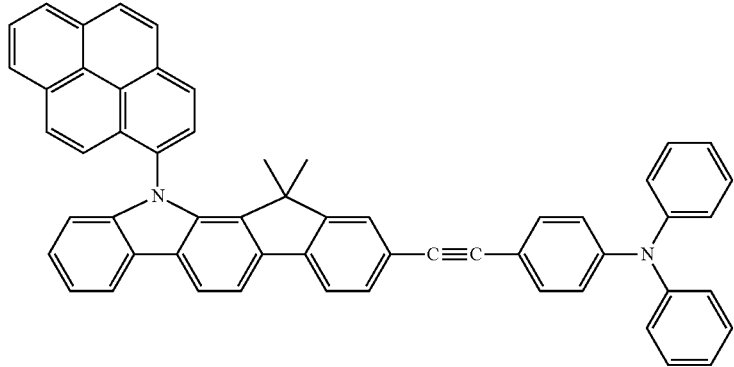
12
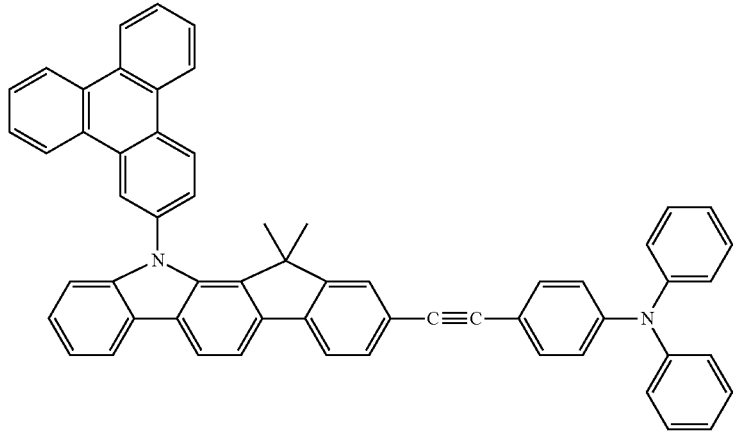
13

-continued
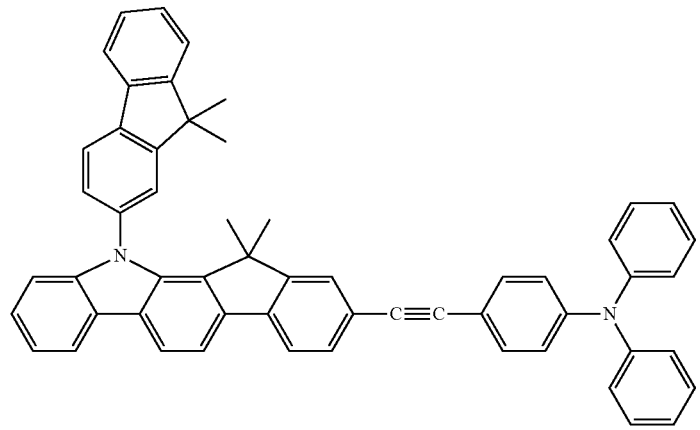
14
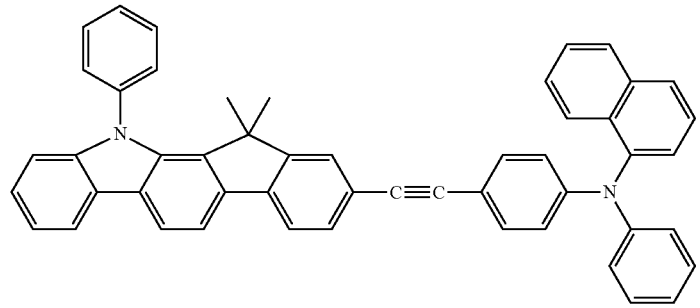
15
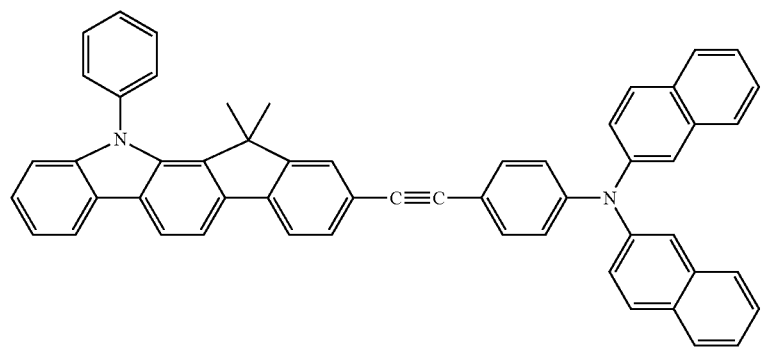
16
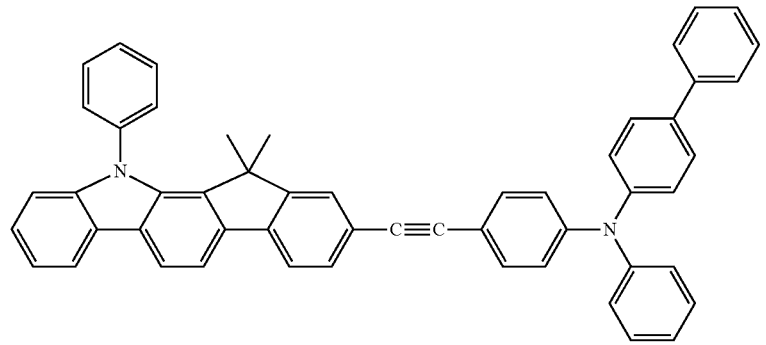
17

18
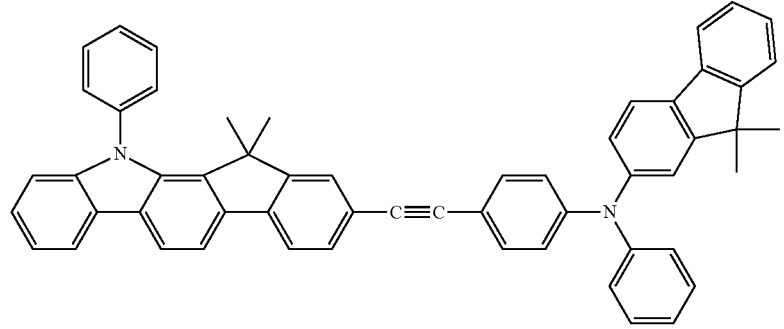
19
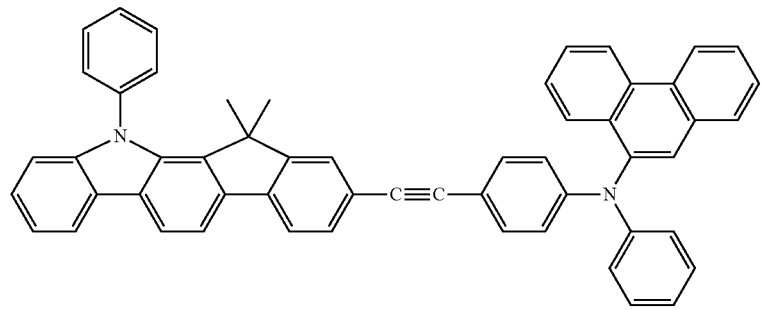
20
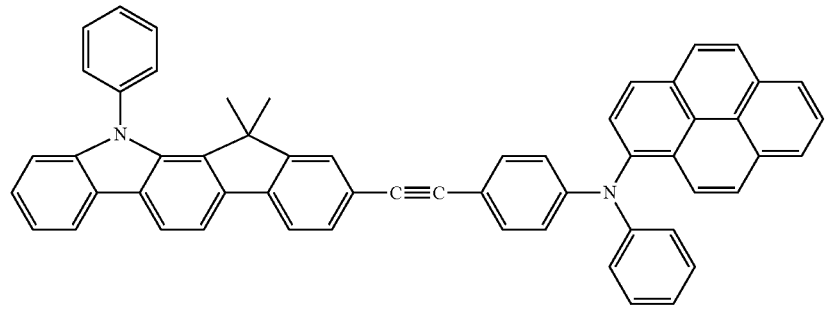
21
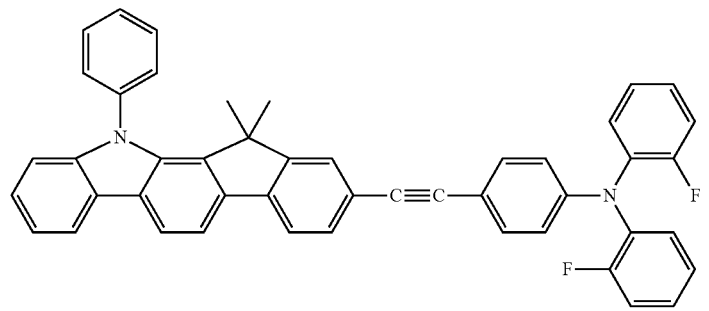
22
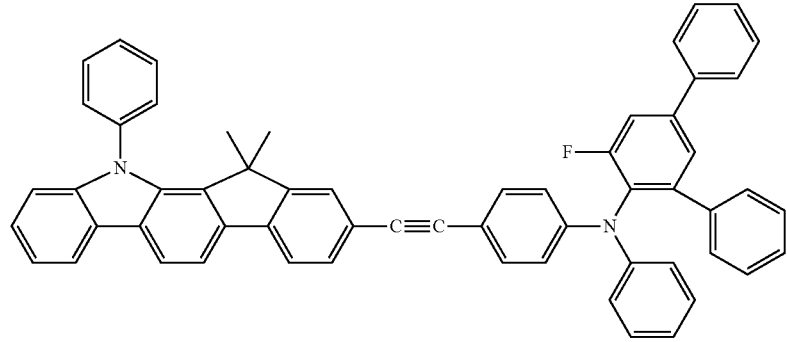

23
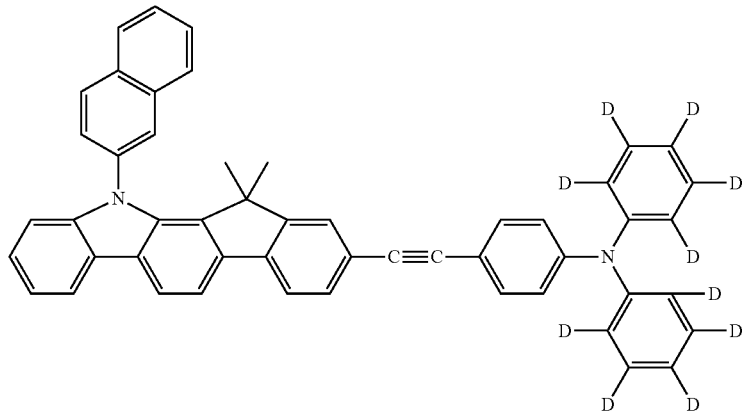
24
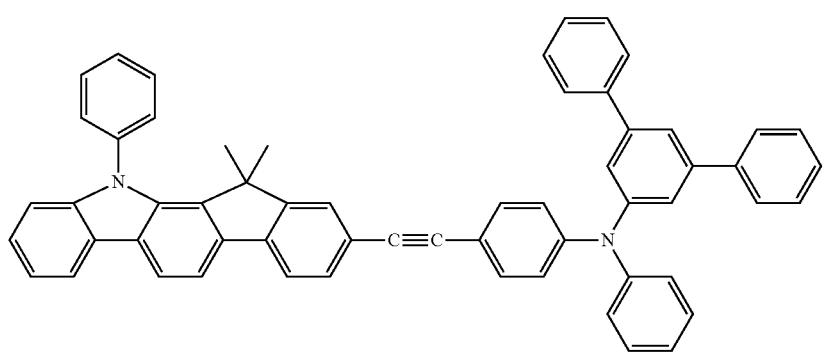
25
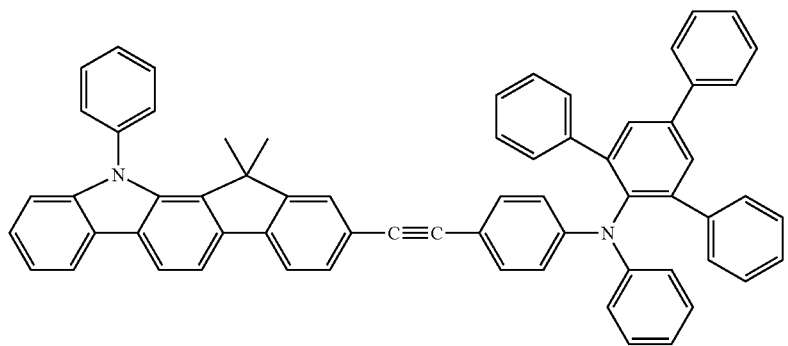
26
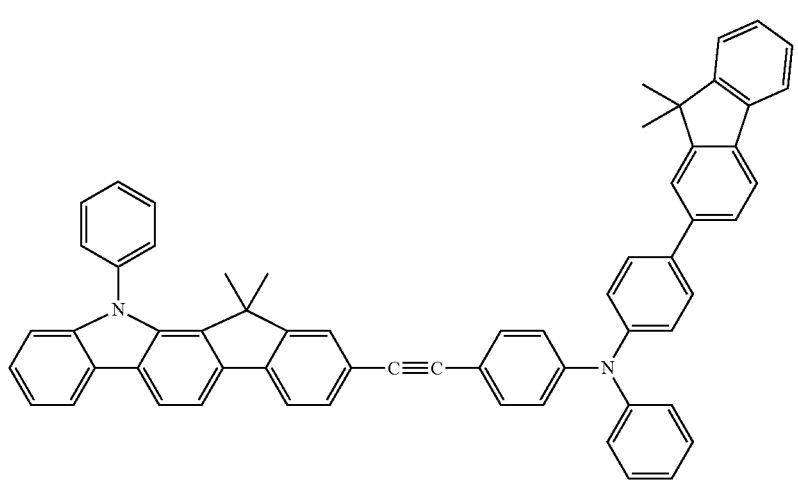

-continued
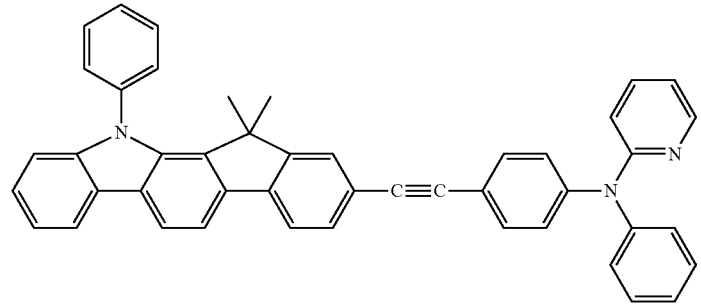
27
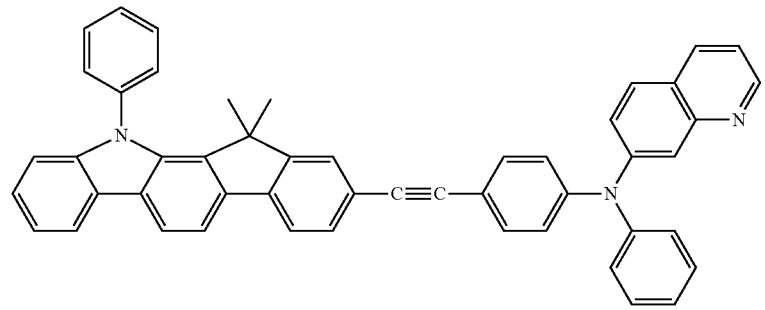
28
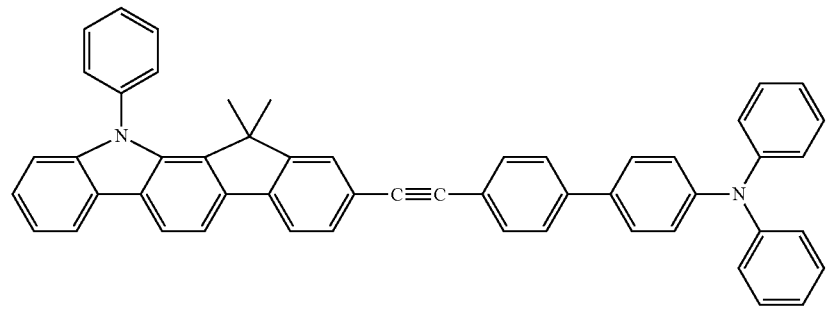
29
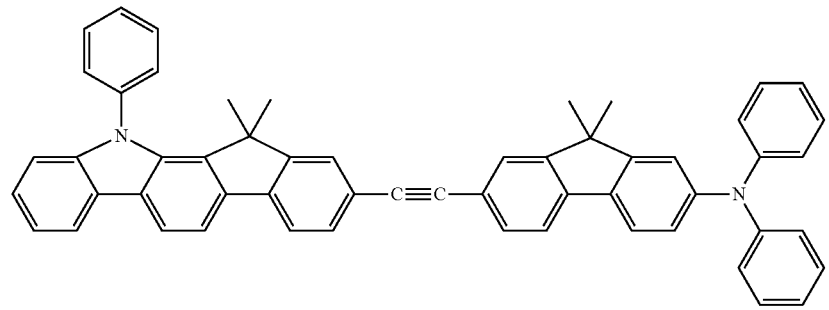
30
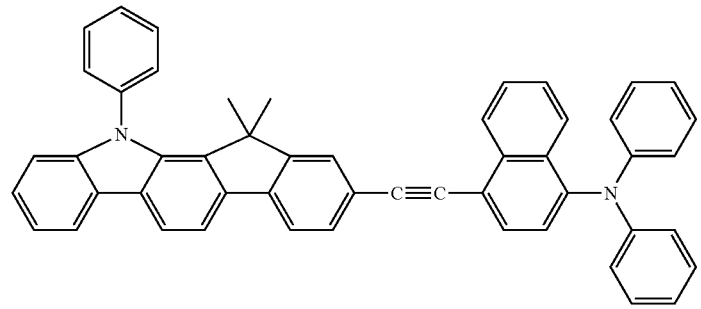
31

-continued
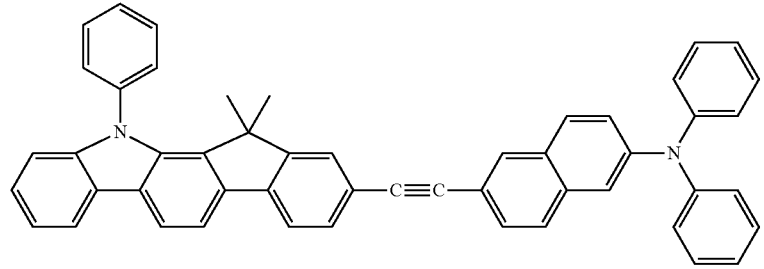
32
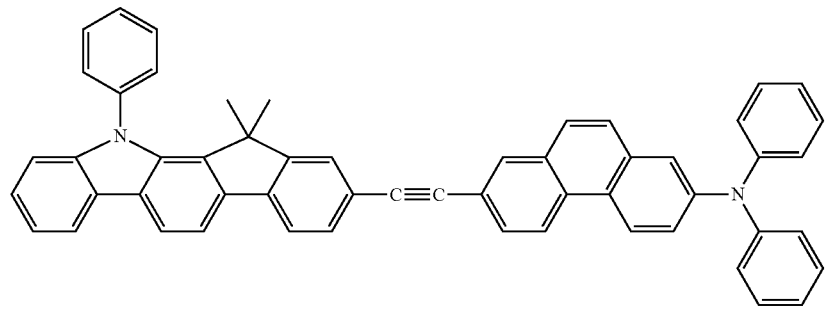
33
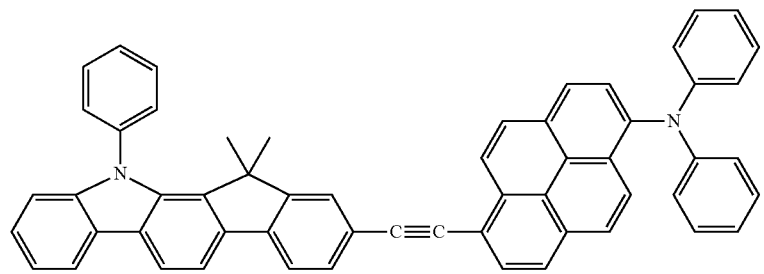
34
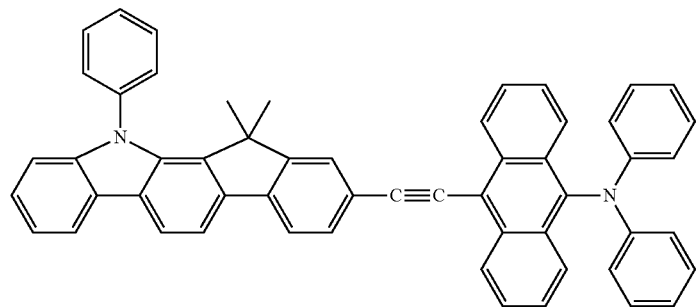
35
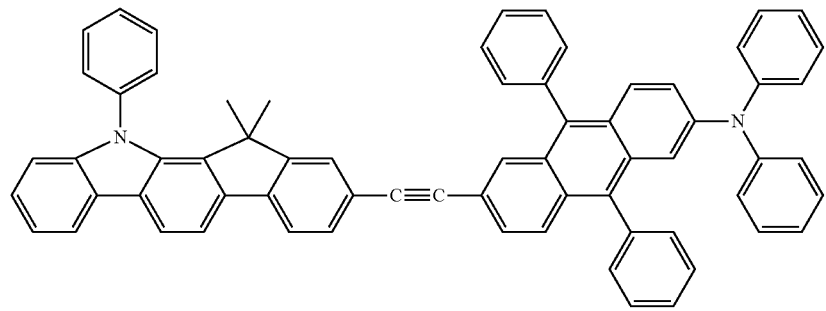
36

37
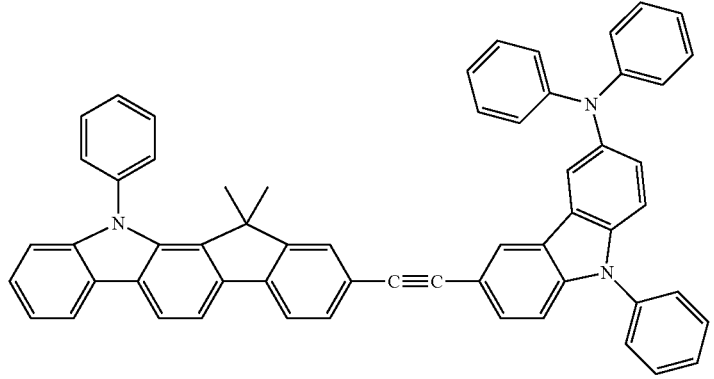
38
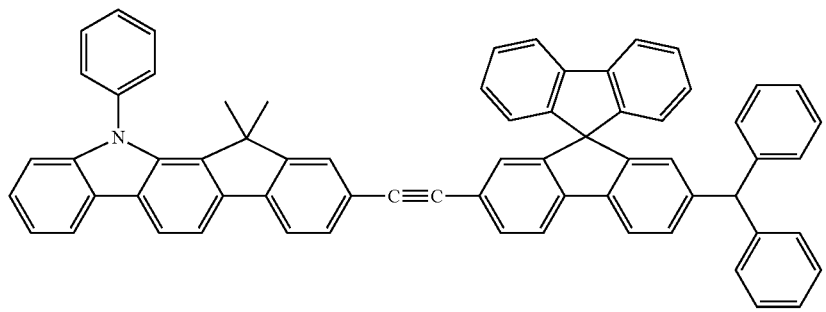
39
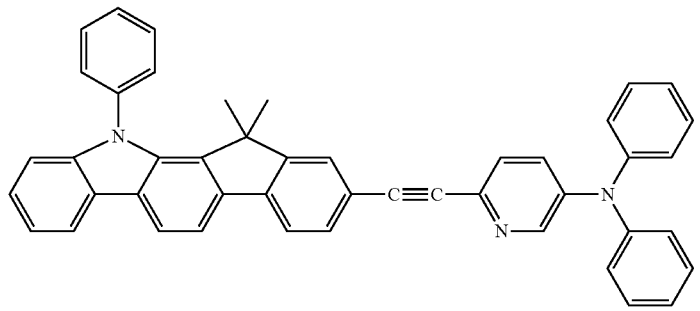
40
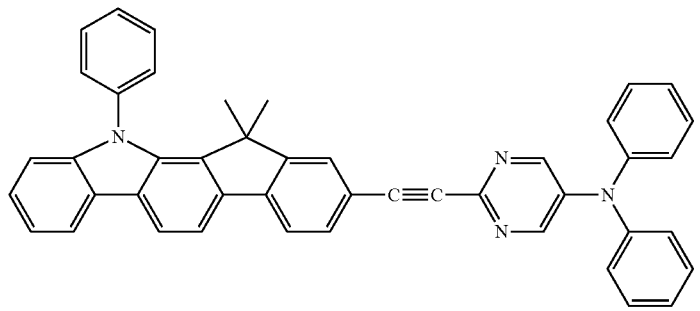
41
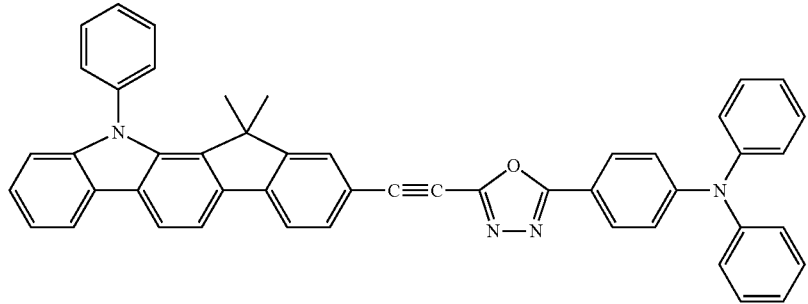

42
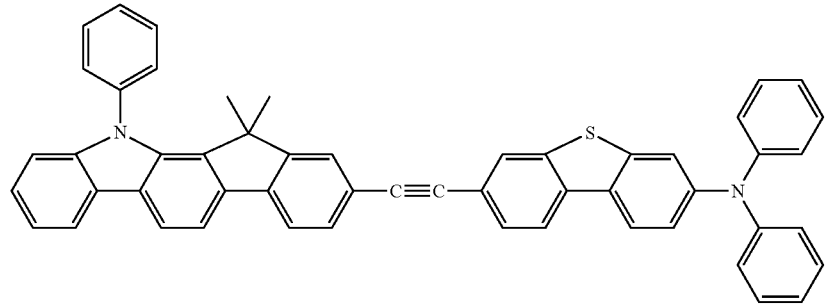
43
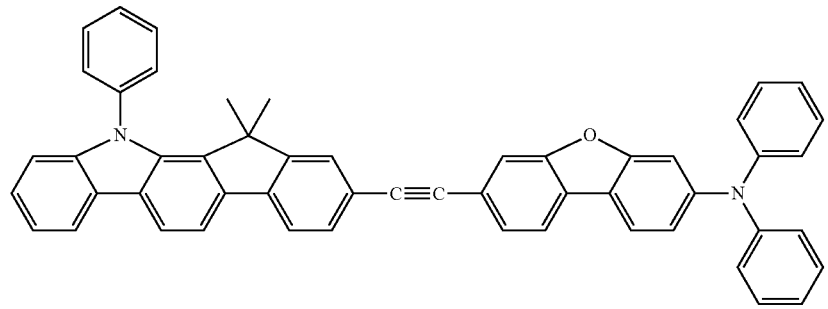
44
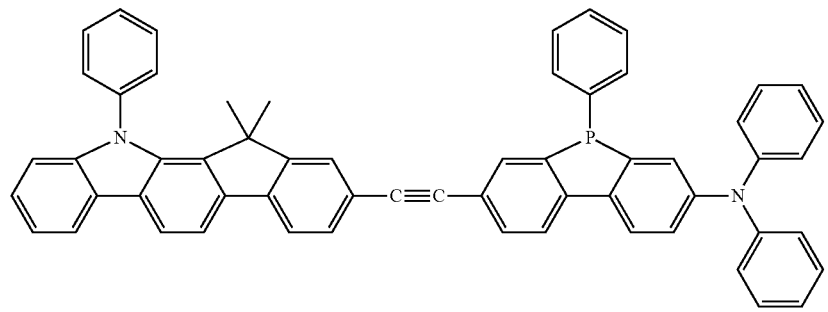
45
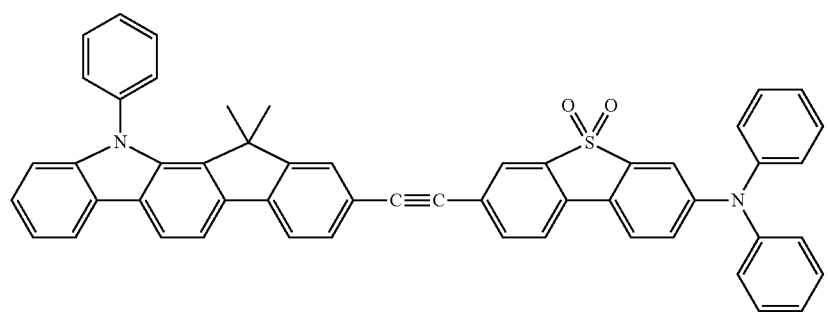
46
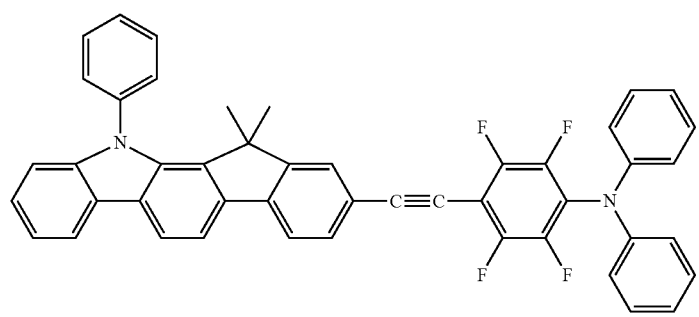

47
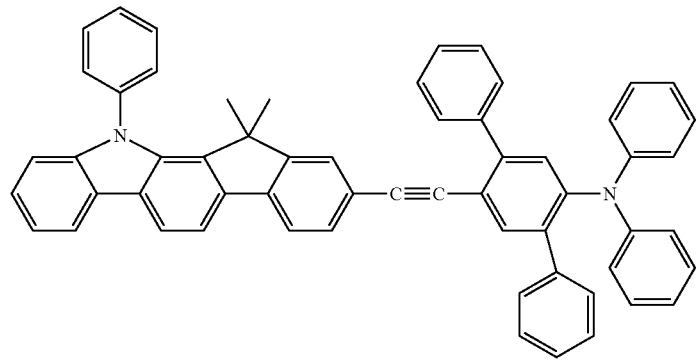
48
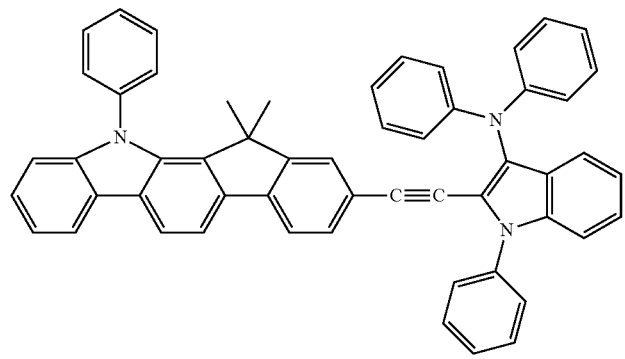
49
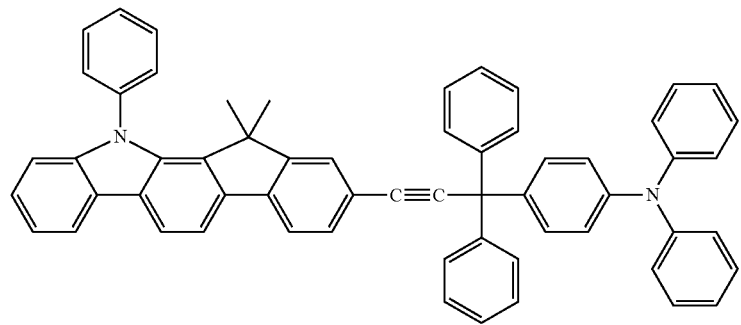
50
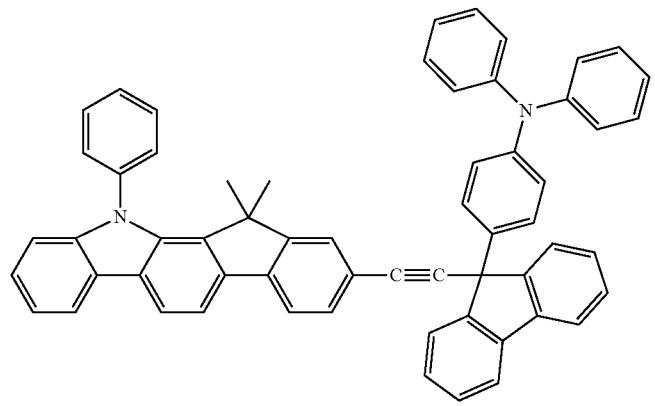

-continued
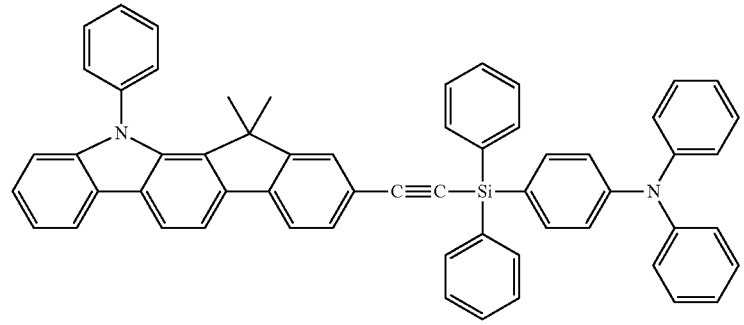
51
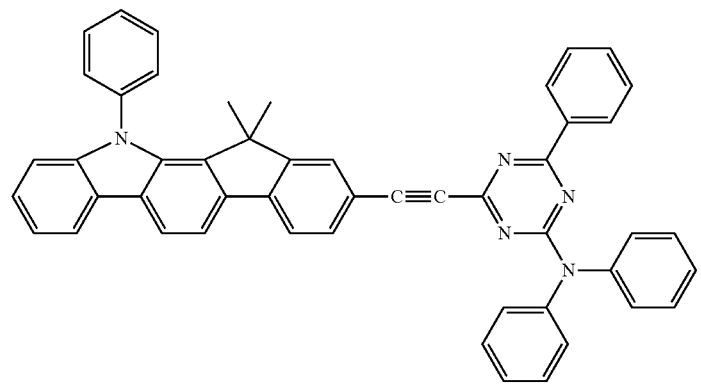
52
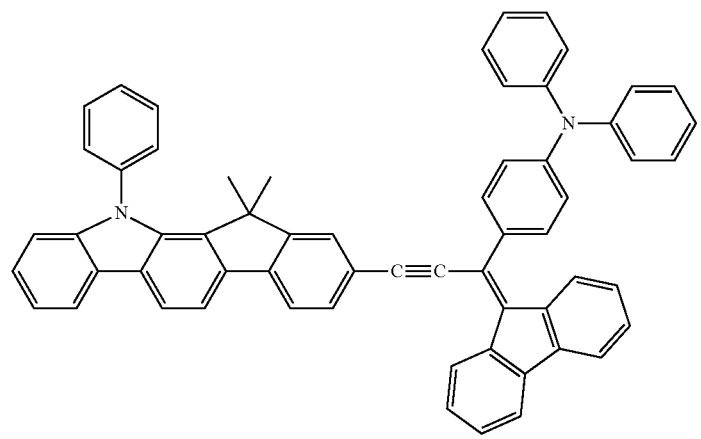
53
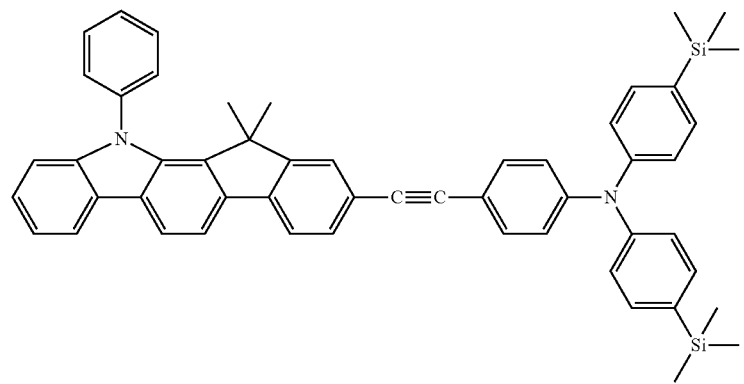
54

55
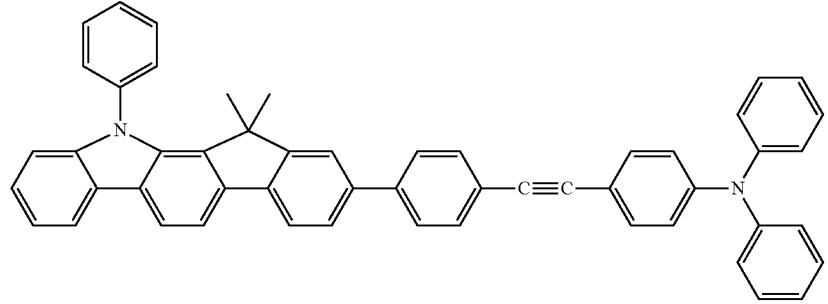
56
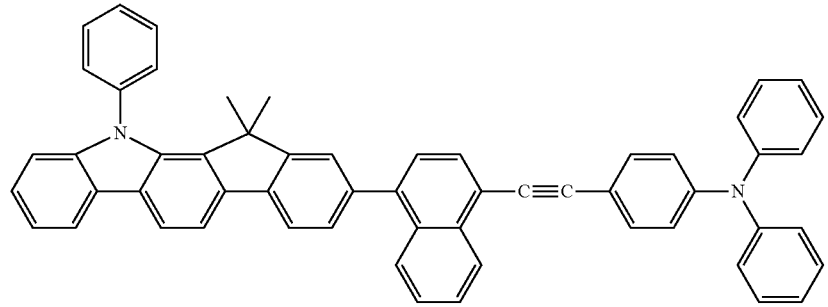
57
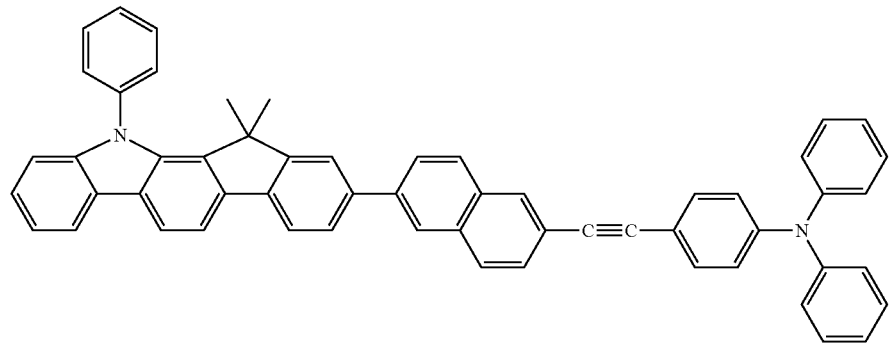
58
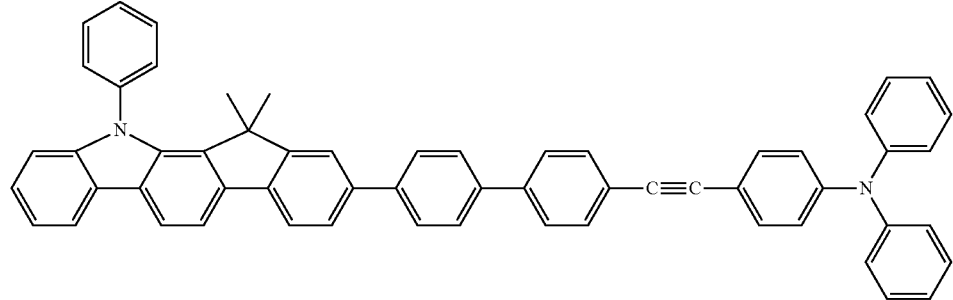
59
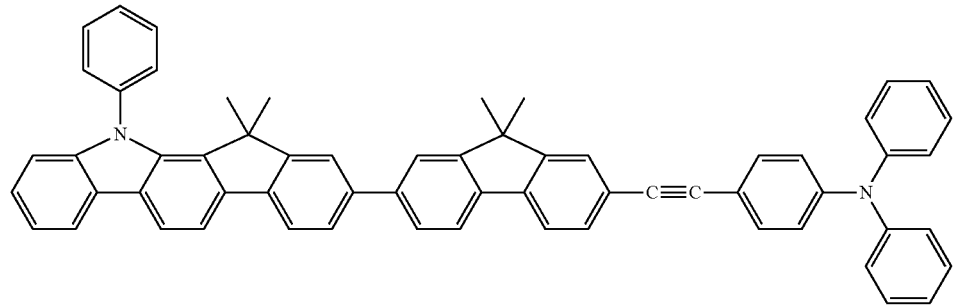

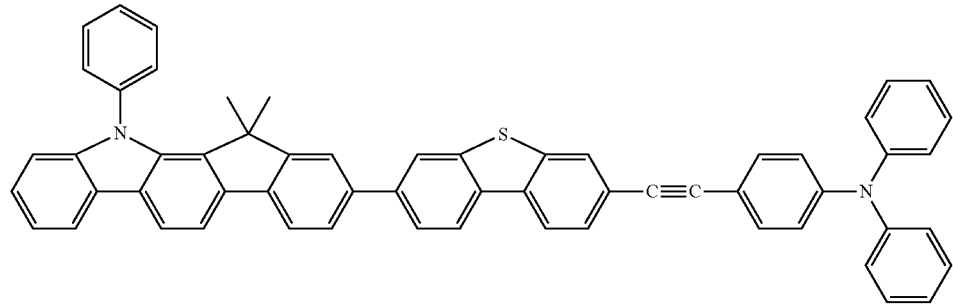
60
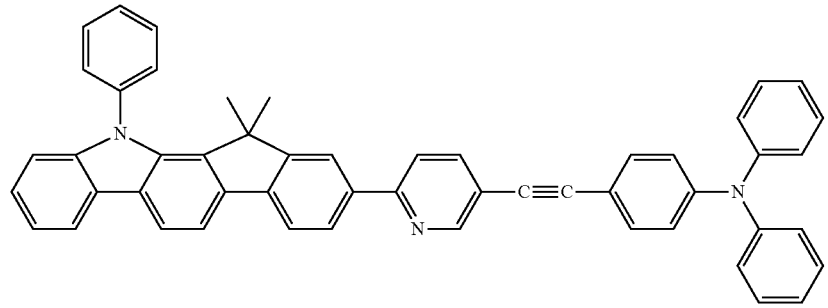
61
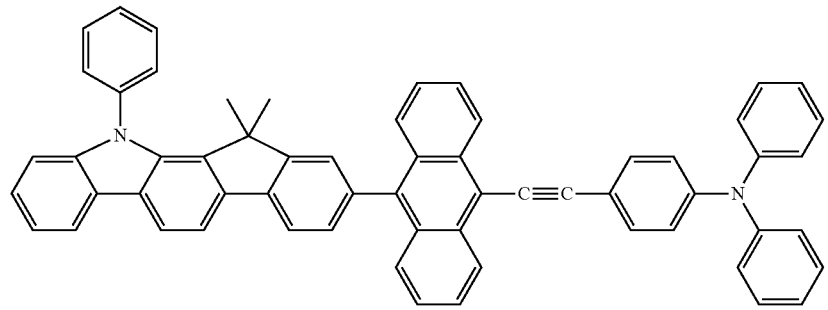
62
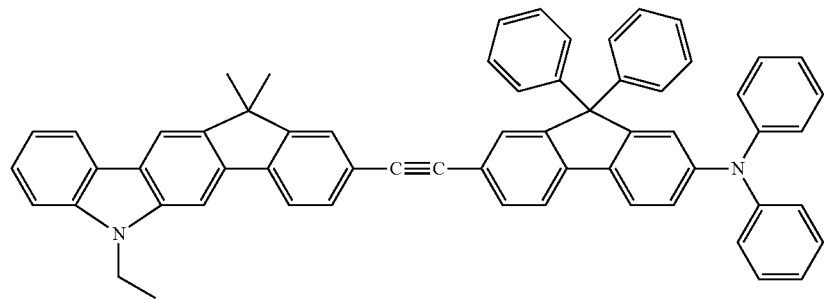
63
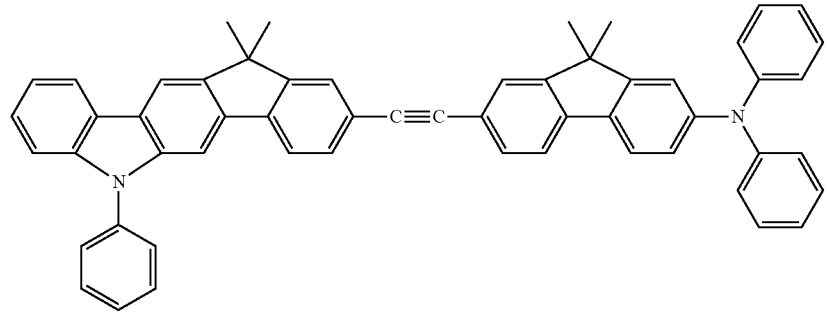
64

65
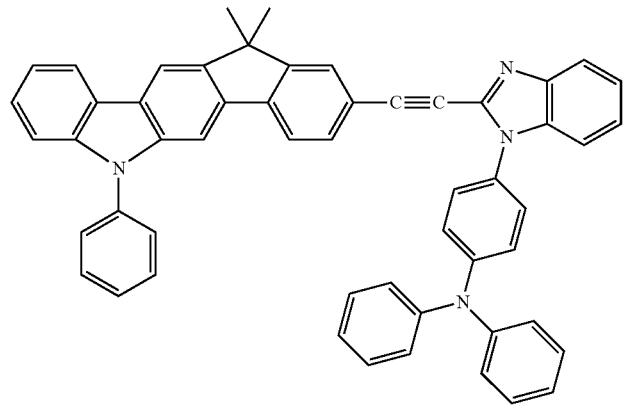
66
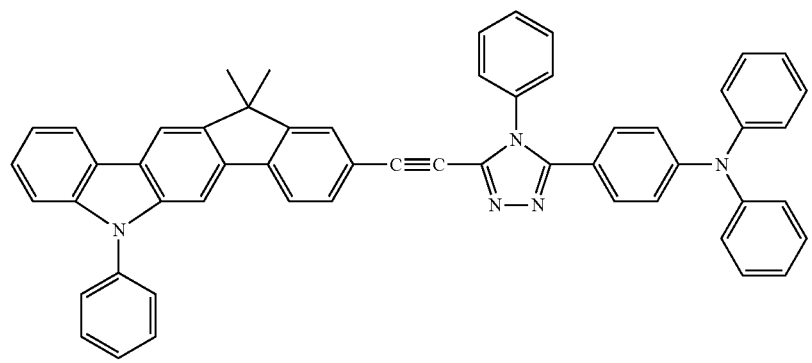
67
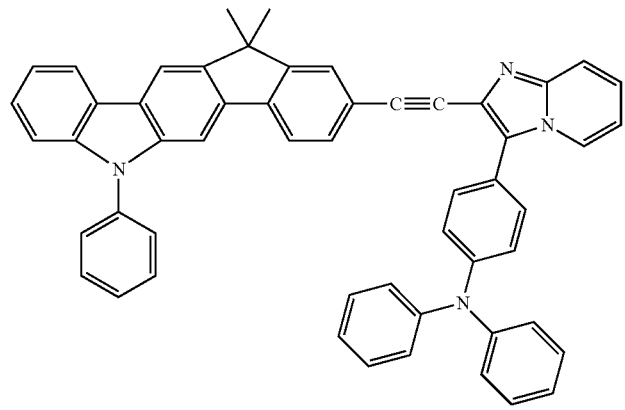
68
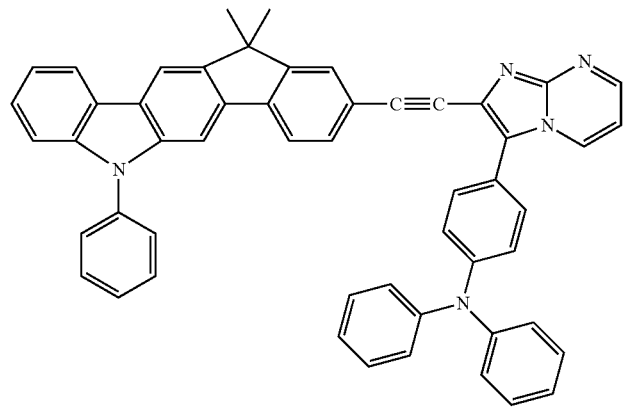

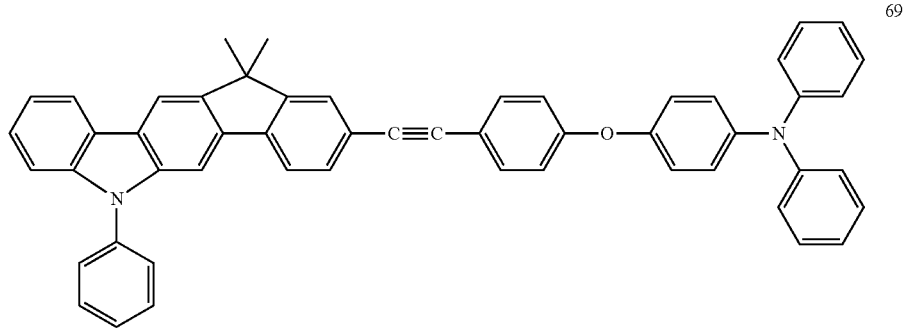
69
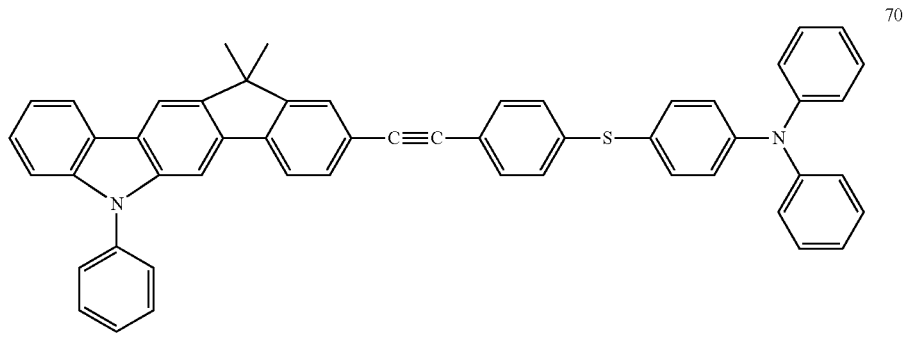
70
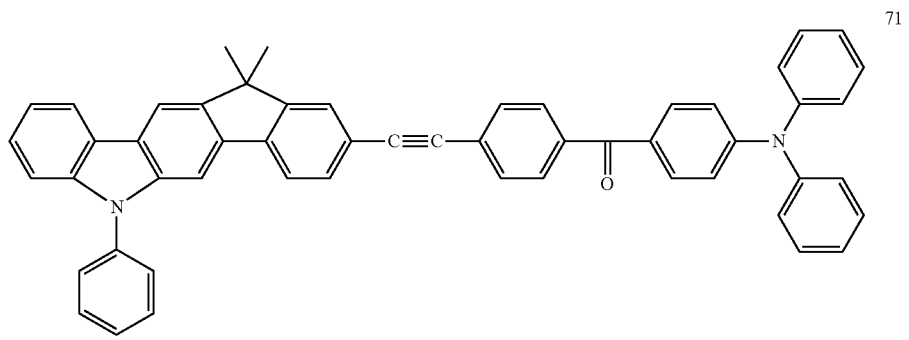
71
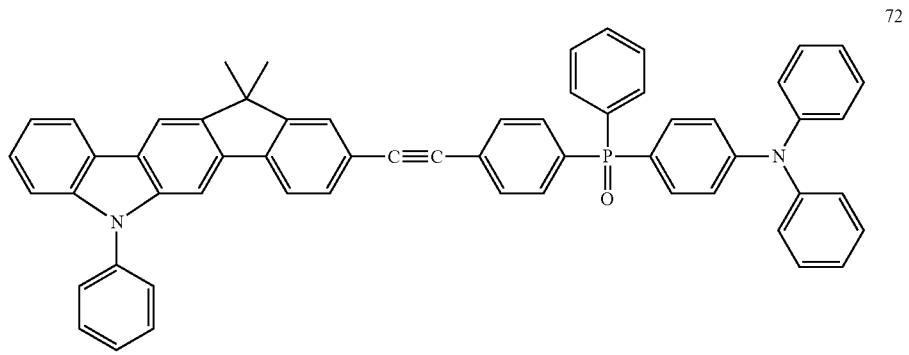
72
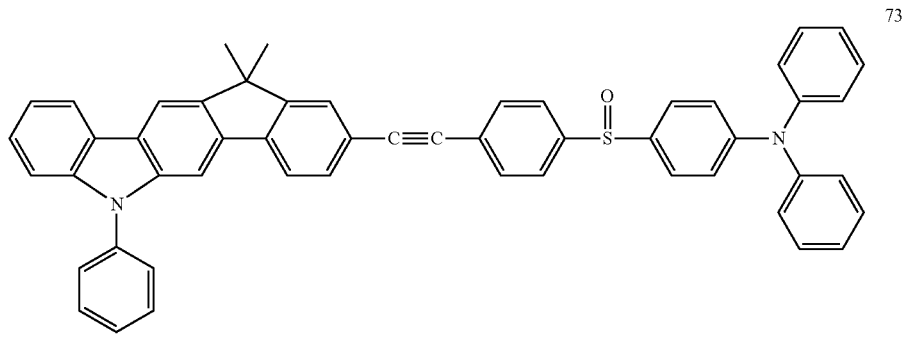
73

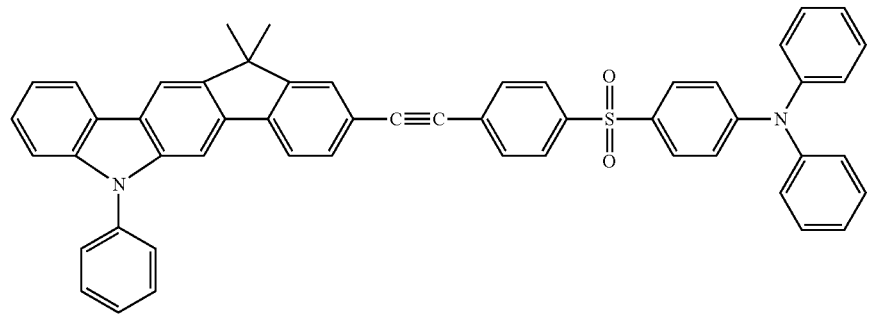
74
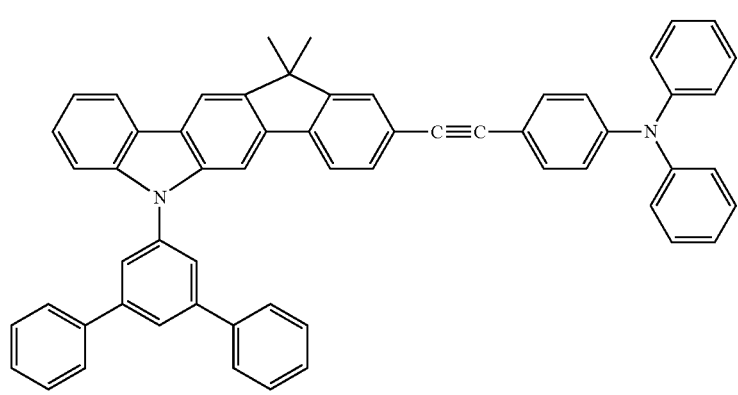
75
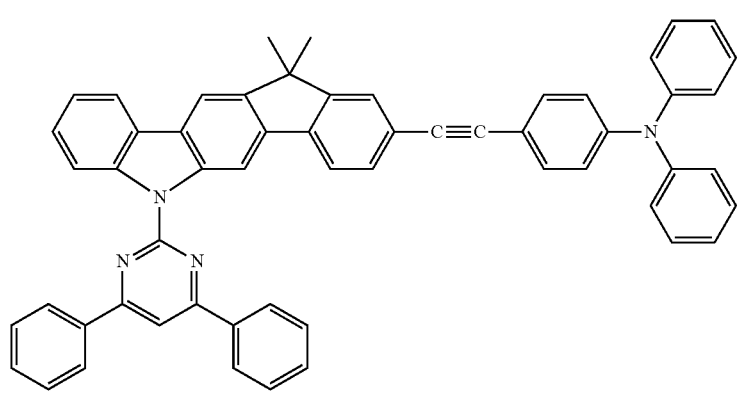
76
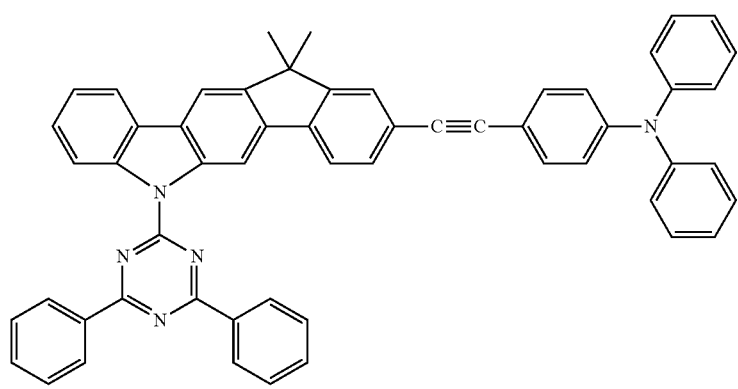
77

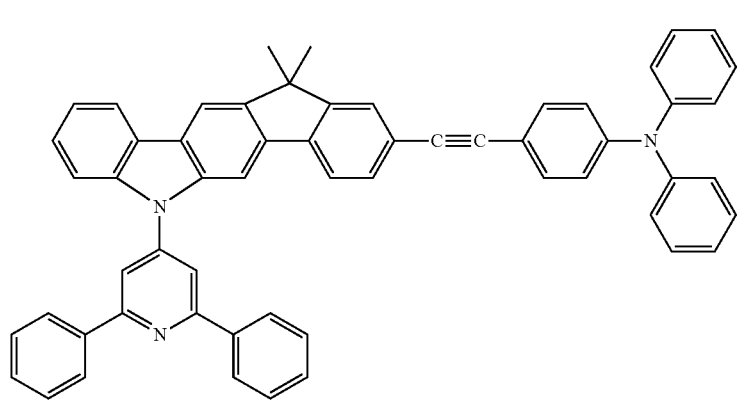
78
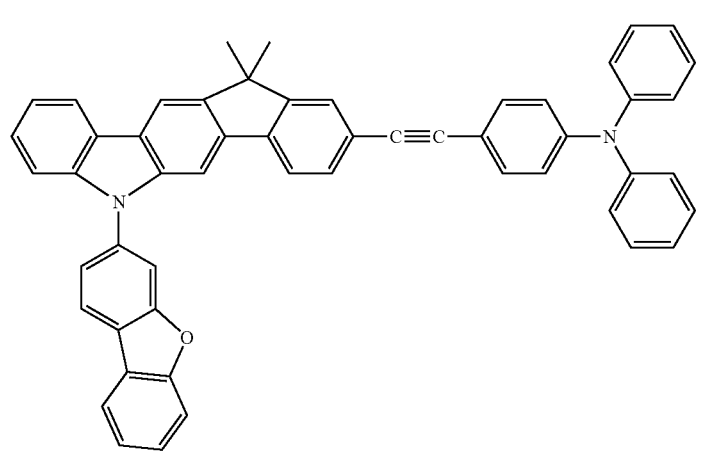
79
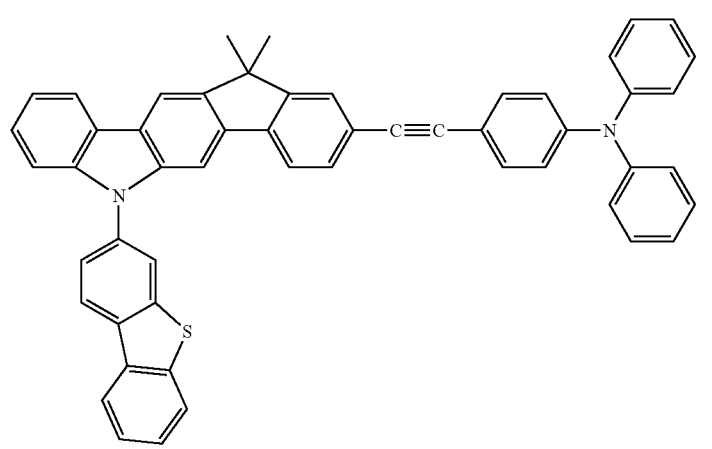
80

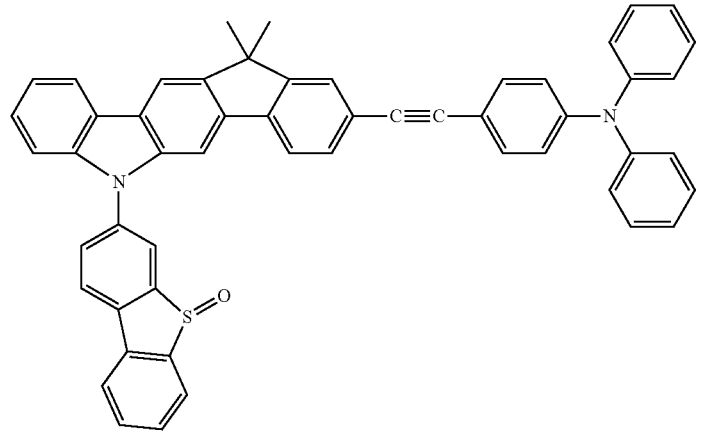
81
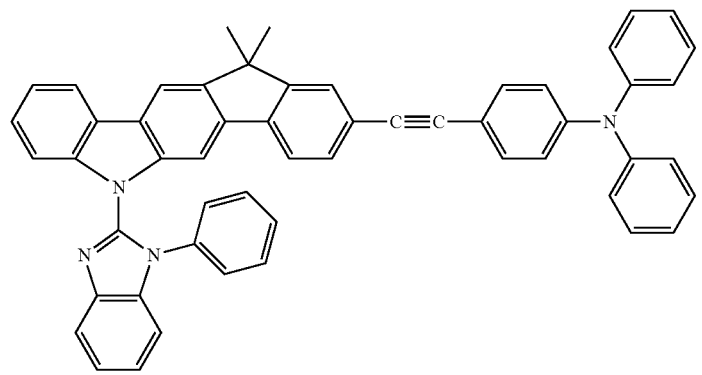
82
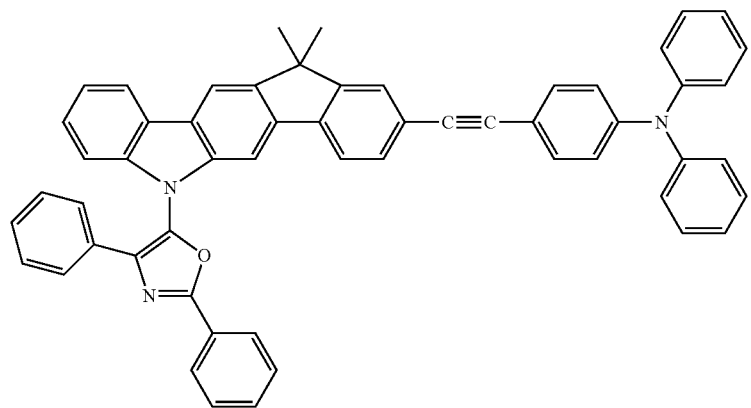
83
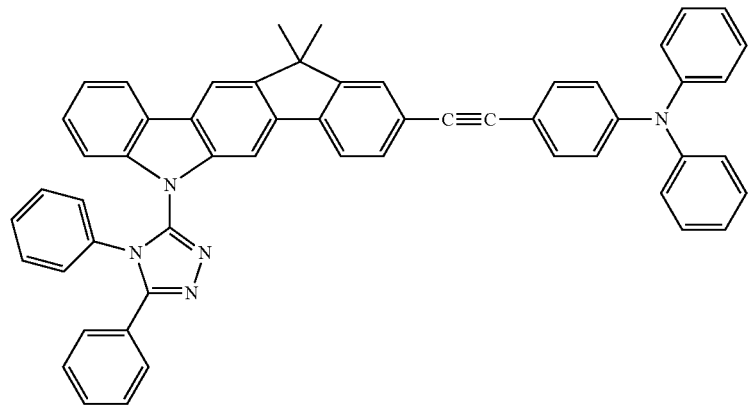
84

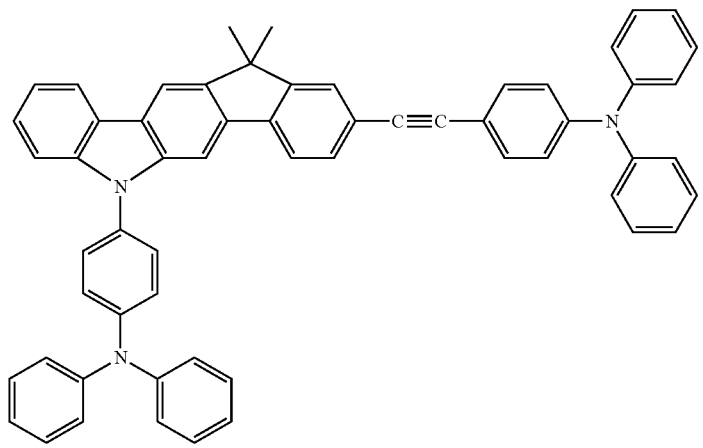
85
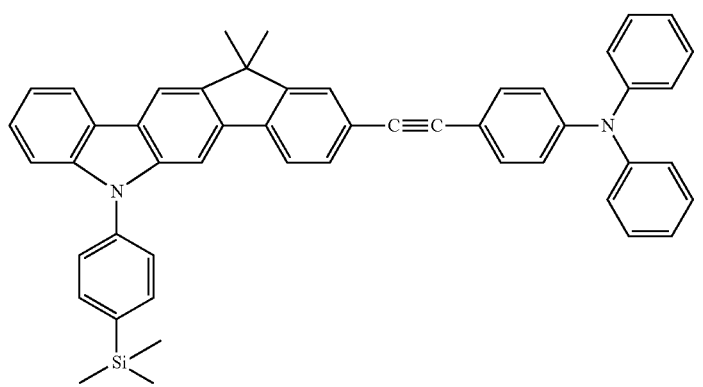
86
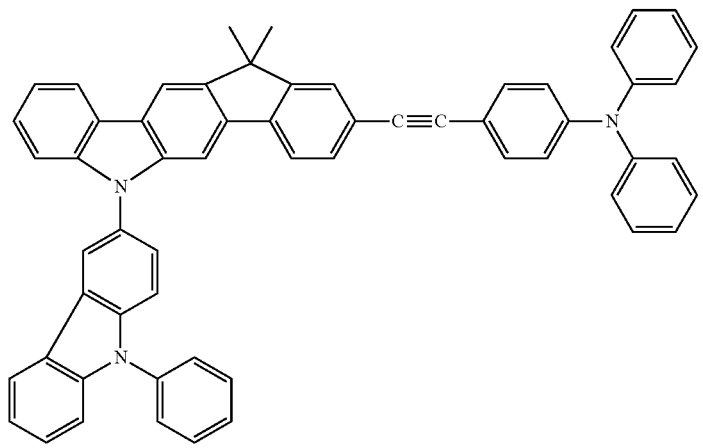
87

-continued
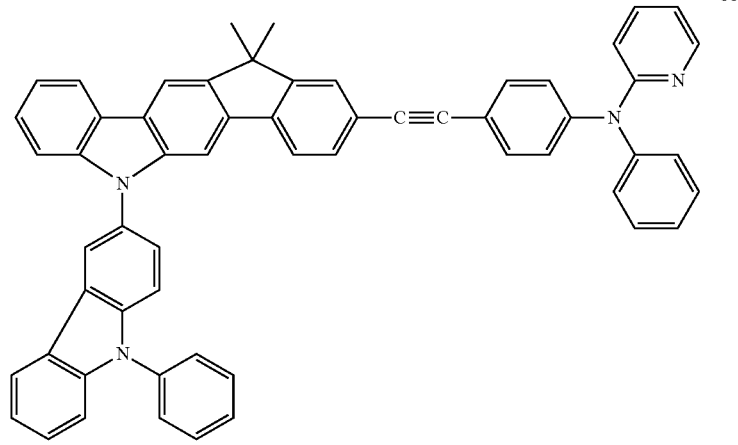
88
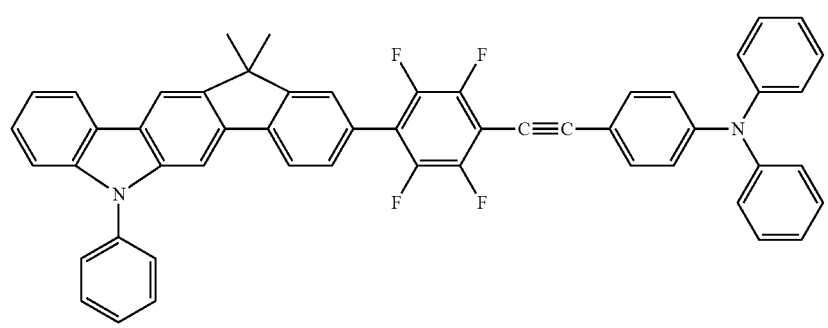
89
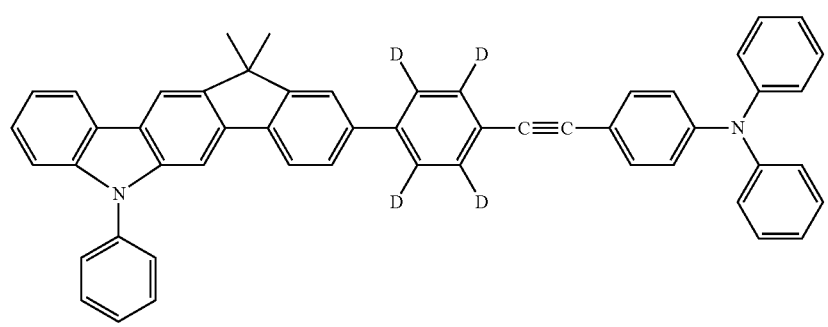
90
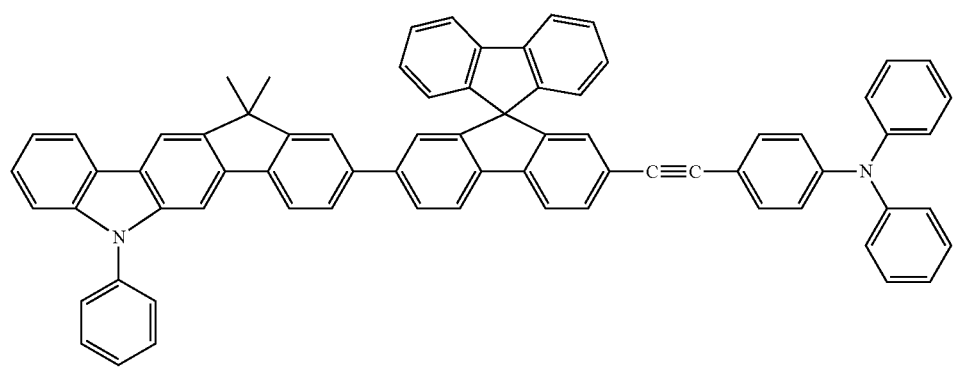
91

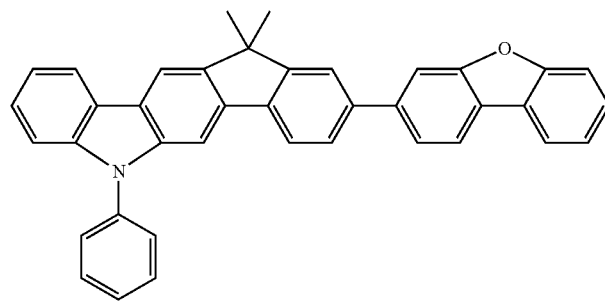 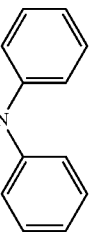

The heterocyclic compound of Formula 1 or Formula 2 may be used as an emitting material, a hole injecting material, and/or a hole transporting material of an organic light-emitting device. The heterocyclic compound of Formula 1 or Formula 2, which has a heterocyclic group in the molecules thereof, has a high glass transition temperature (Tg) or a high melting point due to the inclusion of the heterocyclic group. Thus, the heterocyclic compound has high heat resistance against Joule's heat generated in an organic layer, between organic layers, or between an organic layer and a metal electrode when light emission occurs, and has high durability in high-temperature environments. When a substituent such as a fluorenyl group is introduced, the heterocyclic compound of Formula 1 or Formula 2 may improve morphology of the organic layer, thus improving characteristics of an organic light-emitting device.

As used herein, the term "substituted A" of the "substituted or unsubstituted A (wherein A is an arbitrary substituent)" refers to a group A of which at least one hydrogen atom is substituted with one of a deuterium atom, a halogen atom, a hydroxyl group, a cyano group, a nitro group, an amino group, hydrazine, hydrazone, a carboxyl group or a salt derivative thereof, a sulfonic acid group or a salt derivative thereof, a phosphoric acid group or a salt derivative thereof, a $C_1$-$C_{30}$ alkyl group, a $C_2$-$C_{30}$ alkenyl group, a $C_2$-$C_{30}$ alkynyl group, a $C_1$-$C_{30}$ alkoxy group, a $C_3$-$C_{30}$ cycloalkyl group, a $C_3$-$C_{30}$ cycloalkenyl group, a $C_5$-$C_{30}$ aryl group, a $C_5$-$C_{30}$ aryloxy group, a $C_5$-$C_{30}$ arylthio group, a $C_3$-$C_{30}$ heteroaryl group, a group represented by $N(Q_{101})(Q_{102})$, and a group represented by $Si(Q_{103})(Q_{104})(Q_{105})$, wherein $Q_{101}$ to $Q_{105}$ may be each independently one of a hydrogen atom, a deuterium atom, a halogen atom, a hydroxyl group, a cyano group, an amino group, a nitro group, a carboxyl group, a $C_1$-$C_{30}$ alkyl group, a $C_2$-$C_{30}$ alkenyl group, a $C_2$-$C_{30}$ alkynyl group, a $C_1$-$C_{30}$ alkoxy group, a $C_3$-$C_{30}$ cycloalkyl group, a $C_3$-$C_{30}$ cycloalkenyl group, a $C_5$-$C_{30}$ aryl group, a $C_5$-$C_{30}$ aryloxy group, a $C_5$-$C_{30}$ arylthio group, and a $C_3$-$C_{30}$ heteroaryl group.

For example, the term "substituted A" may refer to a group A of which at least one hydrogen atom is substituted with one of a deuterium atom, a halogen atom, a hydroxyl group, a cyano group, a nitro group, a carboxyl group, a methyl group an ethyl group, a propyl group, a butyl group, a pentyl group, a methoxy group, an ethoxy group, a phenyl group, a biphenyl group, a pentalenyl group, an indenyl group, a naphthyl group, an azulenyl group, a heptalenyl group, an indacenyl group, an acenaphthyl group, a fluorenyl group, a spirofluorenyl group, a phenalenyl group, a phenanthrenyl group, a phenantridinyl group, a phenanthrolinyl group, an anthryl group, a fluoranthenyl group, a triphenyllenyl group, a pyrenyl group, a chrycenyl group, a naphthacenyl group, a picenyl group, a perylenyl group, a pentaphenyl group, a hexacenyl group, a pyrrolyl group, an imidazolyl group, a benzoimidazolyl group, a pyrazolyl group, a pyridinyl group, a pyrazinyl group, a pyrimidinyl group, an imidazopyrimidinyl group, a pyridazinyl group, an indolyl group, an isoindolyl group, a pyridoindolyl group, an indazolyl group, a furinyl group, a quinolinyl group, a benzoquinolinyl group, a phthalazinyl group, a phthalazinyl v quinoxalinyl group, a quinazolinyl group, a carbazolyl group, a phenazinyl group, a furanyl group, a benzofuranyl group, a dibenzofuranyl group, a thiophenyl group, a benzothiophenyl group, a dibenzothiophenyl group, a thiazolyl group, an isothiazolyl group, a benzothiazolyl group, an oxazolyl v benzooxazolyl group, an isoazolyl group, an oxadiazolyl group, a traixolyl group, a triazinyl group, a tetrazolyl group, a represented by $N(Q_{101})(Q_{102})$, and a group represented by $Si(Q_{103})(Q_{104})(Q_{105})$.

As used herein, the unsubstituted $C_1$-$C_{30}$ alkyl group refers to a linear or branched saturated hydrocarbon that lacks one hydrogen atom from alkane. Non-limiting examples of the unsubstituted $C_1$-$C_{30}$ alkyl group include methyl, ethyl, propyl, isobutyl, sec-butyl, pentyl, isoamyl, and hexyl. Substituents of the substituted $C_1$-$C_{30}$ alkyl group are the same as described above in conjunction with the "substituted A".

As used herein, the unsubstituted $C_1$-$C_{30}$ alkenyl group indicates a hydrocarbon chain having at least one carbon-carbon double bond in the center or at a terminal of the unsubstituted $C_2$-$C_{30}$ alkyl group. Non-limiting examples of the unsubstituted $C_2$-$C_{30}$ alkenyl group include ethenyl, propenyl, butenyl, pentenyl, hexenyl, heptenyl, octenyl, propadienyl, isoprenyl, and allyl. Substituents or the substituted $C_2$-$C_{30}$ alkenyl group are the same as described above in conjunction with the "substituted A".

As used herein, the unsubstituted $C_2$-$C_{30}$ alkynyl group indicates a hydrocarbon chain having at least one carbon-carbon triple bond in the center or at a terminal of the unsubstituted $C_2$-$C_{60}$ alkyl group. Non-limiting examples of the unsubstituted $C_2$-$C_{30}$ alkynyl group include ethynyl, propynyl, and acetylenyl. Substituents of the substituted $C_2$-$C_{30}$ alkynyl group are the same as described above in conjunction with the "substituted A".

As used herein, the unsubstituted $C_1$-$C_{30}$ alkoxy group refers to a group represented by —OY, wherein Y is an unsubstituted $C_1$-$C_{30}$ alkyl group as described above. Examples of the unsubstituted $C_1$-$C_{30}$ alkoxy group include a methoxy group, an ethoxy group, an isopropyloxy group, a butoxy group, and a pentoxy group. Substituents of the substituted $C_1$-$C_{30}$ alkoxy group are the same as described above in conjunction with the "substituted A".

As used herein, the unsubstituted $C_3$-$C_{30}$ cycloalkyl group indicates a cyclic saturated hydrocarbon group. Non-limiting examples of the unsubstituted $C_3$-$C_{30}$ cycloalkyl group include cyclopropyl, cyclobutyl, cyclopentyl, cyclohexyl, and cyclooctyl. Substituents of the substituted $C_3-C_{30}$ cycloalkyl group are the same as described above in conjunction with the "substituted A".

As used herein, the unsubstituted $C_5-C_{30}$ cycloalkenyl group refers to a cyclic unsaturated hydrocarbon group with at least one carbon-carbon double bond. Non-limiting examples of the unsubstituted $C_3-C_{30}$ cycloalkenyl group include cyclopropenyl, cyclobutenyl, cyclopentenyl, cyclohexenyl, cycloheptenyl, 1,3-cyclohexadienyl, 1,4-cyclohexadienyl, 2,4-cycloheptadienyl, and 1,5-cyclooctadienyloctenyl. Substituents of the substituted $C_3-C_{60}$ cycloalkenyl group are the same as described above in conjunction with the "substituted A".

As used herein, the unsubstituted $C_5-C_{30}$ aryl group indicates a monovalent group including a $C_5-C_{30}$ carbocyclic aromatic system, which may be monocyclic or polycyclic. In a polycyclic group, at least two rings may be fused to each other. Non-limiting examples of the unsubstituted $C_5-C_{30}$ aryl group include phenyl, pentalenyl, indenyl, naphthyl, azulenyl, heptalenyl, indacenyl, acenaphthyl, fluorenyl, spirofluorenyl, phenalenyl, phenanthrenyl, anthryl, fluoranthenyl, triphenylenyl, pyrenyl, chrysenyl, naphthacenyl, picenyl, perylenyl, pentaphenyl, and hexacenyl. Substituents of the substituted $C_5-C_{30}$ aryl group are the same as described above in conjunction with the "substituted A".

As used herein, the unsubstituted $C_5-C_{30}$ aryloxy group refers to a monovalent group with a carbon atom of the $C_5-C_{30}$ aryl group attached via an oxygen linker (—O—). Substituents of the substituted $C_5-C_{30}$ aryloxy group are the same as described above in conjunction with the "substituted A".

As used herein, the unsubstituted $C_5-C_{30}$ arylthio group refers to a monovalent group with a carbon atom of the $C_5-C_{30}$ aryl group attached via a sulfur linker (—S—). Non-limiting examples of the unsubstituted $C_5-C_{30}$ arylthio group include a phenylthio group, a naphthylthio group, an indanylthio group, and an indenylthio group. Substituents of the substituted $C_5-C_{30}$ arylthio group are the same as described above in conjunction with the "substituted A".

As used herein, the unsubstituted $C_3-C_{30}$ heteroaryl group indicates a monovalent group with at least one ring including at least one heteroatom selected from among N, O, P, and S, which may be a monocyclic or polycyclic group. In a polycyclic group, at least two rings may be fused to each other. Non-limiting examples of the unsubstituted $C_3-C_{30}$ heteroaryl group include pyrrolyl, imidazolyl, pyrazolyl, pyridinyl, pyrazinyl, pyridazinyl, isoindolyl, indolyl, indazolyl, purinyl, quinolinyl, benzoquinolinyl, phthalazinyl, naphthyridinyl, quinoxalinyl, quinazolinyl, cinnolinyl, carbazolyl, phenanthridinyl, acridinyl, phenanthrolinyl, phenazinyl, benzooxazolyl, benzoimidazolyl, furanyl, benzofuranyl, thiophenyl, benzothiophenyl, thiazolyl, isothiazolyl, benzothiazolyl, isoxazolyl, oxazolyl, triazolyl, tetrazolyl, oxadiazolyl, triazinyl, and benzooxazolyl. Substituents of the substituted $C_3-C_{30}$ heteroaryl group are the same as described above in conjunction with the "substituted A".

In the specification, the unsubstituted $C_1-C_{30}$ alkylene group refers to a linear or branched divalent group that lacks two hydrogen atoms from the unsubstituted $C_1-C_{30}$ alkylene group. Examples of the unsubstituted $C_1-C_{30}$ alkylene group may be inferred based on those of the unsubstituted $C_1-C_{30}$ alkyl group described above. Substituents of the substituted $C_1-C_{30}$ alkylene group are the same as those described above in conjunction with the "substituted A".

As used herein, the unsubstituted $C_5-C_{30}$arylene group indicates a divalent group including a $C_5-C_{30}$ carbocyclic aromatic system, which may be monocyclic or polycyclic. Examples of the unsubstituted $C_5-C_{30}$arylene group may be inferred based on those of the unsubstituted $C_5-C_{30}$ aryl group described above. Substituents of the substituted $C_5-C_{30}$ arylene group are the same as those described above in conjunction with the "substituted A".

The heterocyclic compound of Formula 1 or Formula 2 may be synthesized using a common organic synthesis method. A synthesis method of the heterocyclic compound of Formula 1 or Formula 2 may be understood by those of ordinary skill in the art from the examples that will be described below.

The heterocyclic compound of Formula 1 or Formula 2 may be used in an organic light-emitting device.

According to another aspect of the present invention, an organic light-emitting device includes: a first electrode; a second electrode disposed opposite to the first electrode; and an organic layer disposed between the first electrode and the second electrode. The organic layer, including at least one layer, may contain at least one of the heterocyclic compounds represented by Formulae 1 and 2 described above.

As used herein, the term "organic layer" refers to a layer containing an organic compound and comprising at least one layer. For example, the organic layer may include at least one layer selected from the group consisting of a hole injection layer, a hole transport layer, a hole injection and transport layer having both hole injection and hole transport capabilities, an electron blocking layer, an emission layer, a hole blocking layer, an electron injection layer, an electron transport layer, and an electron injection and transport layer having both electron injection and electron transport capabilities. The organic layer may not include solely an organic compound. The organic layer may include an inorganic compound or an inorganic material. In one embodiment of the present invention, the organic layer may include both an organic compound and an inorganic compound or an inorganic material in one layer. For example, the organic layer may include both an organic compound and an organometallic complex in one layer. In another embodiment of the present invention, the organic layer may include a layer containing an organic compound and another layer containing an inorganic compound or an inorganic material.

The organic layer may include at least one of the heterocyclic compounds listed above in one layer, and in some other embodiments, the organic layer may include at least one of the heterocyclic compounds listed above in layers. For example, the organic layer may include one of the heterocyclic compounds listed above as an emitting dopant in an emission layer, and another heterocyclic compound listed above as a hole transport material in a hole transport layer. In another embodiment of the present invention, the organic layer may include one of the heterocyclic compounds listed above as an emitting dopant and another heterocyclic compound listed above as an emitting host in an emission layer. In another embodiment of the present invention, the organic layer may include one of the heterocyclic compounds listed above as an emitting dopant and another heterocyclic compound listed above as an emitting host in an emission layer, and still another heterocyclic compound listed above as a hole transport material in a hole transport layer.

The organic layer may include at least one of an emission layer, a hole injection layer, a hole transport layer, and a hole injection and transport layer having both hole injection and hole transport capabilities, and at least one of the emission layer, the hole injection layer, the hole transport layer, and the hole injection and transport layer may include the heterocyclic compounds listed above.

In some embodiments of the present invention, the organic light-emitting device may have a first electrode/hole injection layer/hole transport layer/emission layer/electron transport layer/second electrode structure, wherein the emission layer, the hole transport layer, or the hole injection layer may include the heterocyclic compounds listed above. In other embodiments of the present invention, at least two layers of the emission layer, the hole transport layer, and the hole injection layer may include the heterocyclic compounds listed above. In these embodiments, each layer of the at least two layers may include a different heterocyclic compound listed above. As described above, each layer in the organic layer may include a mixture of at least two of the heterocyclic compounds listed above, or a mixture of one of the heterocyclic compounds listed above and a non-heterocyclic compound.

In some embodiments of the present invention, the organic layer may include an emission layer, which may include a host and a dopant, and the heterocyclic compound may be a fluorescent host, a phosphorescent host, or a fluorescent dopant of the emission layer.

In some embodiments, the organic layer may include an emission layer, which may further include an anthracene compound, an arylamine compound, or a styryl compound. The emission layer may or may not include the heterocyclic compound.

The organic layer may include an emission layer, which may include a host and a dopant. The emission layer may further include a phosphorescent dopant. For example, the phosphorescent dopant may be, but is not limited to, an organometallic complex including at least one of iridium (Ir), platinum (Pt), osmium (Os), rhenium (Re), titanium (Ti), zirconium (Zr), hafnium (Hf), and a combination of at least two thereof. The emission layer may or may not include the heterocyclic compound.

At least one layer of the hole injection layer, the hole transport layer, and the hole injection and transport layer may further include a charge generating material, in addition to the heterocyclic compound. The charge generating material may be, for example, a p-type dopant. The hole injection layer, the hole transport layer, and the hole injection and transport layer may or may not include the heterocyclic compound.

The organic layer may further include an electron transport layer, which may include an electron transporting organic compound and a metal-containing material. The metal-containing material may include a lithium (Li) complex. The electron transport layer may or may not include the heterocyclic compound.

At least one organic layer disposed between the first electrode and the second electrode may be formed using deposition or a wet process.

As used herein, the term "wet process" refers to a process involving applying a mixture of a material and a solvent to a predetermined substrate, and drying and/or thermally treating to remove at least part of the solvent, thereby forming a layer including the specific material on the substrate.

For example, the organic layer may be formed using a general vacuum deposition method. In some other embodiments, the organic layer may be formed by applying the mixture of the heterocyclic compound and the solvent to a region to form the organic layer (for example, on the hole transport layer) using spin coating, spraying, inkjet printing, dipping, casting, gravure coating, bar coating, roll coating, wire bar coating, screen coating, flexo coating, offset coating, laser transferring, or the like, and drying and/or thermally treating the mixture coating the region to form the organic layer to remove at least part of the solvent.

In another embodiment, the organic layer may be formed using a laser transfer method by which an organic layer is formed on a base film using vacuum deposition or a wet process described above, and then transferred to a region to form the organic layer of an organic light-emitting device (for example, on the hole transport layer of the organic light-emitting device) using laser.

FIG. 1 is a schematic sectional view of an organic light-emitting device 10 according to an embodiment of the present invention. Hereinafter, a structure of an organic light-emitting device according to an embodiment of the present invention and a method of manufacturing the same will now be described with reference to FIG. 1.

Referring to FIG. 1, the organic light-emitting device 10 according to the present embodiment includes a first electrode 13, an organic layer 15, and a second electrode 17, which are sequentially stacked on a substrate 11 in this order.

The substrate 11 may be any substrate that is used in existing organic light-emitting devices. In some embodiments of the present invention, the substrate 11 may be a glass substrate or a transparent plastic substrate with strong mechanical strength, thermal stability, transparency, a smooth surface, ease of handling, and water resistance.

The first electrode 13 may be formed by depositing or sputtering a first electrode-forming material on the substrate 11. When the first electrode 13 constitutes an anode, a material having a high work function may be used as the first electrode-forming material to facilitate hole injection. The first electrode 13 may be a reflective electrode or a transmission electrode. Suitable first electrode-forming materials include transparent and conductive materials such as ITO, IZO, $SnO_2$, and ZnO. The first electrode 13 may be formed as a reflective electrode using magnesium (Mg), aluminum (Al), aluminum-lithium (Al—Li), calcium (Ca), magnesium-indium (Mg—In), magnesium-silver (Mg—Ag), or the like.

The organic layer 15 may be disposed on the first electrode 13. As described above, the organic layer 15 indicates any layer interposed between the first electrode 13 and, the second electrode 17. The organic layer 15 may not be formed of pure organic materials, and may also include a metal complex.

The organic layer 15 may include a hole injection layer (HIL), a hole transport layer (HTL), an emission layer (EML), an electron transport layer (ETL), and an electron injection layer (EIL).

The HIL may be formed on the first electrode 13 by vacuum deposition, spin coating, casting, Langmuir-Blodgett (LB) deposition, or the like.

When the HIL is formed using vacuum deposition, the vacuum deposition conditions may vary according to the compound that is used to form the HIL and the desired structure and thermal properties of the HIL to be formed. For example, the vacuum deposition may be performed at a temperature of about 100° C. to about 500° C., a pressure of about $10^{-8}$ torr to about $10^{-3}$ torr, and a deposition rate of about 0.01 to about 100 Å/sec. However, the deposition conditions are not limited thereto.

When the HIL is formed using a wet process such as spin coating, the coating conditions may vary according to the compound that is used to form the HIL and the desired structure and thermal properties of the HIL to be formed. For example, the coating rate may be in the range of about 2000 rpm to about 5000 rpm, and a temperature at which heat treatment is performed to remove a solvent after coating may be in the range of about 80° C. to about 200° C. However, the coating conditions are not limited thereto.

The HIL may be formed of the heterocyclic compound represented by Formula 1 or Formula 2 above, or any known materials used to form a HIL. Non-limiting examples of the known hole injection materials include N,N'-diphenyl-N,N'-bis-[4-(phenyl-m-tolyl-amino)-phenyl]-biphenyl-4,4'-diamine (DNTPD), a phthalocyanine compound such as copper phthalocyanine, 4,4',4"-tris (3-methylphenylphenylamino) triphenylamine (m-MTDATA), N,N'-di(1-naphthyl)-N,N'-diphenylbenzidine (NPB), 4,4'4"-Tris(N,N-diphenylamino) triphenylamine (TDATA), 4,4',4'-tris{N,-(2-naphthyl)-N-phenylamino}-triphenylamine (2T-NATA), polyaniline/dodecylbenzenesulfonic acid (PANI/DBSA), poly(3,4-ethylenedioxythiophene)/poly(4-styrenesulfonate) (PEDOT/PSS), polyaniline/camphor sulfonic acid (PANI/CSA), and polyaniline/poly(4-styrenesulfonate) (PANI/PSS).

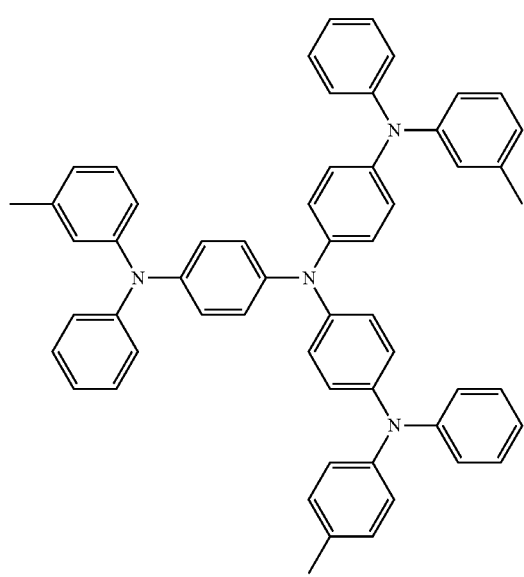

m-MTDATA

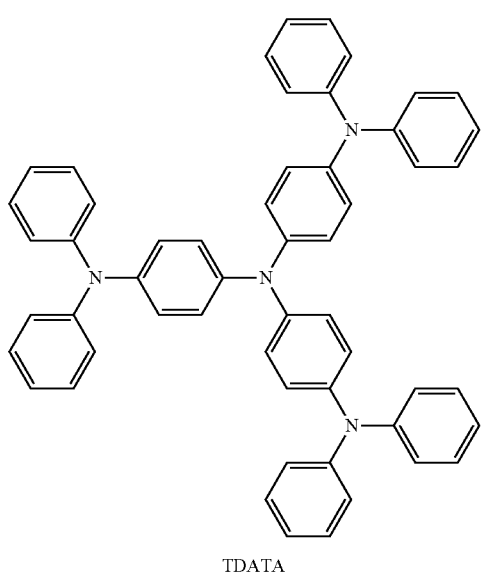

TDATA

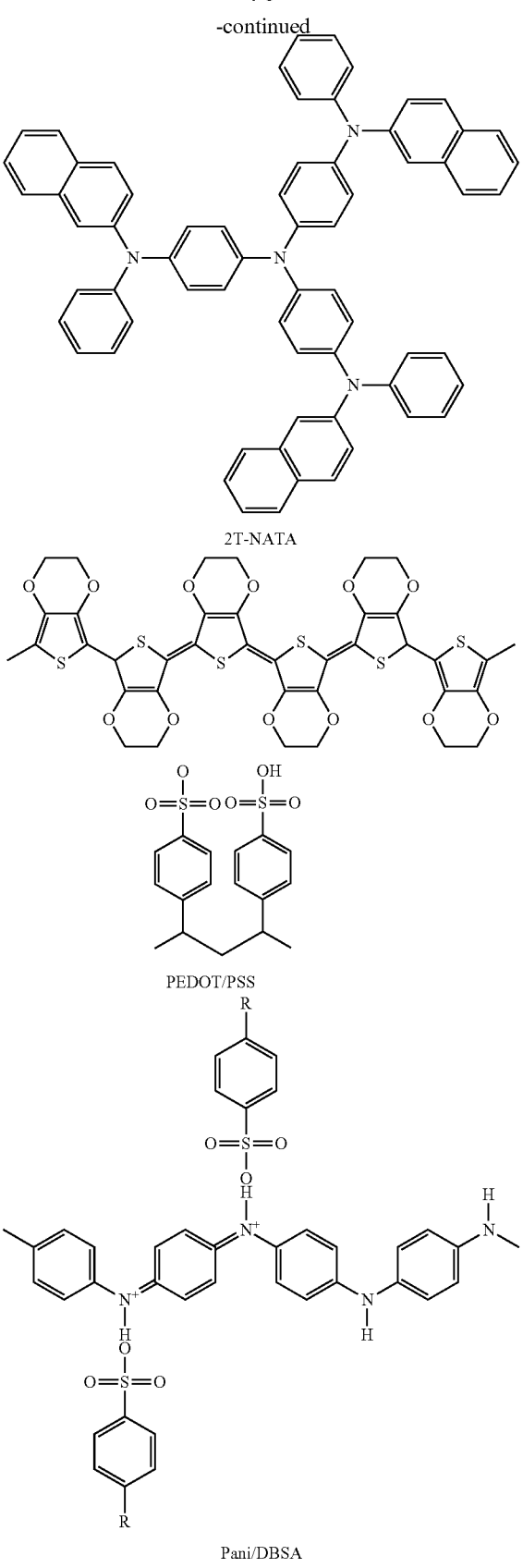

2T-NATA

PEDOT/PSS

Pani/DBSA

The thickness of the HIL may be about 100 Å to about 10000 Å, and in some other embodiments, may be about 100

Å to about 1000 Å. When the thickness of the HIL is within these ranges, the HIL may have good hole injecting ability without a substantial increase in driving voltage.

Then, the HTL may be formed on the HIL by using vacuum deposition, spin coating, casting, LB deposition, or the like. When the HTL is formed using vacuum deposition or spin coating, the conditions for deposition and coating may be similar to those for the formation of the HIL, though the conditions for the deposition and coating may vary according to the material that is used to form the HTL.

The HTL may be formed of the heterocyclic compound represented by Formula 1 or Formula 2 or any known hole transporting materials. Examples of the known hole transporting materials include carbazole derivatives such as N-phenylcarbazole, polyvinylcarbazole, and the like; triphenylamine materials such as TPD (N,N'-bis(3-methylphenyl)-N,N'-diphenyl-[1,1-biphenyl]-4,4'-diamine); and amine derivatives having an aromatic condensed ring, such as α-NPD (4,4'-bis[N-(-naphthyl)-N-phenylamino]biphenyl), TCTA (4,4',4"-tris(N-carbazolyl)triphenylamine), and the like.

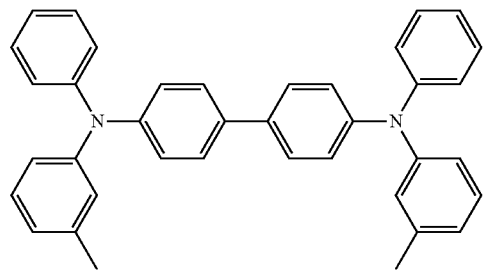

TPD

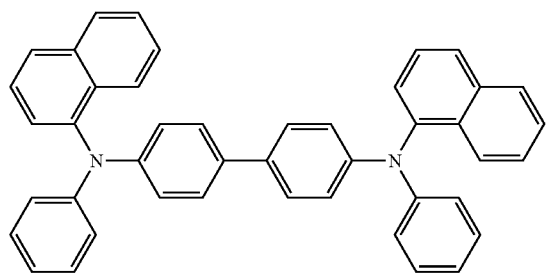

α-NPD

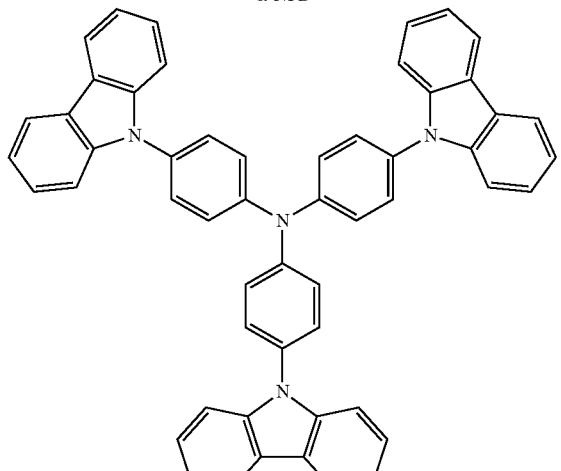

TCTA

The thickness of the HTL may be from about 50 Å to about 1000 Å, and in some embodiments, may be from about 100 Å to about 800 Å. When the thickness of the HTL is within these ranges, the HTL may have good hole transporting ability without a substantial increase in driving voltage.

In some embodiments of the present invention, instead of the HIL and the HTL, a in hole injection and transport layer having both hole injection and hole transport capabilities may be formed. The hole injection and transport layer may be formed using the heterocyclic compound represented by Formula 1 or Formula 2, or any known material.

At least one layer of the hole injection layer, the hole transport layer, and the hole injection and transport layer may further include a charge generating material for improved layer conductivity, in addition to a widely-known hole injection material and a widely-known hole transport material.

The charge generating material may be, for example, a p-type dopant. Non-limiting examples of the p-type dopant include quinone derivatives such as tetracyanoquinodimethane (TCNQ), 2,3,5,6-tetrafluoro-tetracyano-1,4-benzoquinonedimethane (F4TCNQ), and the like; metal oxides such as tungsten oxide, molybdenum oxide, and the like; and cyano-containing compounds such as Compound 100 below:

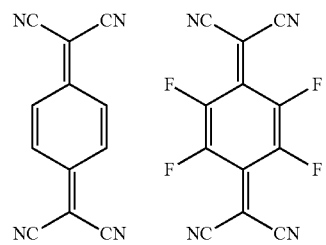

TCNQ        F4TCNQ

Compound 100

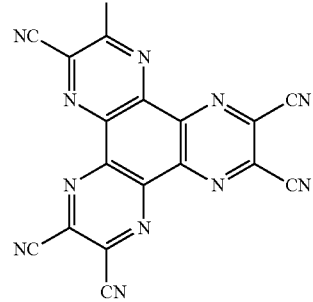

When the hole injection layer, the hole transport layer, or the hole injection and transport layer having both hole injection and hole transport capabilities further includes a charge generating material, the charge generating material may be, but is not limited to being, homogeneously dispersed or inhomogeneously distributed in the layer.

Then, the EML may be formed on the HIL or the hole injection and transport layer having both hole injection and hole transport capabilities by using vacuum deposition, spin coating, casting, LLB deposition, or the like. When the EML is formed using vacuum deposition or spin coating, the deposition and coating conditions may be similar to those for the formation of the HIL, though the conditions for deposition and coating may vary according to the material that is used to form the EML.

The EML may be formed using at least one of the heterocyclic compounds represented by Formula 1 and Formula 2, and known light-emitting materials (including hosts and dopants). When including the heterocyclic compound of Formula 1 or Formula 2, the EML may further include a known phosphorescent host, fluorescent host, phosphorescent dopant, or fluorescent dopant. The heterocyclic compound may also serve as a phosphorescent host, a fluorescent host, or a fluorescent dopant.

The heterocyclic compound of Formula 1 or Formula 2 may be used as a host. In another embodiment a widely-known dopant may be used. Non-limiting examples of known hosts include Alq₃(Tris(8-hydroxyquinolinato)aluminium), CBP (4,4'-N,N'-dicabazole-biphenyl), PVK (poly(n-vinyl-cabazole), ADN (9,10-di(naphthalene-2-yl)anthracene), TCTA, TPBI ((1,3,5-tris(N-phenylbenzimidazole-2-yl)benzene), TBADN ((3-tert-butyl-9,10-di(naphth-2-yl)anthracene), distyrylarylene (DSA), and E3.

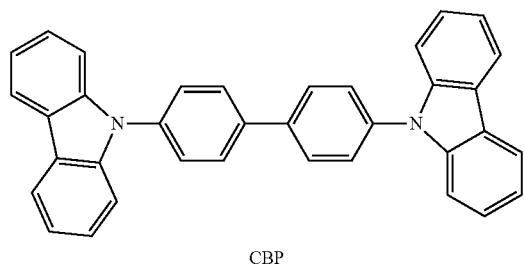

CBP

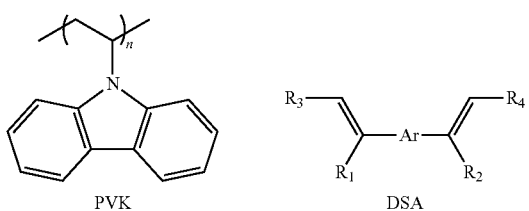

PVK

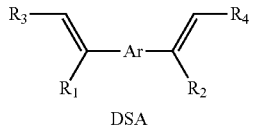

DSA

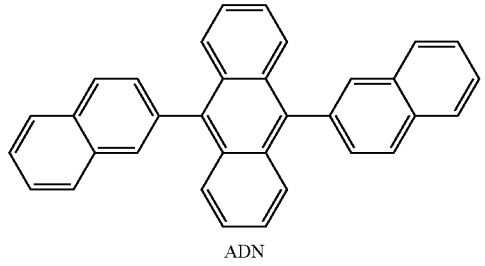

ADN

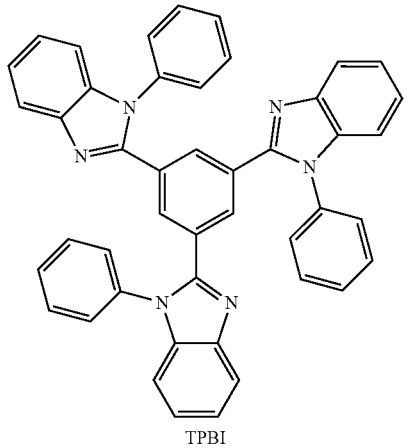

TPBI

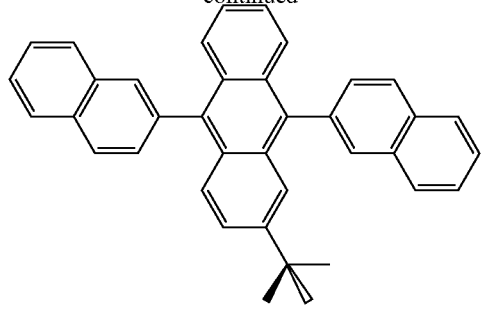

TBADN

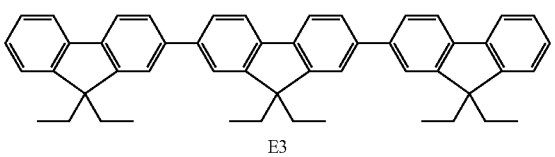 [SMILES: CCC1(CC)c2ccccc2-c2ccc(-c3ccc4c(c3)C(CC)(CC)c3cc(-c5ccc6c(c5)C(CC)(CC)c5ccccc5-6)ccc3-4)cc21]

E3

The heterocyclic compound of Formula 1 or Formula 2 may be used as a dopant. In another embodiment a widely-known dopant may be used. For example, at least one of a fluorescent dopant and a phosphorescent dopant may be used. For example, the phosphorescent dopant may include, but is not limited to, an organometallic complex including at least one selected from the group consisting of iridium (Ir), platinum (Pt), osmium (Os), rhenium (Re), titanium (Ti), zirconium (Zr), hafnium (Hf), and a combination of at least two thereof.

Non-limiting examples of widely known red dopants include PtOEP (Pt(II) octaethylporphine), Ir(piq)₃ (tris(2-phenylisoquinoline)iridium), and Btp₂Ir(acac) (bis(2-(2t-benzothienyl)-pyridinato-N,C3')iridium(acetylacetonate)).

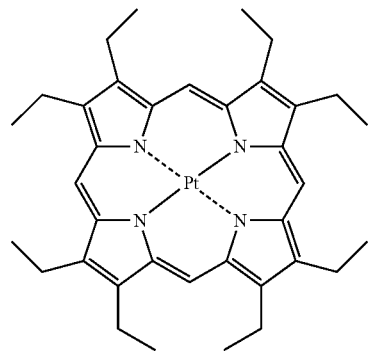

PtOEP

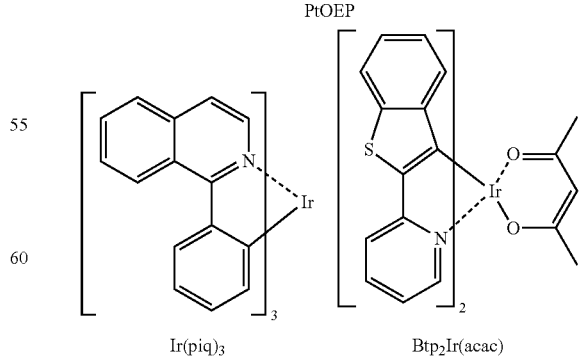

Ir(piq)₃       Btp₂Ir(acac)

Non-limiting examples of widely known red dopants include Ir(ppy)₃ (tris(2-phenylpyridine) iridium), Ir(ppy)₂

(acac) (bis(2-phenylpyridine)(acetylacetonato)iridium(III), Ir(mppy)₃ (tris(2-(4-tolyl)phenylpiridine)iridium), and C545T (10-(2-benzothiazolyl)-1,1,7,7-tetramethyl-2,3,6,7-tetrahydro-1H,5H,11H-[l]benzopyrano[6,7,8-ij]-quinolizin-11-one).

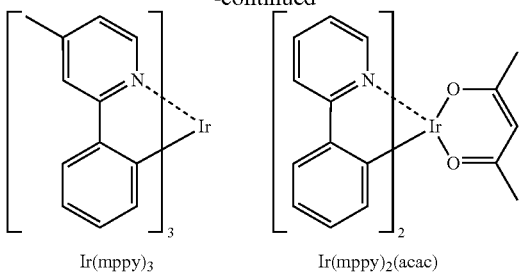

Ir(mppy)₃     Ir(mppy)₂(acac)

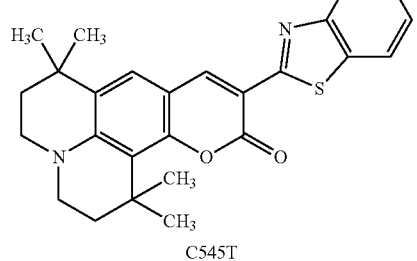

C545T

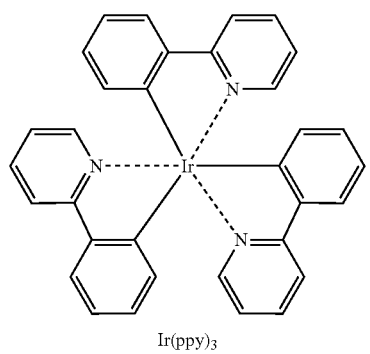

Ir(ppy)₃

Non-limiting examples of widely known blue dopants include F₂Irpic (bis[3,5-difluoro-2-(2-pyridyl)phenyl](picolinato)iridium(III)), (F₂ppy)₂Ir(tmd), Ir(dfppz)₃, DPVBi (4,4'-bis(2,2'-diphenylethen-1-yl)biphenyl), DPAVBi (4,4'-bis[4-(diphenylamino)styryl]biphenyl), and TBPe (2,5,8,11-tetra-tert-butyl perylene).

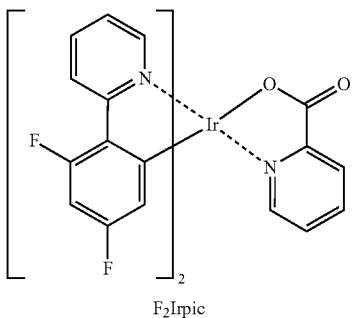
F₂Irpic

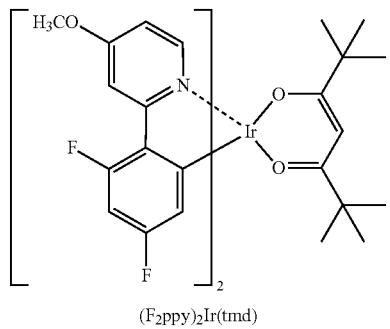
(F₂ppy)₂Ir(tmd)

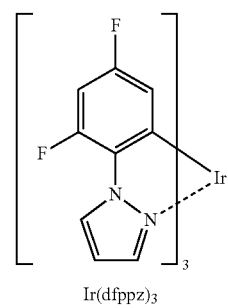
Ir(dfppz)₃

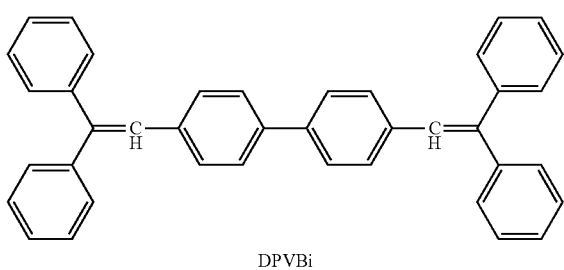
DPVBi

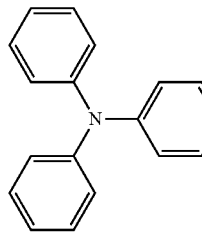
DPAVBi

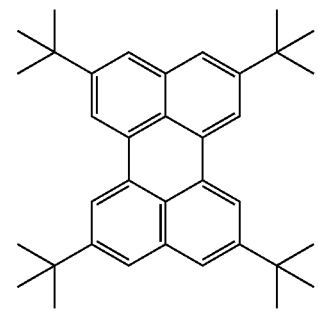
TBPe

When the EML includes both a host and a dopant, the amount of the dopant may be from about 0.01 to about 15 parts by weight based on 100 parts by weight of the host. However, the amount of the dopant is not limited to this range.

The thickness of the EML may be from about 100 Å to about 1000 Å, and in some embodiments, may be from about 200 Å to about 600 Å. When the thickness of the EML is within these ranges, the EML may have good light emitting ability without a substantial increase in driving voltage.

When a phosphorescent dopant is added to form the EML, a hole blocking layer (HBL) may be formed between the ETL and the EML by using vacuum deposition, spin coating, casting, LB deposition, or the like, in order to prevent diffusion of triplet excitons or holes into an ETL. When the HBL is formed using vacuum deposition or spin coating, the conditions for deposition and coating may be similar to those for the formation of the HIL, although the conditions for deposition and coating may vary according to the material that is used to form the HBL. Any widely known hole-blocking material may be used. Non-limiting examples of hole-blocking materials include an oxadiazole derivative, a triazole derivative, and a phenanthroline derivative. For example, 2,9-dimethyl-4,7-diphenyl-1,10-phenanthroline (BCP) may be used as a material for forming the HBL.

The thickness of the HBL may be from about 50 Å to about 1000 Å, and in some embodiments, may be from about 100 Å to about 300 Å. When the thickness of the HBL is within these ranges, the HBL may have a good hole blocking ability without a substantial increase in driving voltage.

Then, an ETL may be formed on the HBL or EML by vacuum deposition, spin coating, casting, or the like. When the ETL is formed using vacuum deposition or spin coating, the deposition and coating conditions may be similar to those for the formation of the HIL, though the deposition and coating conditions may vary according to the material that is used to form the ETL.

The ETL may be formed of any widely known electron transporting material. Non-limiting examples of widely known ETL materials include quinoline derivatives, and in particular, Alq3 (tris(8-quinolinolate)aluminum), BCP (2,9-dimethyl-4,7-diphenyl-1,10-phenanthroline), Bphen (4,7-diphenyl-1,10-phenanthroline), TAZ (3-(4-biphenylyl)-4-phenyl-5-tert-butylphenyl-1,2,4-triazole), NTAZ (4-(Naphthalen-1-yl)-3,5-diphenyl-4H-1,1,2,4-triazole), tBu-PBD(2-(4-biphenylyl)-5-(4-tert-butylphenyl)-1,3,4-oxadiazole, BAlq (see the following formula), Bebq$_2$ (beryllium bis(benzoquinolin-10-olate), AND (9,10-di(naphthalene-2-yl)anthrascene), Compound 101, and Compound 102.

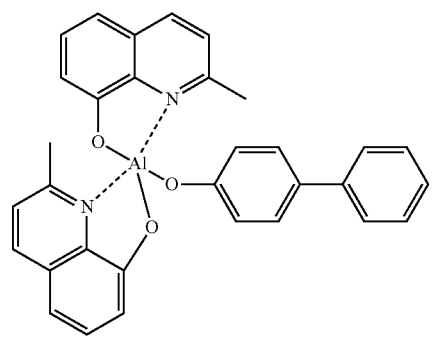
BAlq

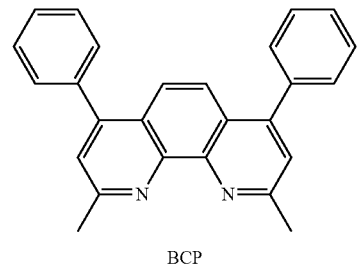
BCP

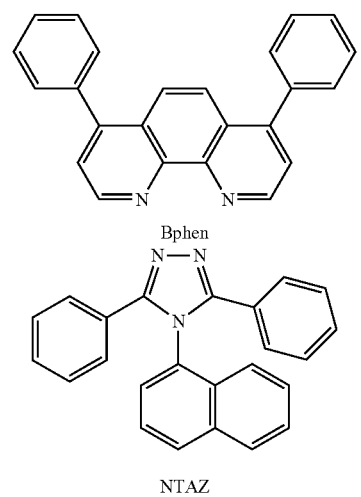
Bphen

NTAZ

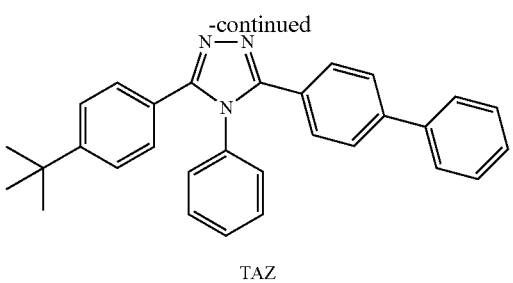

TAZ

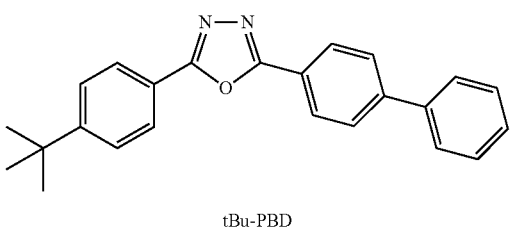

tBu-PBD

Compound 101

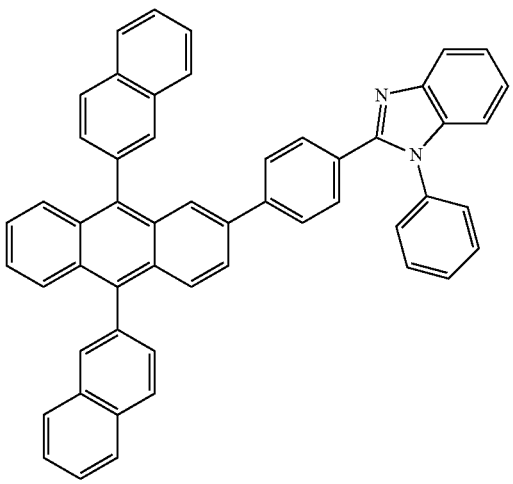

Compound 102

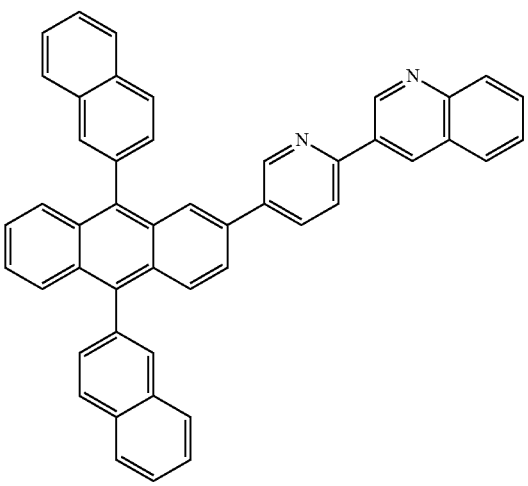

The thickness of the ETL may be from about 100 Å to about 1,000 Å, and in some embodiments, may be from about 150 Å to about 500 Å. When the thickness of the ETL is within these ranges, the ETL may have satisfactory electron transporting ability without a substantial increase in driving voltage.

In some embodiments the ETL may include an electron-transporting organic compound and a metal-containing material. The metal-containing material may include a lithium (Li) complex. Non-limiting examples of the Li complex include lithium quinolate (LiQ) and Compound 103 below:

Compound 103

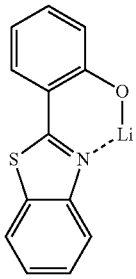

Then, the EIL, which facilitates injection of electrons from the cathode, may be formed on the ETL. Any suitable electron-injecting material may be used to form the EIL.

Examples of materials for forming the EIL include LiF, NaCl, CsF, $Li_2O$, and BaO, which are known in the art. The deposition and coating conditions for forming the EIL may be similar to those for the formation of the HIL, though the deposition and coating conditions may vary according to the material that is used to form the EIL.

The thickness of the EIL may be from about 1 Å to about 100 Å, and in some embodiments, may be from about 3 Å to about 90 Å. When the thickness of the EIL is within these ranges, the EIL may have satisfactory electron injection ability without a substantial increase in driving voltage.

The second electrode 17 is disposed on the organic layer 15. The second electrode 17 may be a cathode that is an electron injection electrode. A material for forming the second electrode 17 may be a metal, an alloy, an electro-conductive compound, which have a low work function, or a mixture thereof. In this regard, the second electrode 17 may be formed of lithium (Li), magnesium (Mg), aluminum (Al), aluminum (Al)-lithium (Li), calcium (Ca), magnesium (Mg)-indium (In), magnesium (Mg)-silver (Au), or the like, and may be formed as a thin film type transmission electrode. To manufacture a top-emission light-emitting device, the transmission electrode may be formed of indium tin oxide (ITO) or indium zinc oxide (IZO).

Hereinafter, the present invention will be described in detail with reference to the following synthesis examples and other examples. However, these examples are for illustrative purposes only and are not intended to limit the scope of the present invention.

EXAMPLES
Synthesis Example 1
Synthesis of Compound 3 (Synthetic Pathway 1)
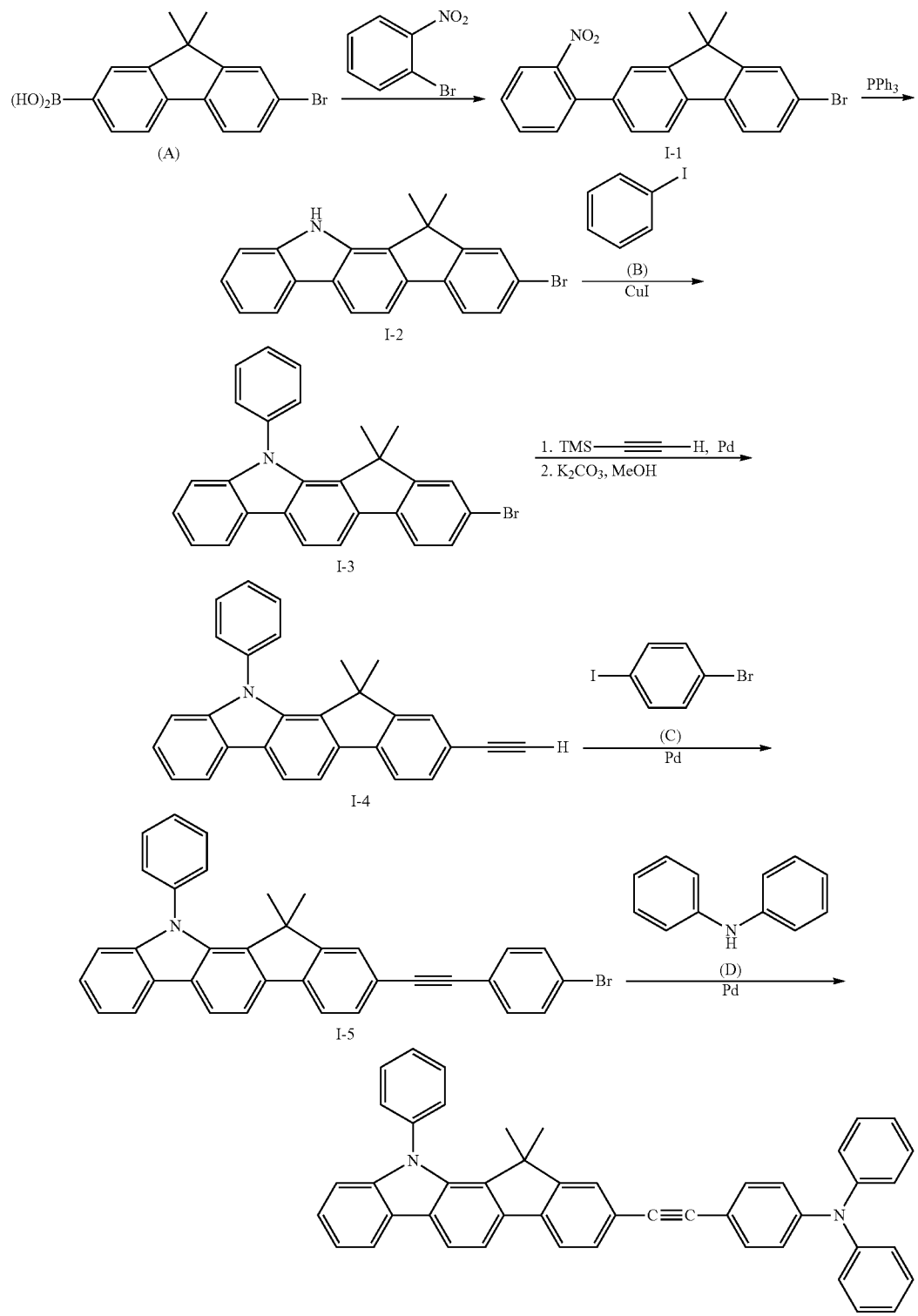

Synthesis of Intermediate I-1

6.34 g (20.0 mmol) of 2-bromo-9,9-dimethyl-7-fluoreneboronic acid, 4.04 g (20.0 mmol) of 2-bromonitrobenzene, 1.15 g (1.0 mmol) of Pd(PPh$_3$)$_4$ (tetrakis(triphenylphosphine)palladium), and 8.29 g (60.0 mmol) of K$_2$CO$_3$ were dissolved in 60 mL of a mixed tetrahydrofuran (THF) and H$_2$O (2:1 by volume) solution to obtain a solution, which was then stirred at about 70° C. for about 5 hours. The reaction solution was cooled to room temperature, and 40 mL of water was added thereto, followed by three times of extraction with 50 mL of ethyl ether. The organic layer was collected and was dried using magnesium sulfate to evaporate the solvent. The residue was separated and purified using silica gel column chromatography to obtain 6.86 g of Intermediate I-1 (Yield: 87%). This compound was identified using mass spectroscopy/fast atom bombardment (MS/FAB). C$_{21}$H$_{16}$BrNO$_2$: calc. 393.04. Found 393.14.

Synthesis of Intermediate I-2

3.94 g (10.0 mmol) of Intermediate I-1 and 5.77 g (22 mmol) of triphenylphosphine (PPM were dissolved in 30 mL of 1,2-dichlorobenzene to obtain a solution, which was then stirred at about 220° C. for about 12 hours. The reaction solution was cooled to room temperature, and the solvent was removed therefrom under vacuum conditions, followed by three times of extraction with 50 mL of water and 50 mL of dichloromethane. The organic layer was collected and was dried using magnesium sulfate to evaporate the solvent. The residue was separated and purified using silica gel column chromatography to obtain 2.83 g of Intermediate I-2 (Yield: 78%). This compound was identified using MS/FAB. C$_{21}$H$_{16}$BrN:calc. 361.05. Found 361.26.

Synthesis of Intermediate I-3

3.62 g (10.0 mmol) of Intermediate I-2, 3.06 g (15.0 mmol) of iodobenzene, 0.19 g (1.0 mmol) of CuI: 0.05 g (0.2 mmol) of 18-Crown-6, and 4.15 g (30.0 mmol) of K$_2$CO$_3$ were dissolved in 30 mL of 1,3-dimethyl-3,4,5,6-tetrahydro-2(1H)-pyrimidinone (DMPU) to obtain a solution, which was then stirred at about 170° C. for about 12 hours. The reaction solution was cooled to room temperature, followed by three times of extraction with 50 mL of water and 50 mL of dichloromethane. The organic layer was collected and was dried using magnesium sulfate to evaporate the solvent. The residue was separated and purified using silica gel column chromatography to obtain 4.03 g of Intermediate I-3 (Yield: 92%). This compound was identified using MS/FAB. C$_{27}$H$_{20}$BrN: calc. 437.08. Found 437.31.

Synthesis of Intermediate I-4

8.77 g (20.0 mmol) of Intermediate I-3, 1.96 g (20.0 mmol) of trimethylsilylacetylene, 0.924 g (0.8 mmol) of Pd(PPh$_3$)$_4$, 0.32 g (1.6 mmol) of CuI, and 3.03 g (30.0 mmol) of triethylamine were dissolved in 90 mL of dimethylacetamide to obtain a solution, which was then stirred at about 80° C. for about 12 hours. The reaction solution was cooled to room temperature, followed by three times of extraction with 100 mL of water (H$_2$O) and 100 mL of diethyl ether. The organic layer was collected and dried using magnesium sulfate. The solvent was evaporated to obtain a residue, which was then dissolved in 50 mL of dichloromethane, followed by an addition of 11g (80.0 mmol) of K$_2$CO$_3$ and 10 mL of methanol and stirring at room temperature for about 5 hours. The reaction solution was subjected to extraction with 50 mL of H$_2$O. The organic layer was collected and was dried using magnesium sulfate to evaporate the solvent. The residue was separated and purified using silica gel column chromatography to obtain 5.75 g of Intermediate I-4 (Yield: 75%). This compound was identified using MS/FAB. C$_{29}$H$_{21}$N:calc. 383.17. Found 383.41.

Synthesis of Intermediate I-5

5.75 g (15.0 mmol) of Intermediate I-4, 4.24 g (15.0 mmol) of 4-bromonitrobenzene, 0.693 g (0.6 mmol) of Pd(PPh$_3$)$_4$, 0.228 g (1.2 mmol) of CuI, and 2.28 g (22.5 mmol) of triethylamine were dissolved in 60 mL of dimethylacetamide to obtain a solution, which was then stirred at about 80° C. for about 10 hours. The reaction solution was cooled to room temperature, followed by three times of extraction with 50 mL of H$_2$O and 60 mL of diethyl ether. The organic layer was collected and was dried using magnesium sulfate to evaporate the solvent. The residue was separated and purified using silica gel column chromatography to obtain 7.35 g of Intermediate I-5 (Yield: 91%). This compound was identified using MS/FAB. C$_{35}$H$_{24}$BrN:calc. 537.11. Found 537.34.

Synthesis of Compound 3

5.38 g (10.0 mmol) of Intermediate I-5, 2.03 g (12.0 mmol) of diphenyl amine, 0.183 g (0.2 mmol) of Pd$_2$(dba)$_3$, 0.04 g (0.2 mmol) of P(t-Bu)$_3$, and 1.44 g (15.0 mmol) of NaOtBu were dissolved in 30 mL of toluene to obtain a solution, which was then stirred at about 85° C. for about 6 hours. The reaction solution was cooled to room temperature, followed by three times of extraction with 50 mL of H$_2$O and 60 mL of diethyl ether. The organic layer was collected and was dried using magnesium sulfate to evaporate the solvent. The residue was separated and purified using, silica gel column chromatography to obtain 7.35 g of Compound 3 (Yield: 87%). This compound was identified using $^1$H NMR and MS/FAB. C$_{47}$H$_{34}$N$_2$:calc. 626.27. Found 626.34.

Synthesis Example 2

Synthesis of Compound 55 (Synthetic Pathway 2)

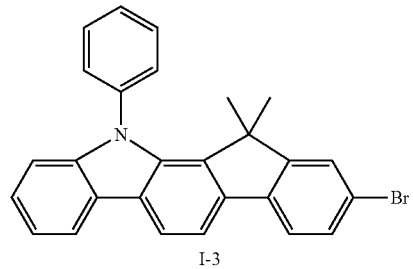

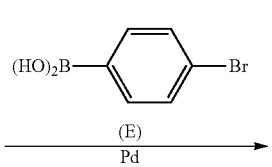

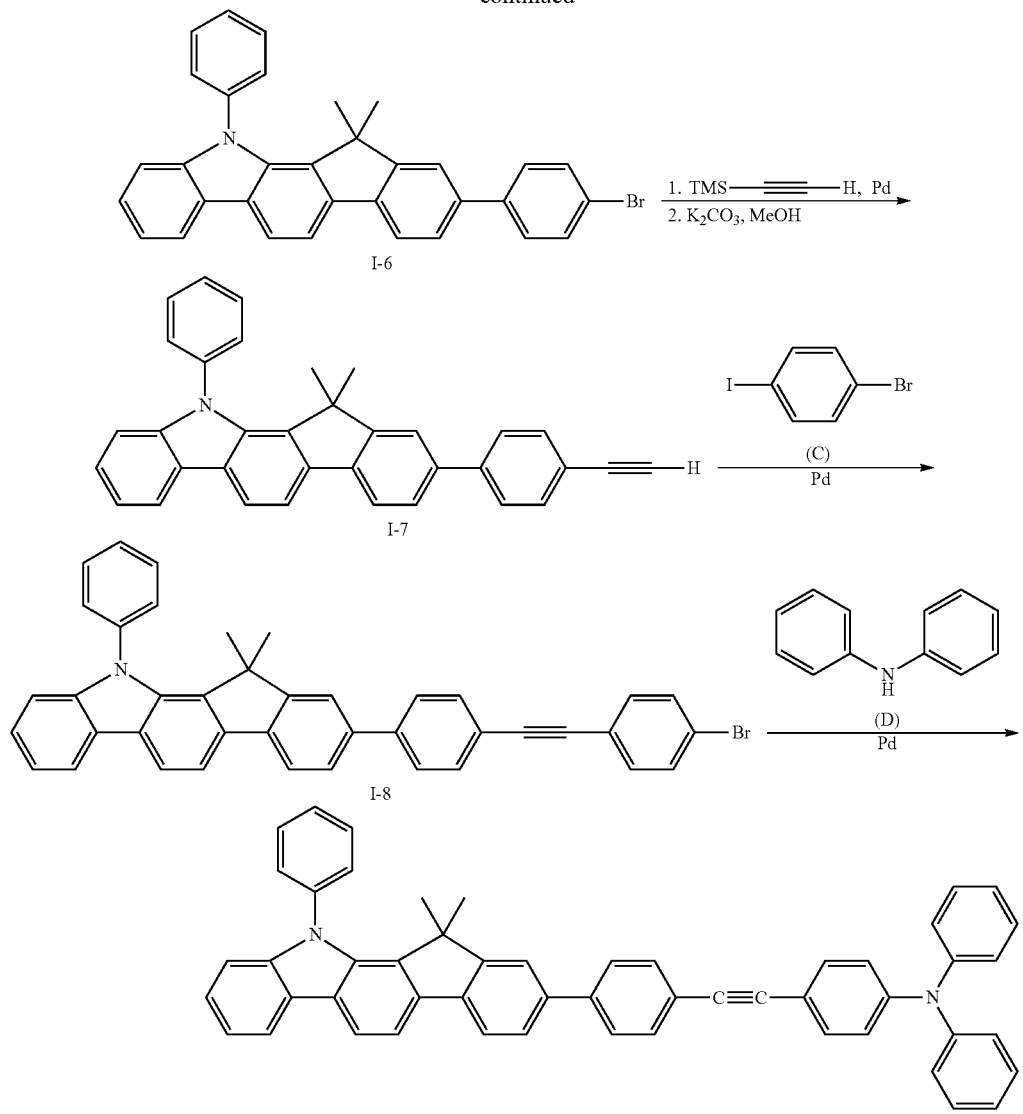

Synthesis of Intermediate I-6

4.38 g (10.0 mmol) of Intermediate I-3, 2.0 g (10.0 mmol) of 4-bromobenzene boronic acid, 0.577 g (0.5 mmol) of Pd(PPh$_3$)$_4$, and 4.14 g (30.0 mmol) of K$_2$CO$_3$ were dissolved in 40 mL of a mixed tetrahydrofuran (THF) and H$_2$O (1:1) solution to obtain a solution, which was then stirred at about 80° C. for about 4 hours. The reaction solution was cooled to room temperature, followed by three times of extraction with 50 mL of H$_2$O and 60 mL of diethyl ether. The organic layer was collected and was dried using magnesium sulfate to evaporate the solvent. The residue was separated and purified using silica gel column chromatography to obtain 3.91 g of Intermediate I-6 (Yield: 76%). This compound was identified using MS/FAB. C$_{33}$H$_{24}$BrN:calc. 513.11. Found 513.24.

Synthesis of Intermediate I-7

3.49 g or Intermediate I-7 was synthesized using Intermediate I-6, instead of Intermediate I-3, in the same manner as in the synthesis of Intermediate I-4 (Yield: 76%). This compound was identified using MS/FAB. C$_{35}$H$_{25}$N:calc. 459.20. Found 459.42.

Synthesis of Intermediate I-8

5.41 g of Intermediate I-8 was synthesized using Intermediate I-7, instead of Intermediate I-4, in the same manner as in the synthesis of Intermediate I-5 (Yield: 88%). This compound was identified using liquid MS/FAB. C$_{41}$H$_{28}$BrN:calc. 613.14. Found 613.41.

Synthesis of Compound 55

3.06 g of Compound 55 was synthesized using Intermediate I-8, instead of Intermediate I-5, in the same manner as in the synthesis of Compound 3 (Yield: 87%). This compound was identified using $^1$H NMR and MS/FAB. C$_{53}$H$_{38}$N$_2$:calc. 702.30. Found 702.35.

Synthesis Example 3
Synthesis of Compound 64 (Synthetic Pathway 3)
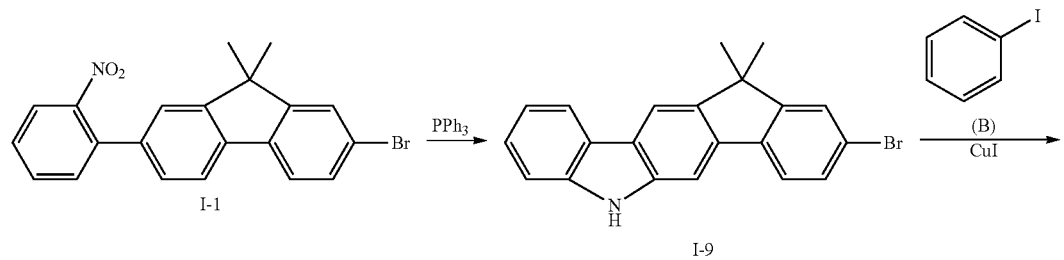
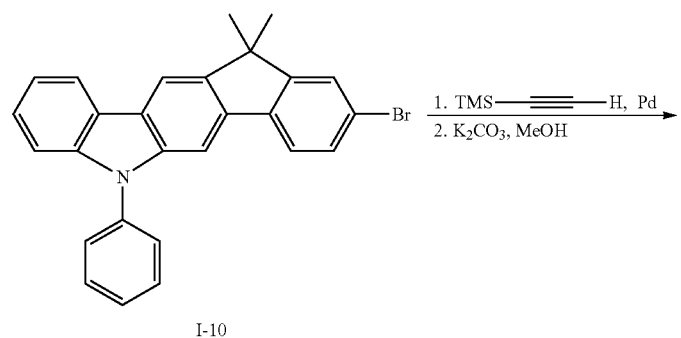
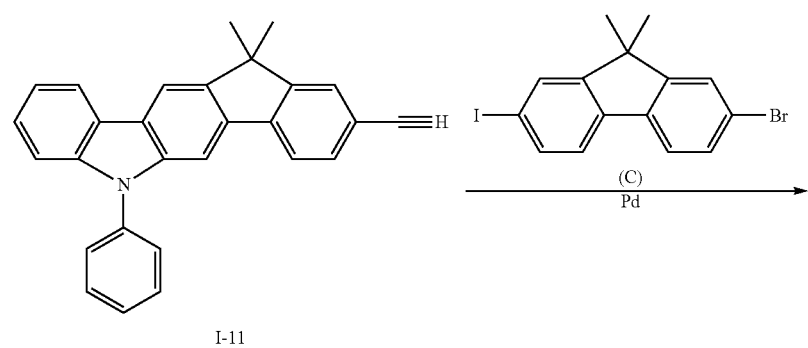
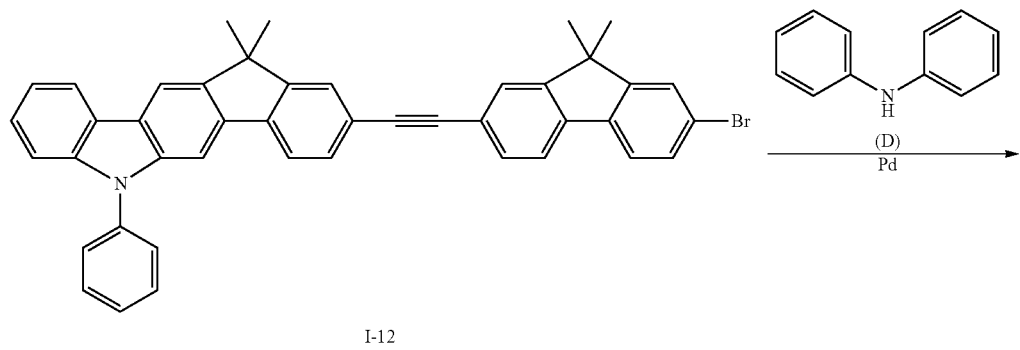

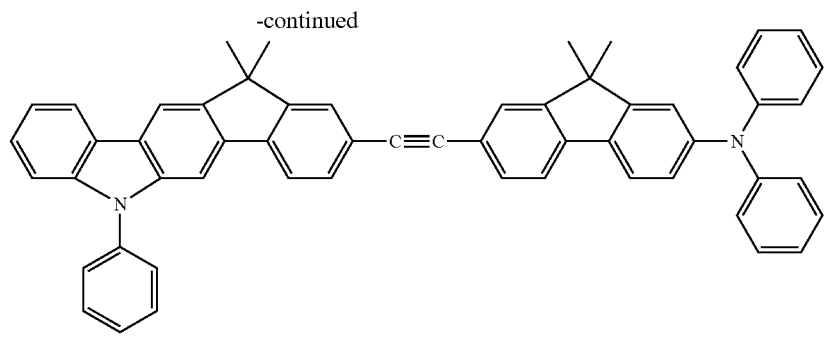

64

Synthesis of Intermediate I-9

3.94 g (10.0 mmol) of Intermediate I-1 and 5.77 g (22 mmol) of triphenylphosphine (PPh$_3$) were dissolved in 30 mL of 1,2-dichlorobenzene to obtain a solution, which was then stirred at about 170° C. for about 12 hours. The reaction solution was cooled to room temperature, and the solvent was removed therefrom under vacuum conditions, followed by three times of extraction with 50 mL of water and 50 mL of dichloromethane. The organic layer was collected and was dried using magnesium sulfate to evaporate the solvent. The residue was separated and purified using silica gel column chromatography to obtain 2.35 g of Intermediate I-9 (Yield: 65%). This compound was identified using MS/FAB. C$_{21}$H$_{16}$BrN:calc. 361.05. Found 361.33.

Synthesis of Intermediate I-10

3.90 g of Intermediate I-10 was synthesized using Intermediate I-9, instead of Intermediate I-2, in the same manner as in the synthesis of Intermediate I-3 (Yield: 89%). This compound was identified using MS/FAB. C$_{27}$H$_{20}$BrN:calc. 437.08. Found 437.24.

Synthesis of Intermediate I-11

2.95 g of Intermediate I-11 was synthesized using Intermediate I-10, instead of Intermediate I-3, in the same manner as in the synthesis of Intermediate I-4 (Yield: 77%). This compound was identified using MS/FAB. C$_{29}$H$_{21}$N:calc. 383.17. Found 383.32.

Synthesis of Intermediate I-12

4.74 g of Intermediate I-12 was synthesized using Intermediate I-11, instead of Intermediate I-4, and using 2-iodo-7-bromo-9,9'-dimethylfluorene, instead of 4-bromoiodobenzene, in the same manner as in the synthesis of Intermediate I-5 (Yield: 88%). This compound was identified using MS/FAB. C$_{35}$H$_{24}$BrN:calc. 537.11. Found 537.19.

Synthesis of Compound 64

3.23 g of Compound 64 was synthesized using Intermediate I-12, instead of Intermediate I-5, in the same manner as in the synthesis of Compound 3 (Yield: 87%). This compound was identified using $^1$H NMR and MS/FAB. C$_{56}$H$_{42}$N$_2$:calc. 742.33. Found 742.45.

Synthesis Example 4

Synthesis of Compound 89 (Synthetic Pathway 4)

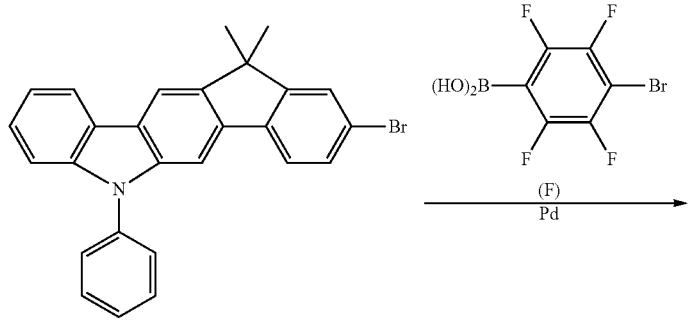

I-10

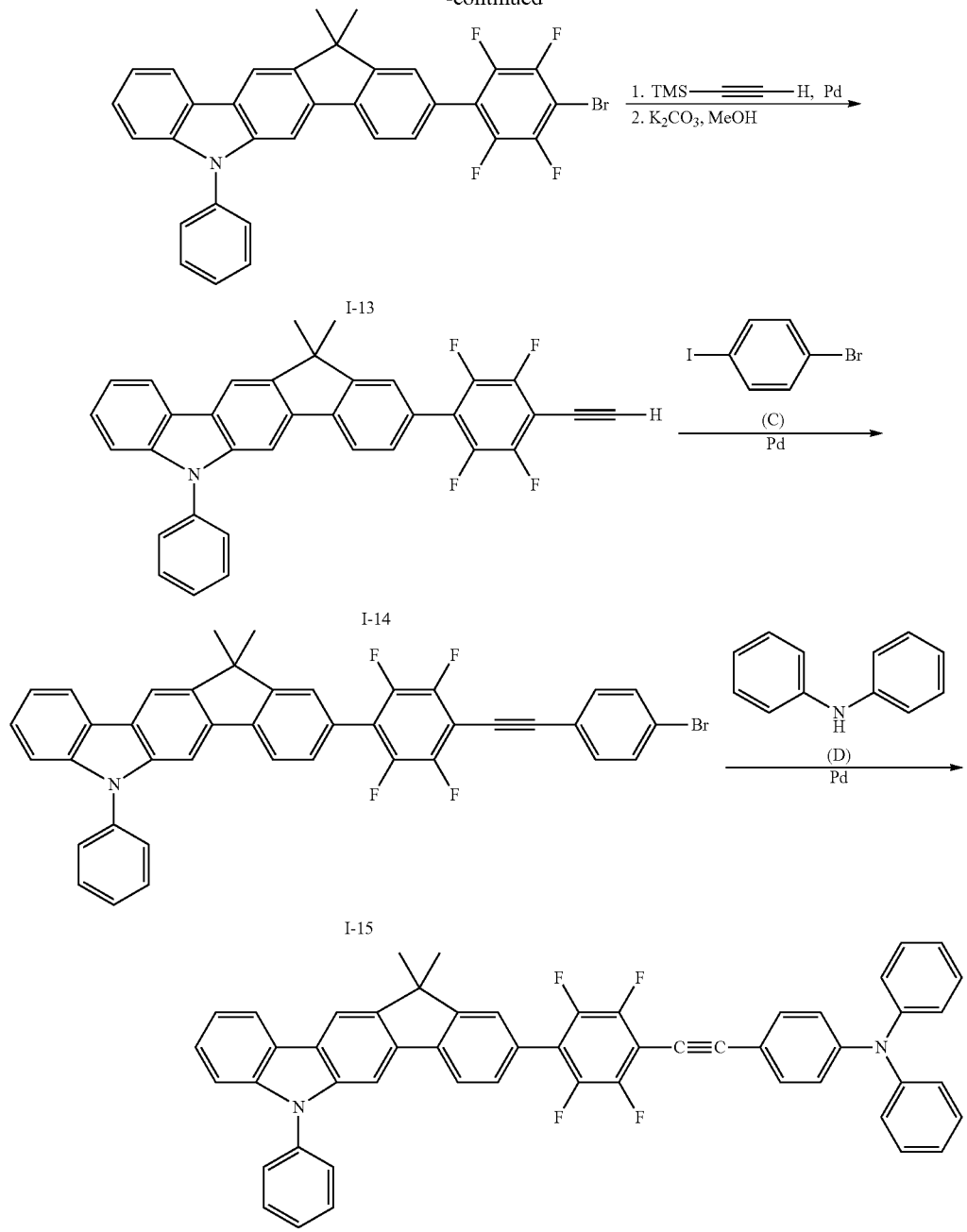

Synthesis of Compound 89

Intermediate I-13 was synthesized using Intermediate I-10, instead of Intermediate I-3, in the same manner as in the synthesis of Intermediate I-6. Intermediate I-14, Intermediate I-15, and Compound 89 were synthesized using Intermediate I-13, instead of Intermediate I-6, in the same manner as in the synthesis of Compound 55.

Compounds 1, 3-5, 7-10, 12, 14, 17, 18, 21-23, 26, 27, 29-35, 37-40, 42, 43, 46, 48, 52-56, 58-61, 63-65, 67, 69, 71, 74-77, 79, 80, 82, 85-89, and 92 were synthesized using appropriate source materials according to Synthesis Examples 1 to 4 (Synthetic pathways 1 to 4), and were identified using $^1$H NMR and MS/FAB. The results are shown in Table 1 below. In Table 1, the synthetic pathway for each compound and used source materials that differ from those involved in the above-described synthetic pathways are also presented. For example, Compound 1 was synthesized in the same manner as in the Synthetic pathway 1, except that ethyl iodide was used instead of iodobenzene, which is the material denoted by (B) in the Synthetic pathway 1. As another example, Compound 23 was synthesized in the to same manner as in the Synthetic pathway 1, except that iodonaphthalene, instead of iodobenzene denoted by (B) in the Synthetic pathway 1, and diphenyl-$d_{10}$ amine, instead of diphenylamine denoted by (D), were used. For the other compounds, their synthetic pathway and source materials used will be understood from Table 1 by one of ordinary skill in the art.

TABLE 1

| Compound | Synthetic Pathway | Source material used, but not in original synthetic pathway | ¹H NMR (CDCl₃, 400 MHz) | MS/FAB found | calc. |
|---|---|---|---|---|---|
| 1 | 1(B) | (ethyl group, Ha₁) | δ = □8.09 (d, 1H), 7.79-7.62 (m, 4H), 7.53-7.42 (m, 4H), 7.31 (d, 1H), 7.22-7.20 (m, 1H), 7.12-7.06 (m, 6H), 6.97-6.94 (m, 2H), 6.76-6.73 (m, 4H), 4.70 (q, 2H), 1.78 (s, 6H), 1.35 (t, 3H) | 578.36 | 578.27 |
| 3 | 1 (B) | (phenyl, Ha₁) | δ = 8.06 (d, 1H), 7.83-7.76 (m, 2H), 7.72-7.60 (m, 6H), 7.54-7.51 (m, 2H), 7.48-7.40 (m, 4H), 7.33-7.13 (m, 7H), 6.99-6.93 (m, 2H), 6.86-6.83 (m, 4H), 1.75 (s, 6H) | 626.34 | 626.27 |
| 4 | 1 (B) | (deuterated phenyl, D₅, Ha₁) | δ = 8.11 (d, 1H), 7.85-7.81 (m, 2H), 7.74-7.72 (m, 2H), 7.63-7.60 (m, 2H), 7.44-7.29 (m, 3H), 7.33-7.29 (m, 1H), 7.22-7.13 (m, 6H), 7.03-7.00 (m, 2H), 6.78-6.76 (m, 4H), 1.78 (s, 6H) | 631.58 | 631.30 |
| 5 | 1 (A) | (fluorene with D₃C, CD₃; Bo₁, Ha₁) | δ = 8.16 (d, 1H), 7.83-7.76 (m, 2H), 7.71-7.69 (m, 2H), 7.63-7.57 (m, 4H), 7.54-7.51 (m, 2H), 7.47-7.40 (m, 4H), 7.33-7.30 (m, 1H), 7.22-7.13 (m, 6H), 6.91-6.89 (m, 2H), 6.77-6.74 (m, 4H), | 632.75 | 632.31 |
| 7 | 1 (A) | (9,9-diphenylfluorene; Bo₁, Ha₁) | δ = 8.13 (d, 1H), 7.94-7.92 (d, 1H), 7.69-7.60 (m, 6H), 7.53-7.32 (m, 7H), 7.25-7.09 (m, 17H), 6.99-6.93 (m, 2H), 6.87-6.83 (m, 4H) | 750.21 | 750.30 |
| 8 | 1 (A, B) | (spirobifluorene; Bo₁, Ha₁) (A); (ethyl, Ha₁) (B) | δ = 8.12 (d, 1H), 7.95-7.85 (m, 3H), 7.75 (d, 1H), 7.67-7.61 (m, 2H), 7.53-7.42 (6H), 7.34-7.14 (m, 9H), 7.08 (d, 1H), 6.90-6.83 (m ,4H), 6.76-6.73 (m ,4H), 4.65 (q, 2H), 1.38 (t, 3H) | 700.42 | 700.29 |

TABLE 1-continued

| Compound | Synthetic Pathway | Source material used, but not in original synthetic pathway | $^1$H NMR (CDCl$_3$, 400 MHz) | MS/FAB found | calc. |
|---|---|---|---|---|---|
| 9 | 1 (B) | (2-naphthyl-Hal) | δ = 8.18 (d, 1H), 7.94-7.92 (d, 1H), 7.85-7.76 (m, 3H), 7.65-7.50 (m, 7H), 7.45-7.34 (m, 5H), 7.31-7.29 (m, 1H), 7.23-7.14 (m, 6H), 6.87-6.83 (m, 2H), 6.76-6.72 (m, 4H), 1.79 (s, 6H) | 676.41 | 676.29 |
| 10 | 1 (B) | (4-biphenyl-Hal) | δ = 8.13 (d, 1H), 7.83-7.76 (m, 2H), 7.73-7.71 (m, 4H), 7.66-7.49 (m, 7H), 7.42-7.40 (m, 3H), 7.29-7.26 (m, 3H), 7.22-7.13 (m, 6H), 6.86-6.83 (m, 2H), 6.73-6.71 (m, 4H), 1.80 (s, 6H) | 702.56 | 702.30 |
| 12 | 1 (B) | (1-pyrenyl-Hal) | δ = 8.14 (d, 3H), 8.04-7.98 (m, 4H), 7.89-7.86 (d, 2H), 7.78-7.74 (m, 2H), 7.65-7.60 (m, 2H), 7.56-7.50 (m, 3H), 7.45-7.41 (m, 3H), 7.23-7.09 (7H), 6.99-6.96 (m, 2H), 6.86-6.83 (m, 4H), 1.75 (d, 6H) | 750.42 | 750.30 |
| 14 | 1 (B) | (9,9-dimethylfluorenyl-Hal) | δ = 8.18 (d, 1H), 7.87-7.76 (m, 3H), 7.64-7.60 (m, 5H), 7.38 (d, 1H), 7.34-7.30 (m, 4H), 7.28-7.20 (m, 3H), 7.19-7.07 (m, 7H), 6.89-6.83 (m, 2H), 6.80-6.76 (m, 4H), 1.78 (d, 6H), 1.72 (s, 6H) | 742.63 | 742.33 |
| 17 | 1 (D) | (N-phenyl-1-naphthylamine) | δ = 8.13 (d, 1H), 7.93-7.96 (m, 2H), 7.84-7.80 (m, 4H), 7.65-7.58 (m, 6H), 7.55-7.46 (m, 6H), 7.44-7.40 (m, 3H), 7.32-7.29 (m, 1H), 7.22-7.13 (m, 4H), 7.06-7.02 (m, 2H), 6.86-6.82 (m, 1H), 6.72-6.70 (m, 2H), 1.81 (s, 6H) | 702.65 | 702.30 |
| 18 | 1 (D) | (N-phenyl-9,9-dimethylfluorenyl-2-amine) | δ = 8.11 (d, 1H), 7.86-7.83 (m, 3H), 7.74-7.72 (m, 2H), 7.66-7.61 (m, 6H), 7.54-7.51 (m, 2H), 7.48-7.33 (m, 6H), 7.28-7.14 (m, 5H), 7.07-7.00 (m, 2H), 6.87 (d, 1H), 6.79-6.77 (m, 2H), 1.73 (s, 6H), 1.69 (s, 6H) | 742.55 | 742.33 |

TABLE 1-continued

| Compound | Synthetic Pathway | Source material used, but not in original synthetic pathway | ¹H NMR (CDCl₃, 400 MHz) | MS/FAB found | calc. |
|---|---|---|---|---|---|
| 21 | 1 (D) | (structure: bis(2-fluorophenyl)amine) | δ = 7.99 (d, 1H), 7.88-7.84 (m, 2H), 7.76-7.73 (m, 2H), 7.66-7.62 (m, 2H), 7.57-7.51 (m, 4H), 7.48-7.39 (m, 4H), 7.32-7.28 (m, 3H), 7.26-7.18 (m, 2H), 7.08-7.01 (m, 4H), 6.89-6.84 (m, 2H), 1.72 (s, 6H) | 662.31 | 662.25 |
| 22 | 1 (D) | (structure: fluoro-terphenyl-N-phenylamine) | δ = 8.06 (d, 1H), 7.83-7.76 (m, 2H), 7.74-7.63 (m, 7H), 7.58-7.40 (m, 12H), 7.38-7.29 (4H), 7.23-7.12 (m, 6H), 7.03-7.69 (m, 1H), 6.75-6.73 (m, 2H), 1.69 (s, 6H) | 796.46 | 796.33 |
| 23 | 1 (B, D) | (structures: Hal-naphthalene (B); deuterated diphenylamine) Specifically, D may be A1. | δ = 8.18 (d, 1H), 7.95 (d, 1H), 7.85-7.78 (m, 3H), 7.75-7.70 (m, 3H), 7.67-7.59 (m, 4H), 7.54-7.40 (m, 5H), 7.22-7.17 (m, 1H), 7.13-7.09 (m, 2H), 1.69 (s, 6H) | 686.41 | 686.35 |
| 26 | 1 (D) | (structure: N-phenyl-4-(9,9-dimethylfluoren-2-yl)aniline) | δ = 8.16 (d, 1H), 7.92-7.74 (m, 4H), 7.70-7.65 (m, 3H), 7.59-7.7.40 (m, 14H), 7.33-7.14 (m, 7H), 6.91-6.87 (m, 2H), 6.86-6.83 (m, 1H), 6.63-6.60 (m, 2H), 1.75 (s, 6H), 1.64 (s, 6H) | 818.49 | 818.37 |
| 27 | 1 (D) | (structure: N-phenyl-2-pyridylamine) | δ = 8.22 (dd, 1H), 8.11 (d, 1H), 7.94-7.89 (m, 2H), 7.73-7.61 (m, 6H), 7.54-7.51 (m, 3H), 7.48-7.40 (m, 4H), 7.36-7.29 (m, 4H), 7.16-7.13 (m, 2H), 7.05-7.01 (m, 1H), 6.99 (dd, 1H), 6.79-6.76 (m, 2H), 1.73 (s, 6H) | 627.35 | 627.27 |

TABLE 1-continued

| Compound | Synthetic Pathway | Source material used, but not in original synthetic pathway | ¹H NMR (CDCl₃, 400 MHz) | MS/FAB found | calc. |
|---|---|---|---|---|---|
| 29 | 1 (C) | Ha₁—(C₆H₄)—(C₆H₄)—Ha₂ | δ = 8.08 (d, 1H), 7.79-7.71 (m, 4H), 7.65-7.56 (m, 8H), 7.44-7.41 (m, 2H), 7.39-7.30 (m, 4H), 7.22-7.19 (m, 1H), 7.13-7.10 (m, 4H), 6.96-6.92 (m, 2H), 6.76-6.74 (m, 2H), 6.68-6.64 (m, 4H), 1.69 (s, 6H) | 702.46 | 702.30 |
| 30 | 1 (C) | (9,9-dimethylfluorene with Ha₁ and Ha₂) | δ = 8.14 (d, 1H), 7.87-7.83 (m, 2H), 7.72-7.61 (m, 7H), 7.56-7.42 (m, 6H), 7.36 (d, 1H), 7.31-7.27 (m, 1H), 7.17-7.13 (m, 4H), 6.89-6.84 (m, 3H), 6.72 (d, 1H), 6.68-6.65 (m, 4H), 1.69 (s, 6H), 1.63 (s, 6H) | 742.61 | 742.33 |
| 31 | 1 (C) | (1,4-naphthalene with Ha₁ and Ha₂) | δ = 8.27 (d, 1H), 8.19 (d, 1H), 7.88 (dd, 1H), 7.85-7.78 (m, 2H), 7.71-7.60 (m, 5H), 7.54-7.42 (m, 7H), 7.34-7.27 (m, 2H), 7.18-7.05 (m, 5H), 6.85-6.81 (m, 2H), 6.77-6.05 (m, 4H), 1.70 (s, 6H) | 676.36 | 676.29 |
| 32 | 1 (C) | (2,6-naphthalene with Ha₁ and Ha₂) | δ = 8.08 (d, 2H), 7.88-7.75 (m, 5H), 7.71-7.59 (m, 5H), 7.49-7.27 (m, 7H), 7.19-7.13 (m, 4H), 7.06 (dd, 1H), 6.93-6.89 (m, 2H), 6.73-6.69 (m, 4H), 1.72 (s, 6H) | 676.34 | 676.29 |
| 33 | 1 (C) | (phenanthrene with Ha₁ and Ha₂) | δ = 8.43 (d, 1H), 8.26 (s, 1H), 8.18 (d, 2H), 7.93-7.79 (m, 3H), 7.69 (s, 1H), 7.64-7.51 (m, 6H), 7.44-7.30 (m, 6H), 7.23-7.19 (m, 1H), 7.12-7.09 (m, 4H), 7.01 (dd, 1H), 6.89-6.86 (m, 2H), 6.74-6.71 (m, 4H), 1.71 (s, 6H) | 726.48 | 726.30 |
| 34 | 1 (C) | (pyrene with Ha₁ and Ha₂) | δ = 8.34 (d, 1H), 8.12 (d, 1H), 7.96 (d, 1H), 7.89-7.73 (m, 6H), 7.63-7.41 (m, 8H), 7.38-7.24 (m, 5H), 7.15-7.11 (m, 4H), 7.05-7.01 (m, 2H), 6.83-6.79 (m, 4H), 1.69 (s, 6H) | 750.51 | 750.30 |

TABLE 1-continued

| Compound | Synthetic Pathway | Source material used, but not in original synthetic pathway | ¹H NMR (CDCl₃, 400 MHz) | MS/FAB found | calc. |
|---|---|---|---|---|---|
| 35 | 1 (C) | anthracene with Ha₁ and Ha₂ at 9,10-positions | δ = 8.36 (dd, 2H), 8.18 (d, 1H), 7.85 (d, 1H), 7.77 (d, 1H), 7.71-7.41 (m, 10H), 7.37-7.27 (m, 6H), 7.22-7.20 (m, 1H), 7.14-7.09 (m, 4H), 6.83-6.80 (m, 2H), 6.68-6.66 (m, 4H), 1.71 (s, 6H) | 726.42 | 726.30 |
| 37 | 1 (C) | N-phenyl carbazole with Ha₁ and Ha₂ | δ = 8.89 (s, 1H), 8.34-8.30 (m, 1H), 8.11 (d, 1H), 8.06 (dd, 1H), 7.89 (m, 1H), 7.75-7.69 (3H), 7.55-4.43 (m, 8H), 7.39-7.28 (m, 7H), 7.25-7.22 (m, 1H), 7.11-7.06 (m, 4H), 6.96-6.94 (m, 1H), 6.76-6.73 (m, 2H), 6.54-6.52 (m, 4H), 1.69 (s, 6H) | 791.52 | 791.33 |
| 38 | 1 (C) | spirobifluorene with Ha₁ and Ha₂ | δ = 8.26 (d, 1H), 7.98 (dd, 2H), 7.83-7.76 (m, 2H), 7.68-7.51 (m, 6H), 7.44-7.30 (m, 9H), 7.26-7.14 (m, 7H), 7.01-6.97 (m, 4H), 6.89-6.85 (m, 2H), 6.79 (d, 1H), 6.65-6.63 (m, 4H), 1.68 (s, 6H) | 864.53 | 864.35 |
| 39 | 1 (C) | pyridine with Ha₁ and Ha₂ | δ = 8.17 (d, 1H), 8.02 (s, 1H), 7.98 (d, 1H), 7.75-7.71 (m, 2H), 7.67 (d, 1H), 7.55-7.51 (m, 2H), 7.44-7.28 (m, 8H), 7.24-7.12 (m, 5H), 6.86-6.83 (m, 2H), 6.73-6.71 (m, 4H), 1.72 (s, 6H) | 627.35 | 627.27 |
| 40 | 1 (C) | pyrimidine with Ha₁ and Ha₂ | δ = 8.41 (s, 2H), 8.12 (d, 1H), 7.85-7.81 (m, 2H), 7.71 (d, 1H), 7.62 (d, 1H), 7.54-7.49 (m, 3H), 7.46-7.40 (m, 2H), 7.37-7.30 (m, 3H), 7.26-7.17 (m, 5H), 6.79 (dt, 2H), 6.71-6.67 (m, 4H), 1.68 (s, 6H) | 628.34 | 628.26 |
| 42 | 1 (C) | dibenzothiophene with Ha₁ and Ha₂ | δ = 8.44 (d, 1H), 8.36 (d, 1H), 8.12 (d, 1H), 7.94 (s, 1H), 7.90 (d, 1H), 7.85 (d, 1H), 7.74-7.56 (m, 5H), 7.48-7.36 (m, 6H), 7.23-7.17 (m, 5H), 7.04 (dd, 2H), 6.97-6.93 (m, 2H), 6.83-6.80 (m, 4H), 1.73 (s, 6H) | 732.46 | 732.26 |

TABLE 1-continued
| Compound | Synthetic Pathway | Source material used, but not in original synthetic pathway | $^1$H NMR (CDCl$_3$, 400 MHz) | MS/FAB found | calc. |
|---|---|---|---|---|---|
| 43 | 1 (C) | 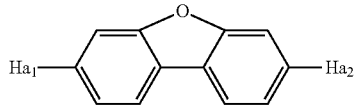 | δ = 8.16 (d, 1H), 8.06 (d, 1H), 8.00 (d, 1H), 7.83-7.81 (m, 2H), 7.77 (d, 1H), 7.65-7.59 (m, 3H), 7.55-7.51 (m, 2H), 7.47-7.43 (m, 2H), 7.38-7.31 (m, 4H), 7.25-7.23 (m, 1H), 7.18-7.15 (m, 5H), 6.99 (dd, 1H), 6.86-6.83 (m, 2H), 6.74-6.72 (m, 4H), 1.68 (s, 6H) | 716.36 | 716.28 |
| 46 | 1 (C) | 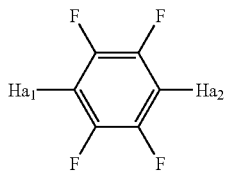 | δ = 8.09 (d, 1H), 7.87 (d, 1H), 7.79-7.77 (d, 2H), 7.69 (d, 1H), 7.58-7.53 (m, 2H), 7.49-7.43 (m, 3H), 7.41-7.32 (m, 3H), 7.24-7.22 (m, 1H), 7.18-7.10 (4H), 6.88 (dt, 2H), 6.83-6.80 (m, 4H), 1.67 (s, 6H) | 698.34 | 698.23 |
| 48 | 1 (C) | 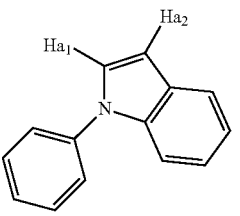 | δ = 8.14 (d, 1H), 7.93 (d, 1H), 7.83 (d, 1H), 7.78-7.69 (m, 4H), 7.65-7.59 (m, 4), 7.54-7.37 (m, 9H), 7.28-7.24 (m, 2H), 7.19-7.13 (m, 5), 7.03-7.01 (m, 2H), 6.81-6.78 (m, 4H), 1.70 (s, 6H) | 741.42 | 741.31 |
| 52 | 1 (C) | 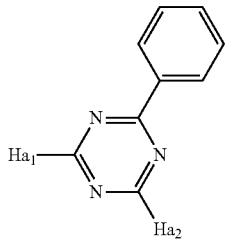 | δ = 8.96 (d, 2H), 8.21 (d, 1H), 7.91 (dd, 1H), 7.83 (d, 1H), 7.71-7.58 (m, 5H, 7.56-7.51 (m, 2H), 7.49-7.33 (m, 10H), 7.24-7.21 (m, 1H), 7.15-7.12 (m, 4H), 7.04 (dt, 2H), 1.68 (s, 6H) | 705.38 | 705.29 |
| 53 | 1 (C) | 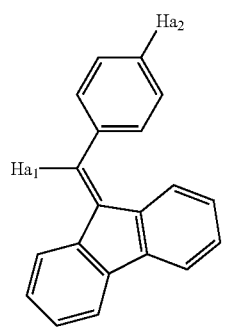 | δ = 8.32 (d, 2H), 8.16 (d, 1H), 7.92-7.86 (m, 4H), 7.82 (dd, 2H), 7.72 (d, 2H), 7.63-7.59 (m, 2H), 7.52-7.34 (m, 8H), 7.29-7.22 (m, 3H), 7.17-7.13 (m, 4H), 6.96-6.92 (m, 2H), 6.85 (dt, 2H), 6.76-6.73 (m, 4H), 1.71 (s, 6H) | 802.35 | 802.33 |

TABLE 1-continued

| Compound | Synthetic Pathway | Source material used, but not in original synthetic pathway | $^1$H NMR (CDCl$_3$, 400 MHz) | MS/FAB found | calc. |
|---|---|---|---|---|---|
| 54 | 1 (D) | (structure: bis(4-(trimethylsilyl)phenyl)amine) | δ = 8.15 (d, 1H), 7.93 (d, 1H), 7.84 (d, 1H), 7.72-7.67 (m, 2H), 7.63-7.54 (m, 4H), 7.47-7.36 (m, 10H), 7.25-7.21 (m, 1H), 7.18-7.12 (m, 2H), 6.89-6.85 (m, 4H), 1.69 (s, 6H), 0.24 (s, 18H) | 770.49 | 770.35 |
| 55 | 2 (E) | Bo$_1$—⌬—Ha$_1$ | δ = 8.13 (d, 1H), 7.97 (dd, 1H), 7.84 (d, 1H), 7.79-7.76 (m, 3H), 7.62-7.58 (m, 3H), 7.53-7.41 (m, 7H), 7.37-7.32 (m, 3H), 7.26-7.22 (m, 1H), 7.18-7.07 (m, 6H), 6.93 (dt, 2H), 6.79-6.76 (m, 4H), 1.70 (s, 6H) | 702.35 | 702.30 |
| 56 | 2 (E) | Bo$_1$—(naphthalene)—Ha$_1$ | δ = 8.14 (d, 1H), 8.03 (d, 1H), 7.99-7.95 (m, 2H), 7.89 (d, 1H), 7.79 (d, 1H), 7.72 (d, 1H), 7.65-7.60 (m, 5H), 7.49-7.31 (m, 7H), 7.26-7.21 (m, 1H), 7.19-7.09 (m, 8H), 6.98 (dt, 2H), 6.83-6.80 (m, 4H), 1.68 (s, 6H) | 752.41 | 752.32 |
| 58 | 2 (E) | Bo$_1$—(biphenyl)—Ha$_2$ | δ = 8.11 (d, 1H), 7.86-7.78 (m, 6H), 7.72-7.68 (m, 2H), 7.64-7.7.48 (m, 10H), 7.38-7.29 (m, 4H), 7.22-7.20 (m, 1H), 7.13-7.04 (m, 6H), 6.93 (dt, 2H), 6.84-6.81 (m, 4H), 1.69 (s, 6H) | 778.36 | 778.33 |
| 59 | 2 (E) | Bo$_1$—(9,9-dimethylfluorene)—Ha$_1$ | δ = 8.18 (d, 1H), 8.03 (d, 1H), 7.90-7.87 (m, 2H), 7.79-7.77 (m, 2H), 7.68 (d, 1H), 7.61-7.46 (m, 9H), 7.41-7.29 (m, 5H), 7.25-7.23 (m, 1H), 7.19-7.10 (m, 6H), 6.98 (dt, 2H), 6.88-6.85 (m, 4H), 1.75 (s, 6H), 1.65 (s, 6H) | 818.52 | 818.37 |

TABLE 1-continued
| Compound | Synthetic Pathway | Source material used, but not in original synthetic pathway | ¹H NMR (CDCl₃, 400 MHz) | MS/FAB found | calc. |
|---|---|---|---|---|---|
| 60 | 2 (E) | 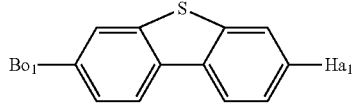 | δ = 8.31 (d, 1H), 8.19-8.16 (m, 2H), 8.08 (dd, 1H), 7.91 (s, 1H), 7.84 (d, 2H), 7.79 (d, 1H), 7.73 (d, 1H), 7.65-7.59 (m, 3H), 7.56-7.50 (m, 4H), 7.46-7.43 (m, 2H), 7.39-7.32 (m, 3H), 7.22-7.20 (m, 1H), 7.17-7.19 (m, 6H), 6.93-6.90 (m, 2H), 6.84-6.81 (m, 4H), 1.71 (s, 6H) | 808.46 | 808.29 |
| 61 | 2 (E) | 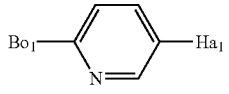 | δ = 8.88 (s, 1H), 8.27 (d, 1H), 8.11 (dd, 1H), 7.94 (dd, 1H), 7.86 (s, 1H), 7.83-7.81 (m, 2H), 7.76-7.70 (m, 2H), 7.63-7.53 (m, 6H), 7.43-7.37 (m, 3H), 7.26-7.24 (m, 1H), 7.17-7.06 (m, 6H), 6.97-6.94 (m, 2H), 6.87-6.84 (m, 4H), 1.69 (s, 6H) | 703.45 | 703.30 |
| 63 | 3 (B, C) | 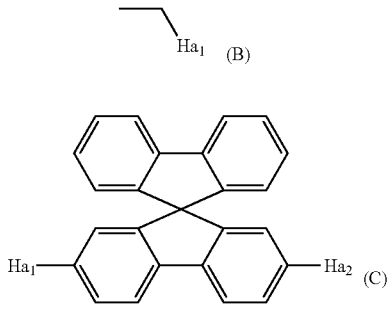 | δ = 8.23 (s, 1H), 8.06 (s, 1H), 7.90-7.86 (m, 2H), 7.78 (d, 1H), 7.66-7.56 (m, 4H), 7.46 (s, 1H), 7.42-7.34 (m, 5H), 7.27-7.14 (m, 11H), 7.09 (s, 1H), 6.99-6.94 (m, 3H), 6.84 (s, 1H), 6.79-6.76 (m, 4H), 4.15 (q, 2H), 1.62 (s, 6H), 1.34 (t, 3H) | 818.49 | 818.37 |
| 64 | 3 (C) | 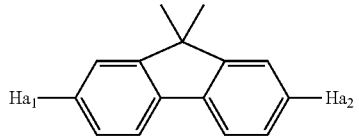 | δ = 8.19 (d, 1H), 7.92-7.90 (m, 2H), 7.77-7.57 (m, 10H), 7.51-7.35 (m, 5H), 7.21-7.14 (m, 4H), 7.05-7.01 (m, 3H), 6.98 (s, 1H), 6.87-6.85 (m, 4H), 1.63 (s, 6H), 1.59 (s, 6H) | 742.45 | 742.33 |
| 65 | 3 (C) | 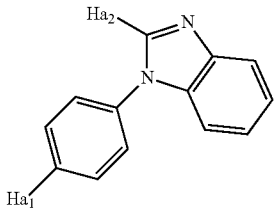 | δ = 8.21 (d, 1H), 7.95 (s, 1H), 7.86 (d, 1H), 7.83 (d, 1H), 7.75-7.73 (m, 2H), 7.63-7.56 (m, 7H), 7.50 (dt, 1H), 7.46-7.42 (m, 2H), 7.36-7.31 (m, 2H), 7.21-7.09 (m, 6H), 7.01 (dt, 2H), 6.97-6.94 (m, 2H), 6.85-6.82 (m, 4H), 1.61 (s, 6H) | 742.46 | 742.31 |

TABLE 1-continued

| Compound | Synthetic Pathway | Source material used, but not in original synthetic pathway | $^1$H NMR (CDCl$_3$, 400 MHz) | MS/FAB found | calc. |
|---|---|---|---|---|---|
| 67 | 3 (C) | (structure: 3-(4-Ha₁-phenyl)-2-Ha₂-imidazo[1,2-a]pyridine) | δ = 8.78 (d, 1H), 8.26 (d, 1H), 8.03 (d, 1H), 7.92 (s, 1H), 7.84-7.82 (m, 2H), 7.76 (s, 1H), 7.64 (s, 1H), 7.59-7.42 (m, 10H), 7.35 (dt, 1H), 7.23-7.19 (m, 4H), 7.06-7.02 (m, 3H), 6.97 (dt, 2H), 6.86-6.82 (, 4H), 1.60 (s, 6H) | 742.44 | 742.31 |
| 69 | 3 (C) | (structure: Ha₁-C₆H₄-O-C₆H₄-Ha₂) | δ = 8.25 (d, 1H), 7.92 (s, 1H), 7.88 (d, 1H), 7.74-7.70 (m, 2H), 7.67-7.57 (m, 7H), 7.49 (dt, 1H), 7.44-7.37 (m, 3H), 7.21-7.16 (m, 4H), 7.09-7.04 (m, 4H), 6.97 (dt, 2H), 6.92-6.89 (m, 2H), 6.86-6.82 (m, 4H), 1.61 (s, 6H) | 718.38 | 718.30 |
| 71 | 3 (C) | (structure: Ha₁-C₆H₄-C(=O)-C₆H₄-Ha₂) | δ = 8.22 (d, 1H), 7.98-7.95 (m, 2H), 7.91 (s, 1H), 7.89-7.83 (m, 3H), 7.76-7.69 (m, 4H), 7.63-7.57 (m, 5H), 7.52-7.37 (m, 4H), 7.29-7.24 (m, 4H), 7.13-7.11 (m, 2H), 7.04 (dt, 2H), 6.92-6.89 (m, 4H), 1.63 (s, 6H) | 730.42 | 730.30 |
| 74 | 3 (C) | (structure: Ha₁-C₆H₄-SO₂-C₆H₄-Ha₂) | δ = 8.22 (d, 1H), 7.92-7.89 (m, 2H), 7.87-7.71 (m, 6H), 7.64-7.60 (m, 2H), 7.58-7.50 (m, 5H), 7.45 (dt, 1H), 7.41-7.34 (m, 3H), 7.28-7.23 (m, 4H), 7.12-7.09 (m, 2H), 7.02 (dt, 2H), 6.91-6.87 (m, 4H), 1.61 (s, 6H) | 766.34 | 766.27 |
| 75 | 3 (B) | (structure: 1,3,5-triphenylbenzene with Ha₁) | δ = 8.25 (d, 1H), 8.21 (s, 1H), 8.01-7.96 (m, 5H), 7.85 (s, 1H), 7.75 (d, 1H), 7.66-7.54 (m, 9H), 7.46-7.40 (m, 6H), 7.28-7.14 (m, 6H), 7.04 (dt, 2H), 6.93-6.90 (m, 4H), 1.63 (s, 6H) | 788.39 | 778.33 |
| 76 | 3 (B) | (structure: 4,6-diphenyl-2-Ha₁-pyrimidine) | δ = 8.87 (d, 1H), 8.58 (s, 1H), 8.37-8.32 (m, 5H), 8.20 (d, 1H), 7.93 (s, 1H), 7.78 (d, 1H), 7.68-7.48 (m, 9H), 7.39-7.31 (m, 3H), 7.22-7.14 (m, 6H), 7.04-7.01 (m, 2H), 6.91-6.88 (m, 4H), 1.62 (s, 6H) | 780.46 | 780.33 |

TABLE 1-continued

| Compound | Synthetic Pathway | Source material used, but not in original synthetic pathway | $^1$H NMR (CDCl$_3$, 400 MHz) | MS/FAB found | calc. |
|---|---|---|---|---|---|
| 77 | 3 (B) | | δ = 8.92 (d, 1H), 8.78 (d, 4H), 8.47 (s, 1H), 8.32 (s, 1H), 8.24 (d, 1H), 7.88 (d, 1H), 7.79-7.68 (m, 6H), 7.63 (d, 2H), 7.55-7.48 (m, 3H), 7.43 (s, 1H), 7.28-7.19 (m, 6H), 7.09-7.03 (m, 2H), 6.95-6.92 (m, 4H), 1.60 (s, 6H) | 781.34 | 781.32 |
| 79 | 3 (B) | | δ = 8.19 (d, 1H), 8.11 (d, 1H), 7.92 (s, 1H), 7.88-7.85 (m, 3H), 7.75 (s, 1H), 7.69 (d, 1H), 7.65-7.42 (m, 10H), 7.24-7.16 (m, 6H), 7.08 (dt, 2H), 7.01-6.98 (m, 4H), 11.63 (s, 6H) | 716.34 | 716.28 |
| 80 | 3 (B) | | δ = 8.34 (d, 1H), 8.24 (d, 1H), 8.00 (d, 1H), 7.99 (s, 1H), 7.92 (s, 1H), 7.84 (d, 1H), 7.80-7.42 (m, 12H), 7.29-7.18 (m, 6H), 7.10 (dt, 2H), 7.02-6.99 (m, 4H), 1.62 (s, 6H) | 732.38 | 732.26 |
| 82 | 3 (B) | | δ = 8.69 (d, 1H), 8.55 (s, 1H), 8.31 (s, 1H), 8.23 (d, 1H), 7.88 (d, 1H), 7.80 (d, 1H), 7.76-7.51 (m, 11H), 7.44-7.38 (m, 2H), 7.30-7.18 (m, 7H), 7.09-7.04 (m, 2H), 7.0-6.8 (m, 4H), 1.59 (s, 6H) | 742.39 | 742.31 |
| 85 | 3 (B) | | δ = 8.25 (d, 1H), 7.93 (s, 1H), 7.89 (d, 1H), 7.75 (s, 1H), 7.70 (d, 1H), 7.66-7.60 (m, 3H), 7.51-7.40 (m, 3H), 7.32-7.20 (m, 12H), 7.11-7.09 (m, 2H), 7.03-6.99 (m, 4H), 6.91-6.86 (m, 8H), 1.64 (s, 6H) | 793.48 | 793.35 |
| 86 | 3 (B) | | δ = 8.24 (d, 1H), 7.89 (s, 1H), 7.83 (d, 1H), 7.75-7.68 (m, 4H), 7.64-7.56 (m, 3H), 7.52-7.39 (m, 5H), 7.28-7.17 (m, 6H), 7.06 (dt, 2H), 6.99-6.95 (m, 4H), 1.62 (s, 6H), 0.25 (s, 9H) | 698.37 | 698.31 |

TABLE 1-continued

| Compound | Synthetic Pathway | Source material used, but not in original synthetic pathway | ¹H NMR (CDCl₃, 400 MHz) | MS/FAB found | calc. |
|---|---|---|---|---|---|
| 87 | 3 (B) | (carbazole structure with Ha₁, N-phenyl) | δ = 8.47 (d, 1H), 8.27 (d, 1H), 8.08 (s, 1H), 7.97 (s, 1H), 7.84 (d, 1H), 7.74-7.53 (m, 9H), 7.52-7.36 (m, 9H), 7.24-7.15 (m, 6H), 7.06-7.03 (m, 2H), 6.98-6.95 (m, 4H), 1.63 (s, 6H) | 791.39 | 791.33 |
| 88 | 3 (B, D) | (B) carbazole structure with Ha₁, N-phenyl; (D) N-phenyl-2-aminopyridine — Specifically, D may be A1. | δ = 8.46 (d, 1H), 8.26 (d, 1H), 8.22 (d, 1H), 7.99 (s, 1H), 7.89 (s, 1H), 7.80 (d, 1H), 7.71-7.7.29 (m, 22H), 7.25-7.16 (m, 2H), 7.09 (dt, 1H), 7.01 (dt, 1H), 6.94-6.92 (m, 2H), 1.63 (s, 6H) | 792.41 | 792.33 |
| 89 | 4 (E) | (tetrafluorobenzene with Bo₁ and Ha₁) | δ = 8.26 (d, 1H), 8.04 (d, 1H), 7.98-7.96 (m, 1H), 7.92 (s, 1H), 7.66-7.58 (m, 9H), 7.51-7.36 (m, 3H), 7.30-7.21 (m, 6H), 7.17-7.09 (m, 2H), 7.02-6.99 (m, 4H), 1.61 (s, 6H) | 774.34 | 774.27 |
| 92 | 4 (E) | (dibenzofuran with Bo₁ and Ha₁) | δ = 8.26 (d, 1H), 8.14 (d, 1H), 8.02 (d, 1H), 7.93-7.76 (m, 5H), 7.69 (s, 1H), 7.66 (s, 1H), 7.62 (d, 1H), 7.58-7.44 (m, 9H), 7.41-7.36 (m, 2H), 7.23-7.13 (m, 6H), 7.09-7.05 (m, 2H), 6.98-6.94 (m, 4H), 1.63 (s, 6H) | 792.42 | 792.31 |

In Table 1, Ha₁ and Ha₂ may be each independently iodine (I) or bromine (Br), and Bo1 may be —B(OH)₂ or

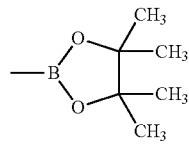

Example 1

A 15 Ω/cm² (1200 Å) ITO glass substrate (available from Corning Co.) was cut to a size of 50 mm×50 mm×0.7 mm, ultrasonically washed with isopropyl alcohol for 5 minutes and then with pure water for 5 minutes, and washed again with UV ozone for 30 minutes. 2-TNATA was vacuum-deposited on the ITO glass substrate to form an HIL having a thickness of 600 Å on the anode, and then NPB was vacuum-deposited on the HIL to form an HTL having a thickness of 300 Å. 98 wt % of ADN as a blue fluorescent host and 2 wt % of Compound 3 above as a fluorescent dopant were deposited on the HTL to form an EML having a thickness of 300 Å. Alq₃ was vacuum-deposited on the EML to form an ETL having a thickness of 300 Å. LiF was vacuum-deposited on the ETL to form an ELL having a thickness of 10 Å and Al was vacuum-deposited on the EIL to form a cathode having a thickness of 3000 Å, thereby completing the manufacture of an organic light-emitting device.

Example 2

An organic light-emitting device was manufactured in the same manner as in Example 1, except that Compound 7, instead of Compound 3, was used to form the EML.

Example 3

An organic light-emitting device was manufactured in the same manner as in Example 1, except that Compound 14, instead of Compound 3, was used to form the EML.

Example 4

An organic light-emitting device was manufactured in the same manner as in Example 1, except that Compound 18, instead of Compound 3, was used to form the EML.

Example 5

An organic light-emitting device was manufactured in the same manner as in Example 1, except that Compound 22, instead of Compound 3, was used to form the EML.

Example 6

An organic light-emitting device was manufactured in the same manner as in Example 1, except that Compound 38, instead of Compound 3, was used to form the EML.

Example 7

An organic light-emitting device was manufactured in the same manner as in Example 1, except that Compound 55, instead of Compound 3, was used to form the EML.

Example 8

An organic light-emitting device was manufactured in the same manner as in Example 1, except that Compound 64, instead of Compound 3, was used to form the EML.

Example 9

An organic light-emitting device was manufactured in the same manner as in Example 1, except that Compound 85, instead of Compound 3, was used to form the EML.

Comparative Example 1

An organic light-emitting device was manufactured in the same manner as in Example 1, except that DPAVBi, instead of Compound 3, was used to form the EML.

Evaluation Example

Driving voltages, current densities, luminance, efficiencies, emitting-light colors, half lifetime of the organic light-emitting devices of Examples 1 to 9 and Comparative Example 1 were measured using a PR650 (Spectroscan) Source Measurement Unit (available from Photo Research, Inc.). The results are shown in Table 2 below:

TABLE 2

| | EML host | EML dopant | Driving voltage (V) | Current density (mA/cm²) | Luminance (cd/m²) | Efficiency (cd/A) | Emitting light color | Half-life span (hr @ 100 mA/cm²) |
|---|---|---|---|---|---|---|---|---|
| Example 1 | ADN | Compound 3 | 6.31 | 50 | 3,380 | 6.76 | blue | 287 |
| Example 2 | ADN | Compound 7 | 6.35 | 50 | 3,245 | 6.49 | blue | 312 |
| Example 3 | ADN | Compound 14 | 6.34 | 50 | 3,305 | 6.61 | blue | 240 |
| Example 4 | ADN | Compound 18 | 6.28 | 50 | 3,290 | 6.58 | blue | 259 |
| Example 5 | ADN | Compound 22 | 6.30 | 50 | 3,425 | 6.85 | blue | 248 |
| Example 6 | ADN | Compound 38 | 6.35 | 50 | 3,275 | 6.55 | blue | 276 |
| Example 7 | ADN | Compound 55 | 6.41 | 50 | 3,368 | 6.73 | bluish | 196 |
| Example 8 | ADN | Compound 64 | 6.34 | 50 | 3,135 | 6.27 | blue | 217 |
| Example 9 | ADN | Compound 85 | 6.12 | 50 | 2,935 | 5.87 | blue | 258 |
| Comparative Example 1 | ADN | DPAVBi | 7.35 | 50 | 2,065 | 4.13 | blue | 145 |

Referring to Table 2, the organic light-emitting devices of Examples 1 to 9 were found to have better performance in terms of driving voltage, luminance, efficiency, and lifetime, as compared with the organic light-emitting device of Comparative Example 1.

As described above, an organic light-emitting device including the heterocyclic compound according to embodiments of the present invention may have a high performance, for example, a low driving voltage, a high luminance, a high efficiency, and a long lifetime.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A heterocyclic compound represented by Formula 1 or Formula 2 below:

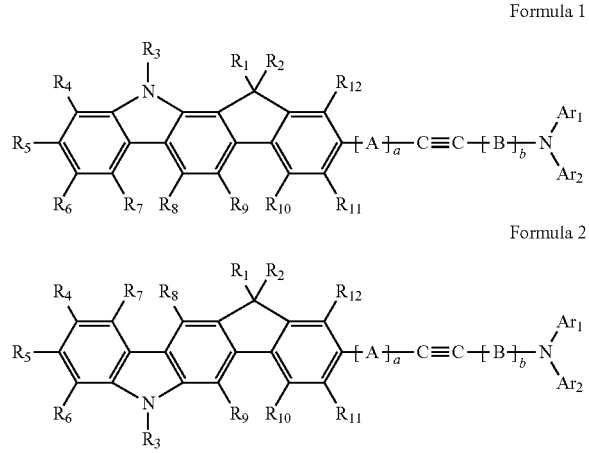

Formula 1

Formula 2 wherein, in Formulae 1 and 2, $Ar_1$ and $Ar_2$ are each independently a substituted or unsubstituted $C_6$-$C_{30}$ aryl group or a substituted or unsubstituted $C_3$-$C_{30}$ heteroaryl group;

A and B are a divalent linker, and each independently one of $-Si(R_{13})(R_{14})-$, $-C(=C(R_{15})(R_{16}))-$, $-O-$, $-S-$, $-C(=O)-$, $-P(=O)(R_{17})-$, $-S(=O)-$, $-(O=)S(=O)-$, a substituted or unsubstituted $C_6$-$C_{30}$ arylene group, or a substituted or unsubstituted $C_3$-$C_{30}$ heteroarylene group;

$R_1$ to $R_{17}$ are each independently a hydrogen atom, a deuterium atom, a halogen atom, a hydroxyl group, a cyano group, a nitro group, a carboxyl group, a substituted or unsubstituted $C_1$-$C_{30}$ alkyl group, a substituted or unsubstituted $C_2$-$C_{30}$ alkenyl group, a substituted or unsubstituted $C_2$-$C_{30}$ alkynyl group, a substituted or unsubstituted $C_1$-$C_{30}$ alkoxy group, a substituted or unsubstituted $C_3$-$C_{30}$ cycloalkyl group, a substituted or unsubstituted $C_3$-$C_{30}$ cycloalkenyl group, a substituted or unsubstituted $C_6$-$C_{30}$ aryl group, a substituted or unsubstituted $C_2$-$C_{30}$ heteroaryl group, a substituted or unsubstituted $C_6$-$C_{30}$ aryloxy group, a substituted or unsubstituted $C_6$-$C_{30}$ arylthio group, or an amino group substituted with a substituted or unsubstituted $C_6$-$C_{30}$ aryl group; and a is an integer from 0 to 3, and b is an integer from 0 to 3, wherein if a is 2 or greater, the two or more A are identical to or different from each other, and if b is 2 or greater, the two or more B are identical to or different from each other.

2. The heterocyclic compound of claim 1, wherein $R_1$ to $R_{17}$ are each independently a hydrogen atom, a deuterium atom, a halogen atom, a hydroxyl group, a cyano group, a nitro group, a carboxyl group, a substituted or unsubstituted methyl group, a substituted or unsubstituted ethyl group, a substituted or unsubstituted propyl group, a substituted or unsubstituted butyl group, a substituted or unsubstituted pentyl group, a substituted or unsubstituted phenyl group, a substituted or unsubstituted biphenyl group, a substituted or unsubstituted terphenyl group, a substituted or unsubstituted naphthyl group, a substituted or unsubstituted phenoxy group, a substituted or unsubstituted fluorenyl group, a substituted or unsubstituted spirofluorenyl group, a substituted or unsubstituted carbozolyl group, a substituted or unsubstituted phenanthrenyl group, a substituted or unsubstituted pyranyl group, a substituted or unsubstituted pyridinyl group, a substituted or unsubstituted pyrimidinyl group, a substituted or unsubstituted diazinyl group, a substituted or unsubstituted triazinyl group, a substituted or unsubstituted quinolinyl group, a substituted or unsubstituted benzoimidazolyl group, a substituted or unsubstituted benzoxazolyl group, a substituted or unsubstituted pentalenyl group, a substituted or unsubstituted indenyl group, a substituted or unsubstituted azulenyl group, a substituted or unsubstituted heptalenyl group, a substituted or unsubstituted indacenyl group, a substituted or unsubstituted acenaphthyl group, a substituted or unsubstituted phenalenyl group, a substituted or unsubstituted phenanthridinyl group, a substituted or unsubstituted anthryl group, a substituted or unsubstituted fluoranthenyl group, a substituted or unsubstituted triphenylenyl group, a substituted or unsubstituted pyrenyl group, a substituted or unsubstituted chrysenyl group, a substituted or unsubstituted naphthacenyl group, a substituted or unsubstituted picenyl group, a substituted or unsubstituted perylenyl group, a substituted or unsubstituted pentaphenyl group, a substituted or unsubstituted hexacenyl group, a substituted or unsubstituted pyrrolyl group, a substituted or unsubstituted imidazolinyl group, a substituted or unsubstituted pyrazolyl group, a substituted or unsubstituted imidazopyridinyl group, a substituted or unsubstituted pyrazinyl group, a substituted or unsubstituted imidazopyrimidinyl group, a substituted or unsubstituted pyridazinyl group, a substituted or unsubstituted indolyl group, a substituted or unsubstituted indolizinyl group, a substituted or unsubstituted isoindolizinyl group, a substituted or unsubstituted pyridoindolizinyl group, a substituted or unsubstituted indazolyl group, a substituted or unsubstituted carbazolyl group, a substituted or unsubstituted purinyl group, a substituted or unsubstituted benzoquinolinyl group, a substituted or unsubstituted phthalazinyl group, a substituted or unsubstituted naphthyridinyl group, a substituted or unsubstituted quinoxalinyl group, a substituted or unsubstituted quinazolinyl group, a substituted or unsubstituted cinnolinyl group, a substituted or unsubstituted phenazinyl group, a substituted or unsubstituted furanyl group, a substituted or unsubstituted benzofuranyl group, a substituted or unsubstituted dibenzofuranyl group, a substituted or unsubstituted thiophenyl group, a substituted or unsubstituted benzothiophenyl group, a substituted or unsubstituted dibenzothiophenyl group, a substituted or unsubstituted thiazolyl group, a substituted or unsubstituted isothiazolyl group, a substituted or unsubstituted benzothiazolyl group, a substituted or unsubstituted oxazolyl group, a substituted or unsubstituted isoxazolyl group, a substituted or unsubstituted oxadiazolyl group, a substituted or unsubstituted triazolyl group, or a substituted or unsubstituted tetrazolyl group.

3. The heterocyclic compound of claim 1, wherein $R_1$ to $R_{17}$ are each independently selected from the group consisting of a hydrogen atom, a deuterium atom, a halogen atom, a substituted or unsubstituted methyl group, a substituted or unsubstituted propyl group, a substituted or unsubstituted butyl group, and groups represented by Formulae 2A to 2P below:

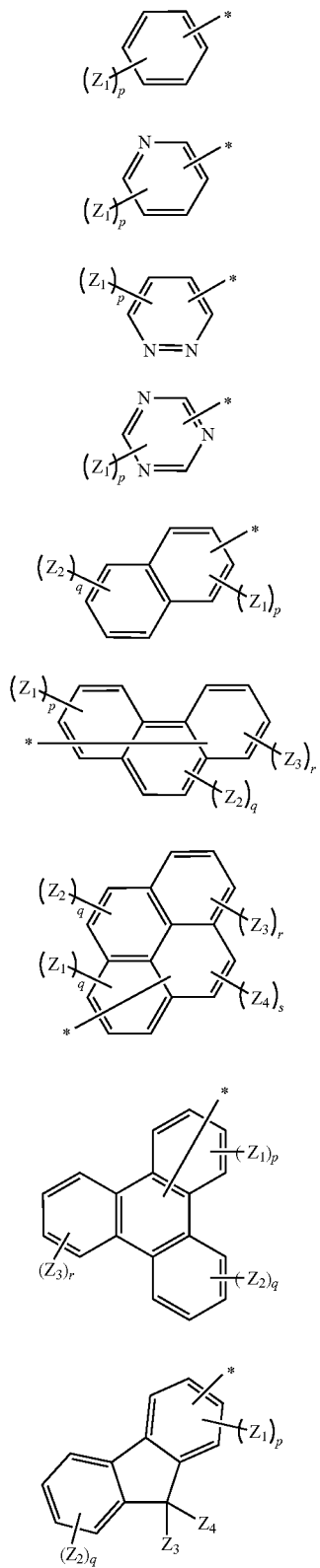

Formula 2A

Formula 2B

Formula 2C

Formula 2D

Formula 2E

Formula 2F

Formula 2G

Formula 2H

Formula 2I

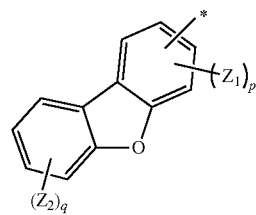

Formula 2J

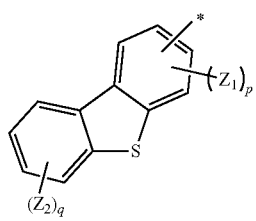

Formula 2K

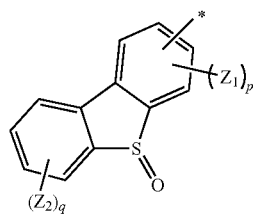

Formula 2L

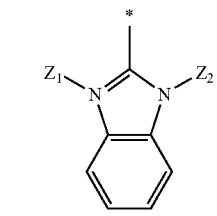

Formula 2M

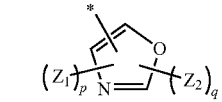

Formula 2N

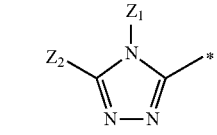

Formula 2O

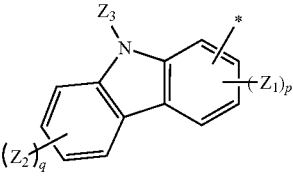

Formula 2P wherein, in Formulae 2A-2P, $Z_1$, $Z_2$, $Z_3$, and $Z_4$ are each independently one of a hydrogen atom, a deuterium atom, a halogen atom, a hydroxyl group, a cyano group, a substituted or unsubstituted methyl group, a substituted or unsubstituted ethyl group, a substituted or unsubstituted propyl group, a substituted or unsubstituted butyl group, a substituted or unsubstituted methoxy group, a substituted or unsubstituted ethoxy group, a substituted or unsubstituted ethenyl group, a substituted or unsubstituted phenyl group, a substituted or unsubstituted naphthyl group, a substituted or unsubstituted anthryl group, a substituted or unsubstituted pyridinyl group, a substituted or unsubstituted quinolinyl group, a group represented by —N($Q_1$)($Q_2$), and a group represented by —Si($Q_2$)($Q_4$)($Q_5$); and $Q_1$ to $Q_5$ are each independently one of a hydrogen atom, a deuterium atom, a halogen atom, a hydroxyl group, a cyano group, a nitro group, a carboxyl group, a substituted or unsubstituted $C_1$-$C_{30}$ alkyl group, a substituted or unsubstituted $C_2$-$C_{30}$ alkenyl group, a substituted or unsubstituted $C_2$-$C_{30}$ alkynyl group, a substituted or unsubstituted $C_1$-$C_{30}$ alkoxy group, a substituted or unsubstituted $C_3$-$C_{30}$ cycloalkyl group, a substituted or unsubstituted $C_3$-$C_{30}$ cycloalkenyl group, a substituted or unsubstituted $C_6$-$C_{30}$ aryl group, a substituted or unsubstituted $C_3$-$C_{30}$ heteroaryl group, a substituted or unsubstituted $C_6$-$C_{30}$ aryloxy group, and a substituted or unsubstituted $C_6$-$C_{30}$ arylthio group; a plurality of each of $Z_1$, $Z_2$, $Z_3$, and $Z_4$ are the same as or different from each other; p, q, r and s are an integer from 1 to 5; and * indicates a binding site.

4. The heterocyclic compound of claim 1, wherein $R_1$ to $R_{17}$ are each independently selected from the group consisting of a hydrogen atom, a deuterium atom, a halogen atom, a substituted or unsubstituted methyl group, a substituted or unsubstituted propyl group, a substituted or unsubstituted tert-butyl group, and groups represented by Formulae 3A to 3U below:

Formula 3A

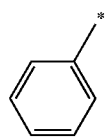

Formula 3B

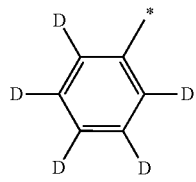

Formula 3C

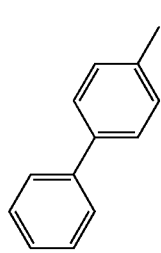

Formula 3D

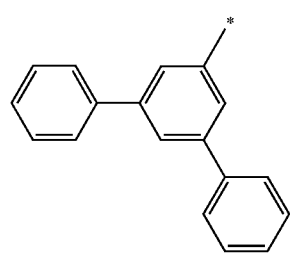

-continued

Formula 3E

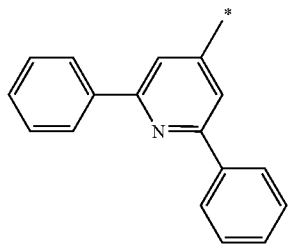

Formula 3F

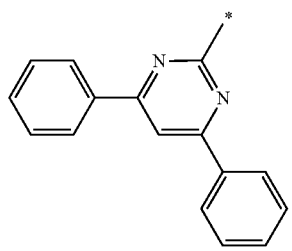

Formula 3G

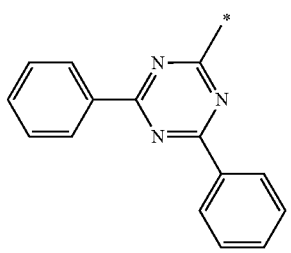

Formula 3H

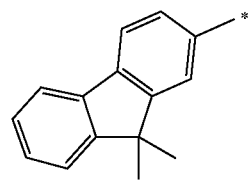

Formula 3I

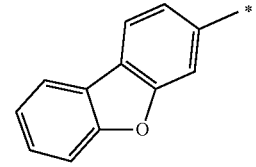

Formula 3J

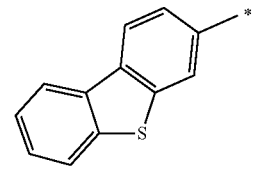

Formula 3K

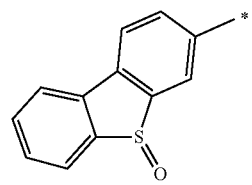

-continued

Formula 3L
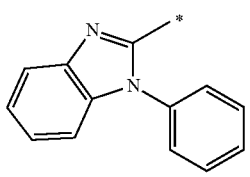

Formula 3M
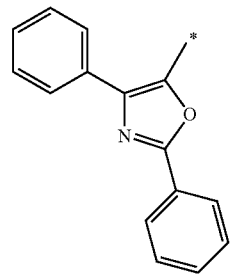

Formula 3N
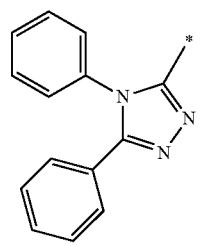

Formula 3O
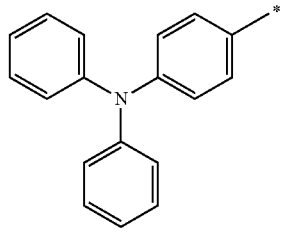

Formula 3P
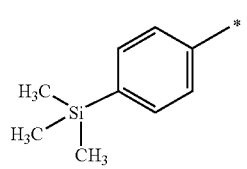

Formula 3Q
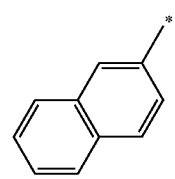

Formula 3R
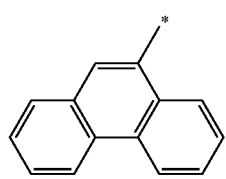

-continued

Formula 3S
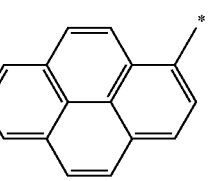

Formula 3T
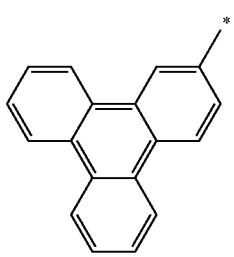

Formula 3U
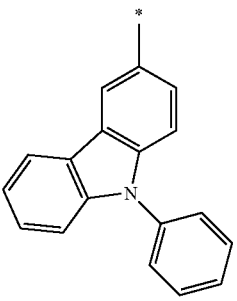

wherein, in Formulae 3A to 3U, * indicates a binding site; and D is a deuterium atom.

5. The heterocyclic compound of claim 1, wherein $Ar_1$ and $Ar_2$ are each independently one of a substituted or unsubstituted phenyl group, a substituted or unsubstituted naphthyl group, a substituted or unsubstituted phenanthrenyl group, a substituted or unsubstituted pyrenyl group, a substituted or unsubstituted anthryl group, a substituted or unsubstituted fluorenyl group, a substituted or unsubstituted spirofluorenyl group, a substituted or unsubstituted carbazolyl group, a substituted or unsubstituted pyridinyl group, a substituted or unsubstituted quinolinyl group, a substituted or unsubstituted pyrimidinyl group, a substituted or unsubstituted triazinyl group, a substituted or unsubstituted chrysenyl group, a substituted or unsubstituted perylenyl group, and a substituted or unsubstituted oxadiazolyl group.

6. The heterocyclic compound of claim 1, wherein $Ar_1$ and $Ar_2$ are each independently one of the groups represented by Formulae 4A to 4G below:

Formula 4A
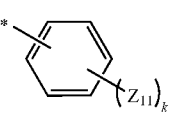

Formula 4B
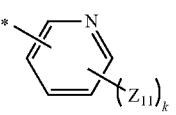

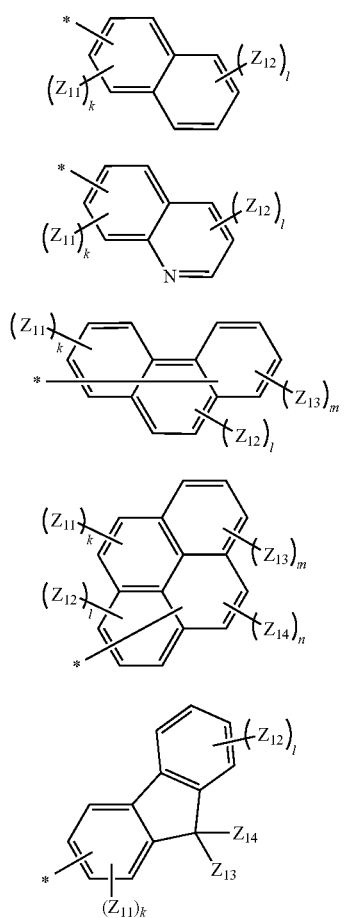

wherein, in Formulae 4A to 4G, $Z_{11}$, $Z_{12}$, $Z_{13}$, and $Z_{14}$ are each independently one of a hydrogen atom, a deuterium atom, a halogen atom, a hydroxyl group, a cyano group, a substituted or unsubstituted methyl group, a substituted or unsubstituted ethyl group, a substituted or unsubstituted propyl group, a substituted or unsubstituted butyl group, a substituted or unsubstituted methoxy group, a substituted or unsubstituted ethoxy group, a substituted or unsubstituted phenyl group, a substituted or unsubstituted naphthyl group, a substituted or unsubstituted anthryl group, a substituted or unsubstituted pyridinyl group, and a substituted or unsubstituted quinolinyl group; a plurality of each of $Z_{11}$, $Z_{12}$, $Z_{13}$, and $Z_{14}$ are the same as or different from each other; k and l are an integer from 1 to 5; m is an integer from 1 to 4; n is an integer from 1 to 2, and * indicates a binding site.

7. The heterocyclic compound of claim 1, wherein $Ar_1$ and $Ar_2$ are each independently one of the groups represented by Formulae 5A to 5O below:

-continued

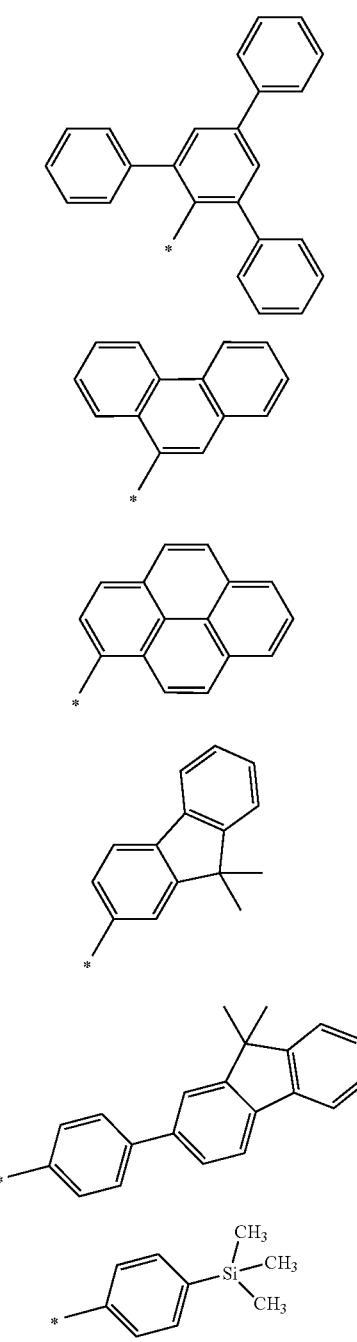

Formula 5J

Formula 5K

Formula 5L

Formula 5M

Formula 5N

Formula 5O wherein, in Formulae 5A to 5O, * indicates a binding site; and D is a deuterium atom.

8. The heterocyclic compound of claim 1, wherein A and B are each independently one of —O—, —S—, —C(=O)—, —S(=O)—, —(O=)S(=O)—, and groups represented by Formulae 6A to 6Z:

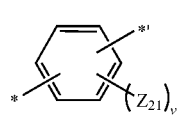

Formula 6A

-continued

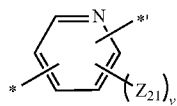

Formula 6B

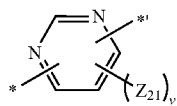

Formula 6C

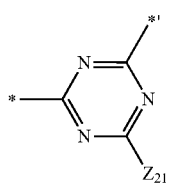

Formula 6D

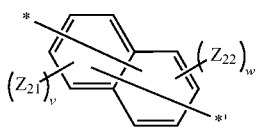

Formula 6E

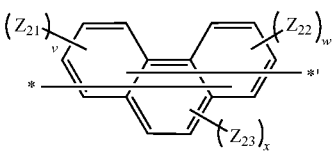

Formula 6F

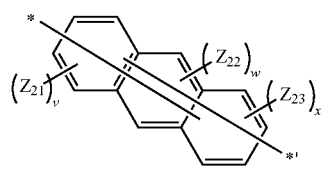

Formula 6G

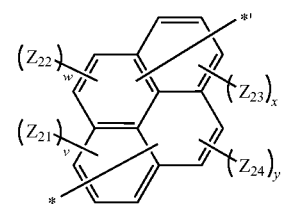

Formula 6H

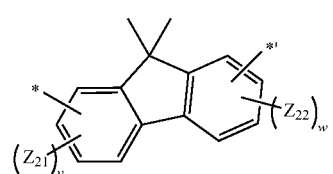

Formula 6I

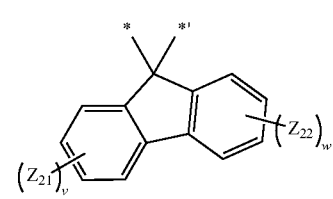

Formula 6J

-continued

Formula 6K

Formula 6L

Formula 6M

Formula 6N

Formula 6O

Formula 6P

Formula 6Q

-continued

Formula 6R

Formula 6S

Formula 6T

Formula 6U

Formula 6V

Formula 6W

Formula 6X

Formula 6Y

Formula 6Z wherein, in Formulae 6A to 6Z, $Z_{21}$, $Z_{22}$, $Z_{23}$, and $Z_{24}$ are each independently one of a hydrogen atom, a deuterium atom, a halogen atom, a hydroxyl group, a cyano group, a substituted or unsubstituted methyl group, a substituted or unsubstituted ethyl group, a substituted or unsubstituted propyl group, a substituted or unsubstituted butyl group, a substituted or unsubstituted methoxy group, a substituted or unsubstituted ethoxy group, a substituted or unsubstituted phenyl group, a substituted or unsubstituted silyl group, a substituted or unsubstituted fluorenyl group, a substituted or unsubstituted naphthyl group, and a substituted or unsubstituted pyridinyl group; a plurality of each of $Z_{21}$, $Z_{22}$, $Z_{23}$, and $Z_{24}$ are the same as or different from each other; v and w are an integer from 1 to 4; x and y are an integer from 1 to 3; and * and *' indicate a binding site.

9. The heterocyclic compound of claim 8, wherein A and B are each independently one of —O—, —S—, —C(=O)—, —S(=O)—, —(O=)S(=O)—, and groups represented by Formulae 7A to 7AE:

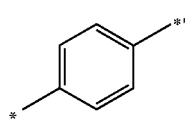

Formula 7A

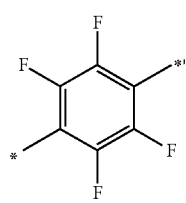

Formula 7B

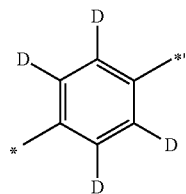

Formula 7C

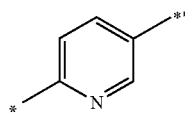

Formula 7D

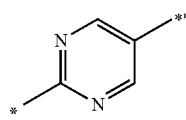

Formula 7E

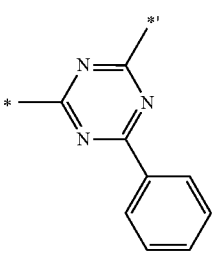

Formula 7F

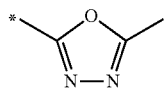

Formula 7G

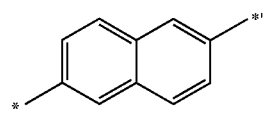

Formula 7H

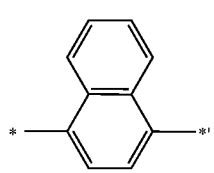

Formula 7I

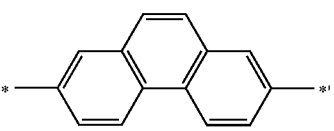

Formula 7J

Formula 7K

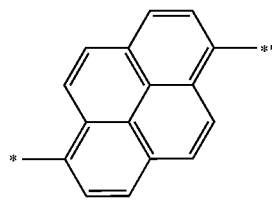

Formula 7L

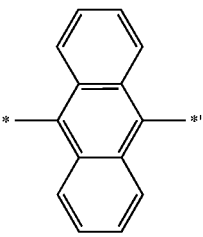

Formula 7M

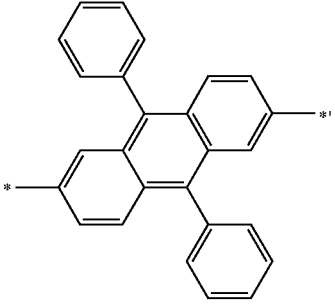

Formula 7N

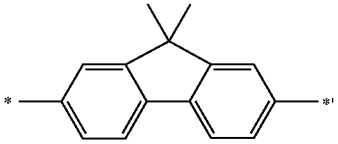

Formula 7O

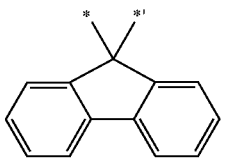

-continued
Formula 7P
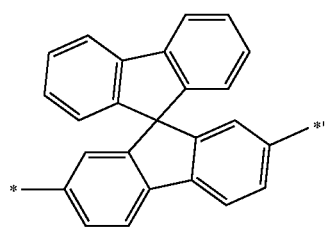
Formula 7Q
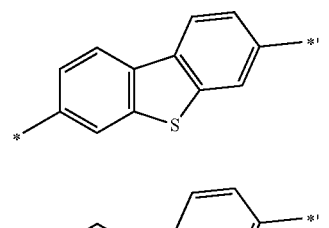
Formula 7R
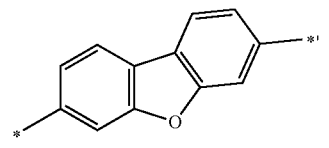
Formula 7S
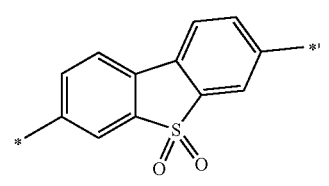
Formula 7T
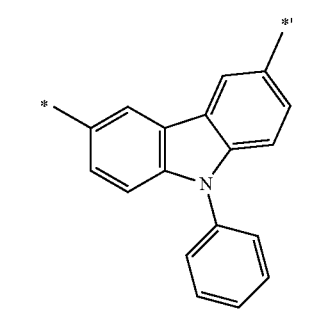
Formula 7U
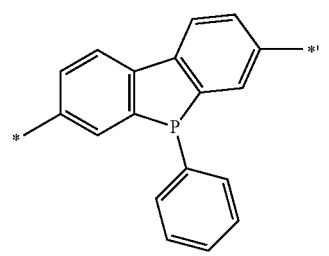
Formula 7V
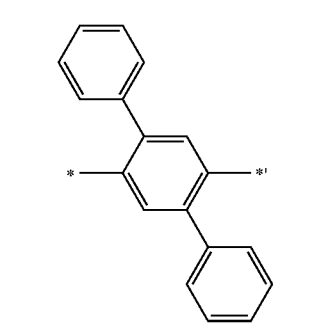
Formula 7W
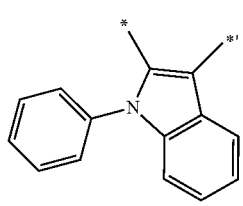
Formula 7X
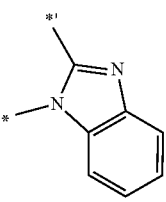
Formula 7Y
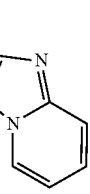
Formula 7Z
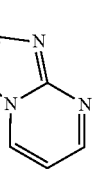
Formula 7AA
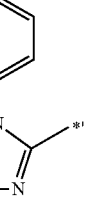
Formula 7AB
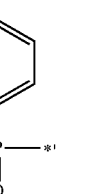
Formula 7AC
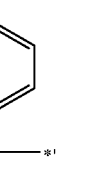

-continued
Formula 7AD
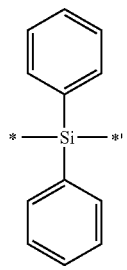
Formula 7AE
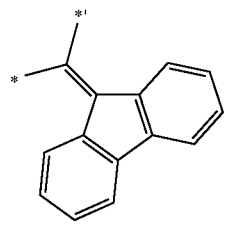
wherein, in Formulae 7A to 7AE, * and *' indicate a binding site; and D is a deuterium atom.
10. The heterocyclic compound of claim 1, wherein the heterocyclic compound represented by Formula 1 or Formula 2 comprises at least one of the compounds represented by Formulae 3, 7, 14, 18, 22, 38, 55, 64, and 85 below:
Formula 3
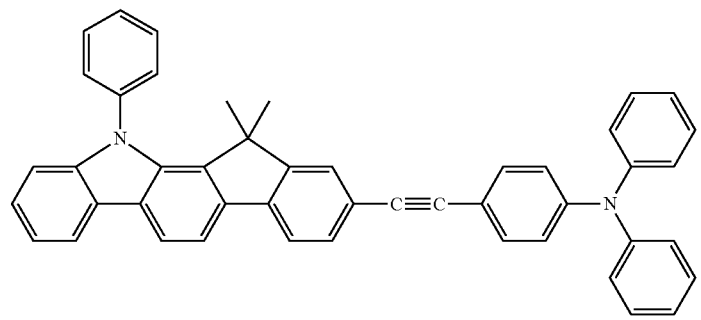
Formula 7
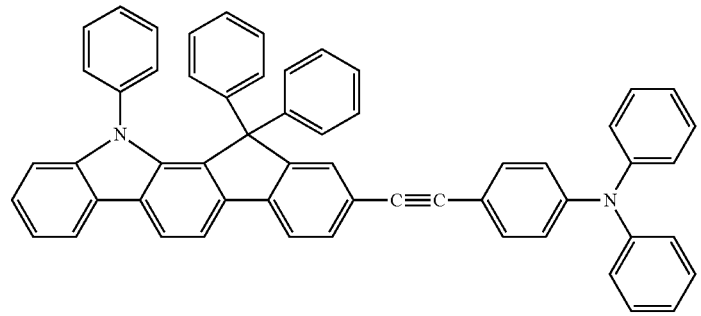
Formula 14
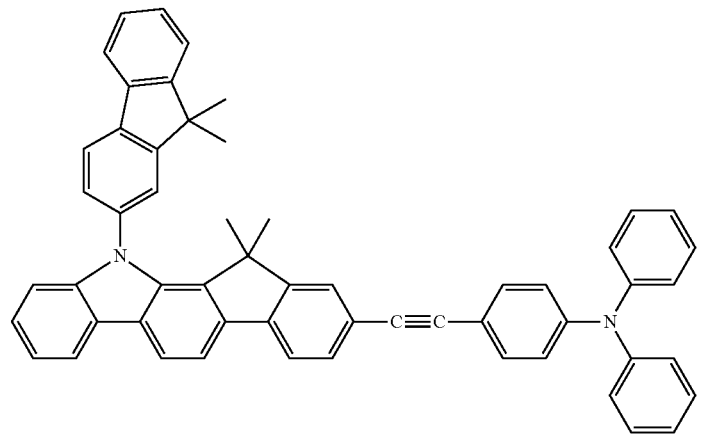

-continued
Formula 18
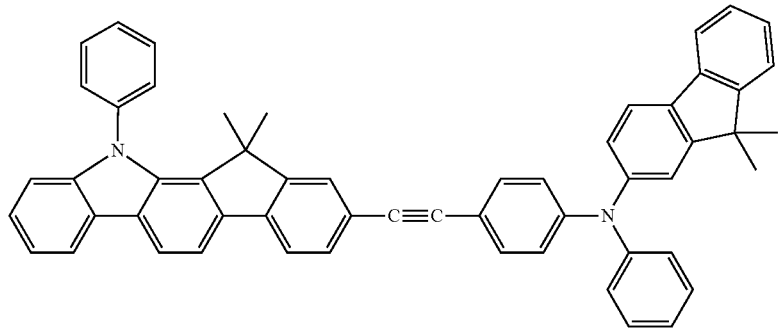
Formula 22
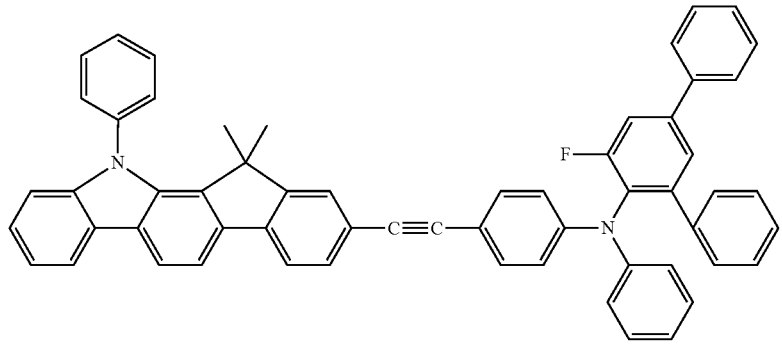
Formula 38
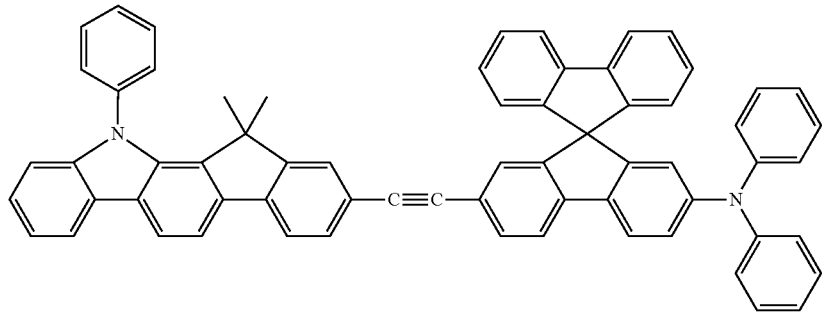
Formula 55
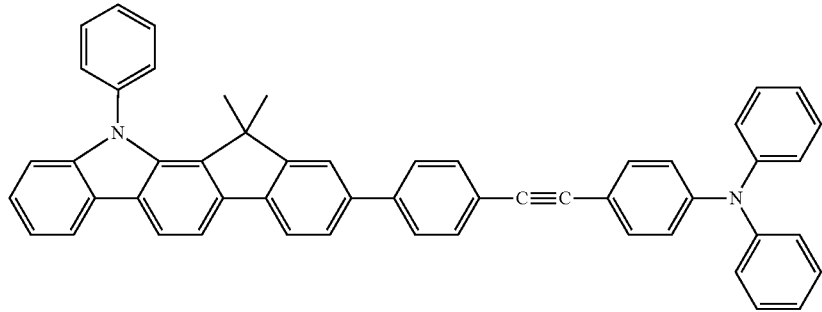
Formula 64
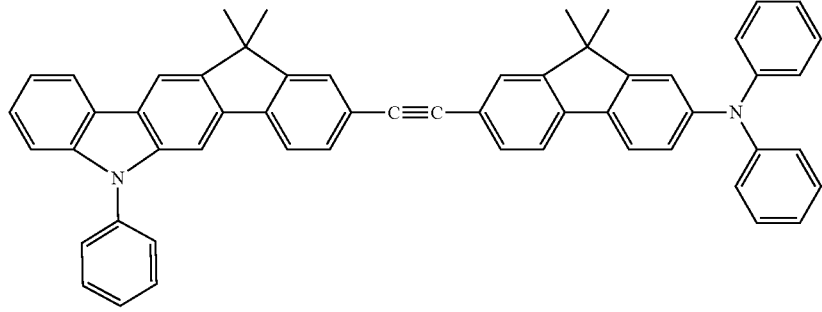

-continued

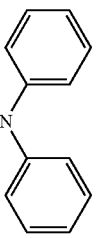

Formula 85

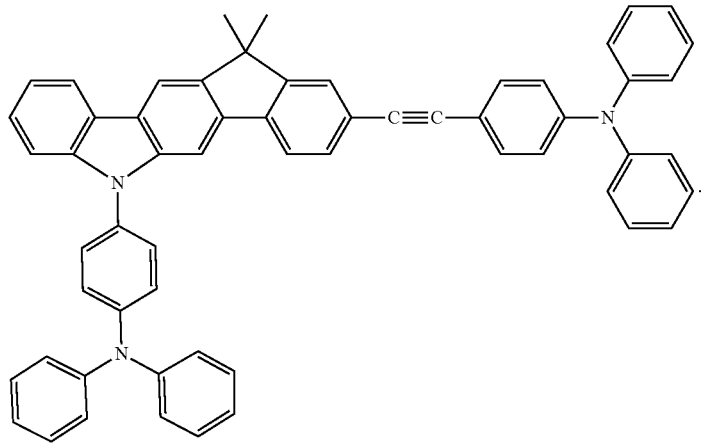

11. An organic light-emitting device comprising:
a first electrode;
a second electrode disposed opposite to the first electrode; and
an organic layer disposed between the first electrode and the second electrode, wherein the organic layer comprising at least one layer and at least one of the heterocyclic compounds represented by Formula 1 and Formula 2 of claim 1.

12. The organic light-emitting device of claim 11, wherein the organic layer comprises at least one layer of an emission layer, a hole injection layer, a hole transport layer, and a hole injection and transport layer having both hole injection and hole transport capabilities, and at least one layer of the emission layer, the hole injection layer, the hole transport layer, and the hole injection and transport layer comprises at least one of the heterocyclic compounds represented by Formula 1 and Formula 2.

13. The organic light-emitting device of claim 12, wherein the organic layer comprises an emission layer comprising a host and a dopant, and the heterocyclic compound is a fluorescent host, a phosphorescent host, or a fluorescent dopant of the emission layer.

14. The organic light-emitting device of claim 12, wherein the organic layer comprises an emission layer comprising a host and a dopant, and the emission layer further comprises a phosphorescent dopant.

15. The organic light-emitting device of claim 12, wherein at least one layer of the hole injection layer, the hole transport layer, and the hole injection and transport layer further comprises a charge generating material, in addition to the heterocyclic compound.

16. The organic light-emitting device of claim 15, wherein the charge generating material is a p-type dopant.

17. The organic light-emitting device of claim 12, wherein the organic layer further comprises an electron transport layer, and the electron transfer layer comprises an electron transporting organic compound and a metal-containing material.

18. The organic light-emitting device of claim 17, wherein the metal-containing material comprises a lithium (Li) complex.

19. The organic light-emitting device of claim 11, wherein at least one layer in the organic layer is formed using a wet process.

* * * * *